United States Patent
Gan et al.

(10) Patent No.: US 6,818,429 B2
(45) Date of Patent: Nov. 16, 2004

(54) ISOLATED HUMAN PROTEASE PROTEINS, NUCLEIC ACID MOLECULES ENCODING HUMAN PROTEASE PROTEINS, AND USES THEREOF

(75) Inventors: Weiniu Gan, Gaithersburg, MD (US); Karen A. Ketchum, Germantown, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 112 days.

(21) Appl. No.: 10/212,877

(22) Filed: Aug. 7, 2002

(65) Prior Publication Data

US 2003/0017574 A1 Jan. 23, 2003

Related U.S. Application Data

(62) Division of application No. 09/813,133, filed on Mar. 21, 2001, now Pat. No. 6,455,294.

(51) Int. Cl.⁷ ............................. C12N 9/64; C12N 9/48

(52) U.S. Cl. .......................................... 435/226; 435/222
(58) Field of Search ................................. 435/212, 226

(56) References Cited

U.S. PATENT DOCUMENTS 5,474,901 A    12/1995  Drayna et al.

OTHER PUBLICATIONS

Eaton et al. "Isolation, Molecular Cloning, and Partial Characterization of a Novel Carboxypeptidase B from Human Plasma." J. Biol. Chem. Nov. 15, 1991. vol. 266, No. 32, pp. 21833–21838.
International Search Report dated May 27, 2003. for PCT/US02/08289.

*Primary Examiner*—David J Steadman
(74) *Attorney, Agent, or Firm*—Celera Genomics; Lin Sun-Hoffman

(57) ABSTRACT

The present invention provides amino acid sequences of peptides that are encoded by genes within the human genome, the protease peptides of the present invention. The present invention specifically provides isolated peptide and nucleic acid molecules, methods of identifying orthologs and paralogs of the protease peptides, and methods of identifying modulators of the protease peptides.

5 Claims, 26 Drawing Sheets

```
   1 GAAAATTGCT GTTGGGATGA AGCTTTGCAG CCTTGCAGTC CTTGTACCCA
  51 TTGTTCTCTT CTGTGAGCAG CATGTCTTCG CGTTTCAGAG TGGCCAAGTT
 101 CTAGCTGCTC TTCCTAGAAC CTCTAGGCAA GTTCAAGTTC TACAGAATCT
 151 TACTACAACA TATGAGATTG TTCTCTGGCA GCCGGTAACA GCTGACCTTA
 201 TTGTGAAGAA AAAACAAGTC CATTTTTTTG TAAATGCATC TGATGTCGAC
 251 AATGTGAAAG CCCATTTAAA TGTGAGCGGA ATTCCATGCA GTGTCTTGCT
 301 GGCAGATGTG GAAGATCTTA TTCAACAGCA GATTTCCAAC GACACAGTCA
 351 GCCCCCGAGC CTCCGCATCG TACTATGAAC AGTATCACTC ACTAAATGAA
 401 ATCTATTCTT GGATAGAATT TATAACTGAG AGGCATCCTG ATATGCTTAC
 451 AAAAATCCAC ATTGGATCCT CATTTGAGAA GTACCCACTC TATGTTTTAA
 501 AGGTTTCTGG AAAAGAACAA GCAGCCAAAA ATGCCATATG GATTGACTGT
 551 GGAATCCATG CCAGAGAATG GATCTCTCCT GCTTTCTGCT TGTGGTTCAT
 601 AGGCCATAAT CGAATGTGGA GAAAGAACCG TTCTTTCTAT GCGAACAATC
 651 ATTGCATCGG AACAGACCTG AATAGGAACT TTGCTTCCAA ACACTGGTGT
 701 GAGGAAGGTG CATCCAGTTC CTCATGCTCG GAAACCTACT GTGGACTTTA
 751 TCCTGAGTCA GAACCAGAAG TGAAGGCAGT GGCTAGTTTC TTGAGAAGAA
 801 ATATCAACCA GATTAAAGCA TACATCAGCA TGCATTCATA CTCCCAGCAT
 851 ATAGTGTTTC CATATTCCTA TACACGAAGT AAAAGCAAAG ACCATGAGGA
 901 ACTGTCTCTA GTAGCCAGTG AAGCAGTTCG TGCTATTGAG AAAATTAGTA
 951 AAAATACCAG GTATACACAT GGCCATGGCT CAGAAACCTT ATACCTAGCT
1001 CCTGGAGGTG GGGACGATTG GATCTATGAT TTGGGCATCA AATATTCGTT
1051 TACAATTGAA CTTCGAGATA CGGGCACATA CGGATTCTTG CTGCCGGAGC
1101 GTTACATCAA ACCCACCTGT AGAGAAGCTT TTGCCGCTGT CTCTAAAATA
1151 GCTTGGCATG TCATTAGGAA TGTTTAATGC CCCTGATTTT ATCATTCTGC
1201 TTCCGTATTT TAATTTACTG ATTCCAGCAA GACCAAATCA TTGTATCAGA
1251 TTATTTTTAA GTTTTATCCG TAGTTTTGAT AAAAGATTTT CCTATTCCTT
1301 GGTTCTGTCA GAGAACCTAA TAAGTGCTAC TTTGCCATTA AGGCAGACTA
1351 GGGTTCATGT CTTTTTACCC TTTAAAAAAA ATTGTAAAAG TCTAGTTACC
1401 TACTTTTTCT TTGATTTTCG ACGTTTGACT AGCCATCTCA AGCAAGTTTC
1451 GACGTTTGAC TAGCCATCTC AAGCAAGTTT AATCAATGAT CATCTCACGC
1501 TGATCATTGG ATCCTACTCA ACAAAAGGAA GGGTGGTCAG AAGTACATTA
1551 AAGATTTCTG CTCCAAATTT TCAATAAATT TCTGCTTGTG CCTTTAAAAA
1601 AAAAAATAAA AAAAAAAAAA TACAT
```
(SEQ ID NO:1)

FEATURES:
5'UTR:        1 - 16
Start Codon:  17
Stop Codon:   1175
3'UTR:        1178

Homologous proteins:

| Sequences producing significant alignments: | Score (bits) | E value |
|---|---|---|
| CRA\|335001098689571 /altid=gi\|11434004 /def=ref\|XP_007121.1\| pl... | 784 | 0.0 |
| CRA\|18000004896001 /altid=gi\|4503005 /def=ref\|NP_001863.1\| plas... | 781 | 0.0 |
| CRA\|335001098689569 /altid=gi\|11433998 /def=ref\|XP_007120.1\| ca... | 720 | 0.0 |
| CRA\|11000480563026 /altid=gi\|7706531 /def=ref\|NP_057497.1\| carb... | 719 | 0.0 |
| CRA\|88000001156039 /altid=gi\|7416967 /def=gb\|AAF62385.1\|AF16452... | 670 | 0.0 |
| CRA\|1000682331241 /altid=gi\|9789915 /def=ref\|NP_062749.1\| carbo... | 665 | 0.0 |
| CRA\|335001098694742 /altid=gi\|11526577 /def=dbj\|BAB18617.1\| (AB... | 659 | 0.0 |
| CRA\|113000004114371 /altid=gi\|8217501 /def=emb\|CAB92622.1\| (AL1... | 406 | e-112 |
| CRA\|1000682332502 /altid=gi\|6013463 /def=gb\|AAF01344.1\| (AF1902... | 312 | 9e-84 |
| CRA\|18000004936445 /altid=gi\|6978697 /def=ref\|NP_036665.1\| carb... | 303 | 4e-81 |

FIGURE 1A

EST:

```
Sequences producing significant alignments:        Score    E
gi|12799562 /dataset=dbest /taxon=960...           (bits)   Value
gi|9867993  /dataset=dbest /taxon=960...           1104     0.0
gi|9872723  /dataset=dbest /taxon=960...           1021     0.0
gi|12799561 /dataset=dbest /taxon=960...           1013     0.0
gi|10295921 /dataset=dbest /taxon=96...            999      0.0
gi|10294900 /dataset=dbest /taxon=96...            930      0.0
gi|10293895 /dataset=dbest /taxon=96...            930      0.0
gi|9879404  /dataset=dbest /taxon=960...           924      0.0
gi|10300396 /dataset=dbest /taxon=96...            922      0.0
gi|8140358  /dataset=dbest /taxon=960...           918      0.0
                                                   878      0.0
```

EXPRESSION INFORMATION FOR MODULATORY USE:
gi|12799562 /Fetal brain
gi|9867993 /liver
gi|10295921 /hepatocellular carcinoma Tissue Expression:
Whole liver

FIGURE 1B

```
  1 MKLCSLAVLV PIVLFCEQHV FAFQSGQVLA ALPRTSRQVQ VLQNLTTTYE
 51 IVLWQPVTAD LIVKKKQVHF FVNASDVDNV KAHLNVSGIP CSVLLADVED
101 LIQQQISNDT VSPRASASYY EQYHSLNEIY SWIEFITERH PDMLTKIHIG
151 SSFEKYPLYV LKVSGKEQAA KNAIWIDCGI HAREWISPAF CLWFIGHNRM
201 WRKNRSFYAN NHCIGTDLNR NFASKHWCEE GASSSSCSET YCGLYPESEP
251 EVKAVASFLR RNINQIKAYI SMHSYSQHIV FPYSYTRSKS KDHEELSLVA
301 SEAVRAIEKI SKNTRYTHGH GSETLYLAPG GGDDWIYDLG IKYSFTIELR
351 DTGTYGFLLP ERYIKPTCRE AFAAVSKIAW HVIRNV
    (SEQ ID NO:2)
```

FEATURES:
Functional domains and key regions:
[1] PDOC00001 PS00001 ASN_GLYCOSYLATION
N-glycosylation site Number of matches: 5
```
    1      44-47   NLTT
    2      73-76   NASD
    3      85-88   NVSG
    4     108-111  NDTV
    5     204-207  NRSF
```

[2] PDOC00005 PS00005 PKC_PHOSPHO_SITE
Protein kinase C phosphorylation site

Number of matches: 5
```
    1      35-37   TSR
    2     112-114  SPR
    3     137-139  TER
    4     164-166  SGK
    5     367-369  TCR
```

[3] PDOC00006 PS00006 CK2_PHOSPHO_SITE
Casein kinase II phosphorylation site

Number of matches: 10
```
    1      47-50   TTYE
    2      75-78   SDVD
    3     118-121  SYYE
    4     125-128  SLNE
    5     131-134  SWIE
    6     151-154  SSFE
    7     164-167  SGKE
    8     236-239  SCSE
    9     248-251  SEPE
   10     367-370  TCRE
```

[4] PDOC00008 PS00008 MYRISTYL
N-myristoylation site

Number of matches: 5
```
    1      26-31   GQVLAA
    2      88-93   GIPCSV
    3     215-220  GTDLNR
    4     231-236  GASSSS
    5     340-345  GIKYSF
```

Membrane spanning structure and domains:
```
  Helix Begin    End   Score  Certainty
    1      3      23   1.035  Certain
```

FIGURE 2A

BLAST Alignment to Top Hit:
Alignment to top blast hit:

BLAST Alignment:>CRA|335001098689571 /altid=gi|11434004 /def=ref|XP_007121.1| plasma
    carboxypeptidase B2 precursor [Homo sapiens] /org=Homo
    sapiens /taxon=9606 /dataset=nraa /length=423
        Length = 423

Score =  784 bits (2003), Expect = 0.0
 Identities = 386/423 (91%), Positives = 386/423 (91%), Gaps = 37/423 (8%)
 Frame = +2

Query: 17    MKLCSLAVLVPIVLFCEQHVFAFQSGQVLAALPRTSRQVQVLQNLTTTYEIVLWQPVTAD 196
             MKLCSLAVLVPIVLFCEQHVFAFQSGQVLAALPRTSRQVQVLQNLTTTYEIVLWQPVTAD
Sbjct: 1     MKLCSLAVLVPIVLFCEQHVFAFQSGQVLAALPRTSRQVQVLQNLTTTYEIVLWQPVTAD 60

Query: 197   LIVKKKQVHFFVNASDVDNVKAHLNVSGIPCSVLLADVEDLIQQQISNDTVSPRASASYY 376
             LIVKKKQVHFFVNASDVDNVKAHLNVSGIPCSVLLADVEDLIQQQISNDTVSPRASASYY
Sbjct: 61    LIVKKKQVHFFVNASDVDNVKAHLNVSGIPCSVLLADVEDLIQQQISNDTVSPRASASYY 120

Query: 377   EQYHSLNEIYSWIEFITERHPDMLTKIHIGSSFEKYPLYVLKVSGKEQAAKNAIWIDCGI 556
             EQYHSLNEIYSWIEFITERHPDMLTKIHIGSSFEKYPLYVLKVSGKEQAAKNAIWIDCGI
Sbjct: 121   EQYHSLNEIYSWIEFITERHPDMLTKIHIGSSFEKYPLYVLKVSGKEQAAKNAIWIDCGI 180

Query: 557   HAREWISPAFCLWFIGH-----------------------------------NRMWRK 625
             HAREWISPAFCLWFIGH                                   NRMWRK
Sbjct: 181   HAREWISPAFCLWFIGHITQFYGIIGQYTNLLRLVDFYVMPVVNVDGYDYSWKKNRMWRK 240

Query: 626   NRSFYANNHCIGTDLNRNFASKHWCEEGASSSSCSETYCGLYPESEPEVKAVASFLRRNI 805
             NRSFYANNHCIGTDLNRNFASKHWCEEGASSSSCSETYCGLYPESEPEVKAVASFLRRNI
Sbjct: 241   NRSFYANNHCIGTDLNRNFASKHWCEEGASSSSCSETYCGLYPESEPEVKAVASFLRRNI 300

Query: 806   NQIKAYISMHSYSQHIVFPYSYTRSKSKDHEELSLVASEAVRAIEKISKNTRYTHGHGSE 985
             NQIKAYISMHSYSQHIVFPYSYTRSKSKDHEELSLVASEAVRAIEKISKNTRYTHGHGSE
Sbjct: 301   NQIKAYISMHSYSQHIVFPYSYTRSKSKDHEELSLVASEAVRAIEKISKNTRYTHGHGSE 360

Query: 986   TLYLAPGGGDDWIYDLGIKYSFTIELRDTGTYGFLLPERYIKPTCREAFAAVSKIAWHVI 1165
             TLYLAPGGGDDWIYDLGIKYSFTIELRDTGTYGFLLPERYIKPTCREAFAAVSKIAWHVI
Sbjct: 361   TLYLAPGGGDDWIYDLGIKYSFTIELRDTGTYGFLLPERYIKPTCREAFAAVSKIAWHVI 420

Query: 1166  RNV 1174
             RNV
Sbjct: 421   RNV 423 (SEQ ID NO:4)

Hmmer search results (Pfam):
Scores for sequence family classification (score includes all domains):
Model     Description                                          Score    E-value  N
--------  -----------                                          -----    -------  ---
PF00246   Zinc carboxypeptidase                                330.5    1.9e-95  2

Parsed for domains:
Model     Domain   seq-f  seq-t    hmm-f  hmm-t     score   E-value
--------  -------  -----  -----    -----  -----     -----   -------
PF00246    1/2      123    196 ..      1     77 [.    96.3   4.5e-25
PF00246    2/2      197    370 ..    116    304 .]   236.6   3.4e-67

FIGURE 2B

```
   1 TCGAATATTA CATTCAGCTA AACTAGTACT TGAAAGTGAA GGCAAAAGAA
  51 AGTTATTGTT AAAGATACAG AGCATAAAAG ATTTTATCAC CTGTAGACTT
 101 TTGCTATAGG AACTTTTAAA AGATTGCTTC AGCAATAAGA AATGTAATTT
 151 AAAATTTATT GTTTTTTATG CACTCTGTTT CTTTTGTATC CTGTTTCTGT
 201 TTCCCCAGAG AGGAAACAGG ACATAAAATA AAGAAGAAAC ACAGATACAA
 251 AATAAGTAGC ACAAAAATTG ATAGAATTTA TTAGCATATT TTAACTATTT
 301 TGACTGTTTA TTTTAAAGTT AACTTTTATG TTAAAAAGAT AAGGTAAAAG
 351 TTACTTGGGT TAGTTTTTCT TTCTCTCCTT CAGTGTGATT ATGTTATTCA
 401 TTTGAAACAC AGGTTCGTTT TTGTTTGTAT TATTTTTTAA AATTTATTTG
 451 TTTGCTTGTT TTAAGTACAT ATGTGAAAAG AACATGGTTC TAAAATTCAG
 501 AGTAGTTCTA AAGTTCAGAA CTATTCAAAA CACTTCACCC AAAGAAGCGT
 551 CCCTCCCTGT CTCTTCTACC CTGTCTTTTC CAGTGTGTTT CCACTCACCT
 601 CCCGTGGATA ACCAGTCTCA TTGATTTCTA ATCTATCCTT CTTATGTTTC
 651 TTTCTCCACA TATGAGCAGA CACACACATA TTTTCTTATT TCTTCTTCTT
 701 TCTTATACAA CAAGTGGTTA CAGTGGAAGT CACTTTAATT CATTAAATAT
 751 CATTCAATAG TTTTAAATCT CAAAAGGAAA AGTTTGAAAT CTCAATCATT
 801 TTCTTCTGGC CAGGCACGAT GGCTCACGCC TGTATTCCCA GCACTTTGGA
 851 AGGCAGAGGC AGGTGGATCT CCTGAGCTCA GGAGTTTGAG ACCATCCAGG
 901 GCAACATGGT GCAACCCTGT CTCTACTAAA AATACAAAAA AAATTAACCG
 951 GGTGTGGTGG GGCACACCTC TAGTCCCAGC TACTTGGGAG GCTGAGGCAG
1001 GAGAATTGCT TGAGCCCCAG AGGTGAAGGT TGCAGTGAGC CAAGATCACG
1051 CCTCTGCACT CCAGCTTGGG CTACAGAGTG AGACTCTGTC TCAAAAAAAA
1101 AAAAAAAAGA AAAGAAAAAT CATTTTCTTC TCAGAAGTTA
1151 ATTGTGGGCA GGCTGATTTA TTTTGCAAAT TTGCCAATTC TGACTTCAAG
1201 AACATTCAAG TGCATTAACC AATGGGAATG TAGGGGAAGA GGGCTCCACT
1251 CACTTACAGA GGGTAGGATA TGGCCTCATA CTAGACAAAA TGTTATTTGA
1301 TGCTACTTTC AAGATGATAG GGGATGGGCC TGGATTTAAT TGATGGCTAT
1351 TATGGTGACC TTTAAATAAA TGAGATTCAA AGTAACCTGA TGTCTTTACT
1401 GCTTGAACCA GCTTCCATGA AATAGTATTC CTATTGGGGG TGGGCCTATC
1451 ATTCCATATG GTCAAGGAAA CATCTTTTTG AACAGAGATC CTGTAATCAT
1501 CCTTACAAAC TGCACTTCAA CATTGGATTG GATTAGCCAG ATTTGAGGAA
1551 CTCACTTTTT ACGTCTTCAT AAATTTAAAA TGTTGAAAAA GTCAGAGGCA
1601 AGGGAAGACA TTTATAGTAC TTCACGGTAG ATCTCCCTCA ACATGGGCTA
1651 TATATCCATT AGTCAATATT CTATAGCTAT TGTTCTGCAA TAAACCAGAC
1701 AAGATCCTAC TGTATTACTA CCCTTTTATT CTTGGCCCTA CCTTCCCCAA
1751 GGAGTTACAC ATTTTCTAGA TAGTCTAAAT TAAGAGCAAC TCTCATCATA
1801 CTCTTTTTGA GTGTTTAATT ATCAAGCAAC AGCCTAACTA AGCCAATAAT
1851 ATTTCTCTTT TTGGGAGTGG AAATGAAGC TAAGTTGATT GACCCACAGG
1901 AACAAGAGGG AACATGCCGT TATATTTTAA CCAGTGTGTA AAGAAGGCTG
1951 TTATGCAATC AATGATCTGG GTTTTTCTCT TCAGAGAAAT TTGTTGTACA
2001 GAAAATTGCT GTTGGGATGA AGCTTTGCAG CCTTGCAGTC CTTGTACCCA
2051 TTGTTCTCTT CTGTGAGCAG CATGTCTTCG CGTTTCAGAG GTAACCCAAT
2101 AGAATCTTAG ACTGTGGTGG GCCACTCTCC TCACTTGTTT GCCTCATGTC
2151 GTGTCAAGTC AGTGCACTGA GCTGGTGGAC AAAATGGTAA ACTTTGAAGG
2201 CCAGGTCTTT CAGAACTTTC CAAGTTGCCC TGACAAATAA GTAGACTTTA
2251 GCACAATGGG CTATCCTAA AGACAGGGTC TTTTTTCTTT CCTGCTCTCTG
2301 GTTTTATTAT TGGGAGAACC TTGGATGATA CGCATATCCA GTGACTATGG
2351 AGATTCAAGA AATTAAATCT TTTATAAACG TAACTATTTA TACTCTAACT
2401 TGATGTATGA TTCATATTCT TCCTGTCTTC ACATAAAAAA AGTTAACTAT
2451 GGATCATTTA TTTTCCCCTT GTACATGGAA CATAGGAGGA AGAAGAGGGT
2501 GAAGTGTTAA ATAGGAGGTT TGGATCATGC ATGATTATTT AGCATGGAAT
2551 ATGAAAGGAA GAAGAGTTGT GTGATAAAGA ACTATTATCT GATTCTTATT
2601 TTGCTTAGTA GATTCCCTTA GGATAAACTA TCTAGAAGAA CACAAATGAA
2651 TTCATGCTAT AGCACATGCA ATGCATGGAG AAAATAGTTC CAGGGTATAT
2701 GTAATGTAAT TTATTAAGTA GTCAATTTTT AGGCTTTAAA ACATTGATAT
2751 TGTTTCCTTT GGAATTATCT TATTTTTTCC CCTTTGTTTT GGTTCTATGA
2801 TCGCTTTCTC CTCCAATTAT CTTTGAGACA GATCCCTCTC CTCATGTTAG
2851 TAAATGACAA AGAAAGAAGA GACATAGGGC AAAGGAATAT ACCAGTGACA
2901 AGGAACATTC TACCACCAAA AAAATGTTCA CGGTCATAAA TAACCATAGG
2951 ACAATGGTTT GGAAATAGA TCTTGACTTG TGAGCCTGAA GCTGTGTTTG
3001 TACATGATCA CTGAACTGAT TATAGTTGAT TGATCTTCTT TTGTTCAACA
3051 TGATTGTCGA ATGTCGAGCA ACAAATTCTA TCATAAAATG ATATTATTTT
3101 TGTTTATTTAA TTGACGTGGG GGTCAAGATT GCTGCAATGA TCAGTGACTT
3151 ATGTCTTTCT CTGTATTTTA TCGGTGAATC ATATGGTCAG GATTTCTAAG
3201 GTTCTTGCTA GTTCTAATAT TCCATAACTT GATAATTGCC TTCAGTTAAG
3251 GGAAAGGGGG AGAAGAGAAA AATTGGTATC AACATGTCCA ACTTGGCTAC
3301 TGTACACAGT GGCAGTACCA TTGACAGTTA GGGGAAAGGG AGGAAACCTC
3351 TGCTTATTTA GTGCCTGTGT TTGTGCCAGG CACTGAACTA GTCACTTAGA
3401 AATGTTATCT CTTTAAATGC ATAAAATCCT ACATGCTAGG AATCTTTACT
3451 GACATTTTAC AAAGGAGGAA ACTGAGCCTC AGGAAGAATA AATAATTGGC
3501 CCAAGATCAA ACAGTAAATG TAGAGCTTGG ATTCAAACCC ACTTTAGCCT
3551 CATTTCAACT CCATGCACTG GACAGCATTG CCTCCATAAA ATCTGGAAAT
3601 TAGGAAGAGA GCCAGTTTGA AGGAAGGTCA GATTTAGTCA AAGGGAGTTG
3651 CAGGCAGCAG TTGGTTTGGA AAGTAGCTTG GAAGAGAGGT TCGGGATTAG
3701 AGGTTCAGTC TCATGCTTCT CACCCACTAG CAGATCTAAT CATGGCCTTG
3751 GCGTCAGCCC AGTGCAATTA TCCTCAGCTG GTTGTTGCAG AGGTTGGCGG
3801 GCAGGTGGGC TCACTGCAGA CCGCCATCTT GATCGTAGAG TAACCCAAAC
```

FIGURE 3A

```
3851 TCTTGGATAG GATAATCAAT AGCAAAACAC ACTAAAAGCT TTAGCACATC
3901 TCTTCAAATG AGTACGTGTA TAGCAGCTTA GTGACACTAA ATATAACGCA
3951 AATAGAAGAA GTAGCCAACA ATAAAATAGT AAAAAAATGA GTGAGAACAT
4001 ATCTTCATGC ATGGGCTTTG TTACTATTTG TTGCTTCAGC TTATACTCTG
4051 AAATCTGACT GATACTTATG CTTGAAAAAA GGAATGAGAA TGTGACTATA
4101 TTTTAACCAA AGAATATCAC ATTAAAAATA TTTAATACTT TTGCATACTG
4151 CGAGGGTCCC TTTGCAGAGG AGAGGAGGTA GGAGGACCTC AGTATTGTAG
4201 ACAGATGAAT ATCTGAATCC TGGTTCCCAT CCCTTCACTG GAAATAACAT
4251 TGCAAACTAC TCTTTCTGTG AGTAAAAATA AATTTTTTTA CCAAATGTTT
4301 CTGTGCTCCA CTTTTCCAGG AATGGCCTAT TCCTGAAGCT AAAAAGGAAA
4351 TCTAATTTCA TTCAGGGCAA CAGACTTTGA TAAATTGTTG CTGGGGTTCA
4401 GAATATCAAC CCTTCTAAAA AAAAAAAAAA AAAACTAACA GTCTGGCTTT
4451 TTCTTAAAGC TGTTCTTTGT TTTTTTTTTT TTTTTTTTGT CATAATCATT
4501 TTCCTACTAA CAGTTTTTAT TCATGCAGTC TCTTAGTGGC TGATTTGTAG
4551 GTTCATTTTG ATAAATTTCA TCAGTGAAAT GCCCTGGAAC AACAACAAGT
4601 TTTAAAGGCA TAAATATCAT ATGCCAAAGG GAAAGGCAGC CAAAAAATCA
4651 TGACTCCATA TTCATTTGCT TTTAAAAGCC AAACACTATA AAGGGTAAAA
4701 ATAAAATACT AGCAAGAATC TTGTAAACAG AATCAGTAAT TGTATTGTGC
4751 AGTGATTACC TAAATGCAGC CTGCCAGCCC AGACTATTTG GAAAGAGGAA
4801 GTAAGAGACA CTAGGAAGAA GACTTAGGAA TTAGAGAGTG GAGGAGGGTT
4851 GAGGATAAAG GGCTTCTGAA TTATTAATAG ACCACAGGAA GTGTTCCTCT
4901 GTTGACTTCA CATACTGTTT GGGTACCTGG AGACCAGTTT ACTCTCTTTC
4951 ACTTTGTTCC TACTGATGTA TTGTTTTCAT CTCAAAGAAC AGGCCACCAG
5001 TGGCCTTAAA ACACTGTAAT GTGTGCAACA AAATTGCAGC CTTGGGCTAT
5051 GTTCCATTGT TCAGAGACAT CTTGCCAGCT TTTTAAATTC AAAATAATCT
5101 TTCAGAATGG TGAAAGTGTG AACCCTCCCC TGTAAACCAT AGCAGGGGAT
5151 ACACCCCAAT GAACATAATG ACATTCTCAG AAGGGAAGGA ACAGAGGAAG
5201 TGTTGCATAG GTATTAAAAG CTCAGGATCT GGATTCGAGC CCCAGATCTG
5251 CTACTTATCA CCCATGCAGA CTTGGGCAAT TTGCTCGTCC CCTTTCAGCC
5301 TTTACTTTTT TTGTAAAGTG ACCTGTTACT TCACTGTGCT TGTACTTCTC
5351 ATTCGATTTT TGGTGCAAGG CTGTTCTTTT TTCTCAAGTG GTTATTGTGT
5401 AAGTGCTATA ATCGTATCAT TCAGAGACGC AGTTGAAACA CAGCTTTAGT
5451 TTTTGTCTCC CATTGCCCCA TGACATTTTG CGTAGTGGGG TTATCTATCA
5501 CTGCTCTCGC ATGGAAAGTT AGAAAATTTC AAGGCTTTTT AGCCTGCTTT
5551 TAAGTGACAG TCCTTGGGTC CTGCTAAAAA TACAAATAGC CTCAATTTAG
5601 AAATTAGAAT GTCACCTCCA ACCAAGGTAT TGTTCAAATA TCCCCATCTT
5651 TGTTGTTAAA AGAAAATCTT TAAAAGAATT ATATTTAGCA AAATTTAATT
5701 GAACAAAGAA CAATTTTCTA ATCAAGTAAC CCTCAAAAAC GAAAGAAGTT
5751 CAGAGAGTTC TGCTCAGCAA AGTGGGCAGG CAGCACTTAT AAACAGCAAA
5801 TGGAAATGAG GTCCAGAAGC AGCTTGAGTA GTTACAGGTG AGCAGTTGTC
5851 TTACTGGGCA TAGGCTGATC AGTTGGCCAC ATGGGATTGG CTGTAGCTTG
5901 GCTGCTGTGA TTGGCTGAGA CTCACCTCGT TAGTACAAAA AAAAAATACT
5951 CCTAAGTTAG GTTGCAGTTT GTTATGTAGC GACTCAAGTT ACGAGGCATC
6001 CTCAGACCAA ATTTAGTTTA ATTTAACATT ATTTATAGGA AAACAACTGC
6051 CTCACCTCTT CCACAAACAC ACCTTACTCT TTTTCTTGTT AGTCTTTTTC
6101 TCGAGTTCTA ACTTCTTAGA GTTGTGTGAG ACATCTTTAT TGGGGAAGCC
6151 TCTGGACCAG GACAGATGCT TCTTTGTCTA GGTTTTCACT TGCGACTCCA
6201 TCCTTCCCCG CTAAGAGTCT TGCTTCTACC TCTGGGCTCT TGTTGTTGAG
6251 AACTTTCCAT CCCTTTAGGT GGCCCTATTG GATGGCATCT AACATTAAGT
6301 GTTTCTTTTC ATTTTAACTA CTACTATCTA GCCAACTAGA GACCAGCCAC
6351 ATGCAGGTTT AGCTTTATCA GGAGAAGCCA GGCACCAGTC TTTGTGTCTG
6401 TAAATTTGAG GAAACATCCA ACTCTCTCAT TATCTCCTGG AAGTCCCCCT
6451 ACTAGGCTGA GGTAAGGGGA GTGCACCCCG AAACTTCATC CCTTTGGGAG
6501 GGTGGTGACT TACAGAACCA TAAAAACATG CTAAAAAAAA AATTCACAAA
6551 TCCTCTCCCT CTTTTCCACTC TGACAGCTTT TTATATAGCC TGTTTATGAC
6601 TAAGTAAGGG GAAGCAGTCA TGAAACCAGT TTCCAAAAAT AGAGTGATCT
6651 GACTGACCCT CATCCCATTA CCTAACTCTG TTGTGTTAGC ACTTTGCTCA
6701 AATTCTGCAT AAGAAGAGTC TGTTCACTAC AAGCTGAACT TGGACATATC
6751 AATAAATTTT TGGTGAATTT TTAACTTCAT AATTTTACTC ACTATTTCCT
6801 AACTTATTTT TTGAATTTCC TTTATTTTTT CTTCTTAAGA GGTCTCATTT
6851 GGATAACATA CATTTTTACC TTTATATTTT CTTTCTTTCT CTGCTTGTTG
6901 ACTAATTTTT ATACTTTTCT CCTTCTTTAA TACATTAGGT TTTTTTTTAA
6951 TTTAATACTG CCCACTCAAC ATTTTTTGTT CATTATTTTC TTTCTTTCTT
7001 TTGAGACCTA GTCATGCTCT CTTACCCAGG TGGAGTCCA TGATTTGTGAT
7051 TTTGGCTCAC TGTAACCTCC ACCTCGTGGG TTCAAGTGAT TCTCGTGCTT
7101 CAGCCTTCTG AGTAGCTGGG ACTACAGGTG TGAGCTACTA TGCCACGCTT
7151 ATTTTTGTAT TTTTAGTAAA GACAGGGTTT CACCATGTTG GTCAGGCTGG
7201 TCTTGAACTC CTGACCTCAG GTGATCCACC CACCTCGGCC TCCCAAAGTG
7251 CTGGGATTAC AGGCGTGAGC CACTGTGCCT GGCCCATTAT TTTCAATATA
7301 ATAGATTATC TACCATACTG CCTTGTGAGG ATTAAATAAG AATACCTGTA
7351 AAGCACTTAG CACAATATCC AAGTTACTAA ATATCAGTAA AAAAGAAGAA
7401 AAGTCCCCCC AGACATATTA TGCTCTAGTC AACACAAGAC TTCCTCTACA
7451 TGGACTTGAA ATTCAGCATC TCTTTAGATA ATGAAGAGCT CATTGCTTGA
7501 TAAGGTGTCC TATCTCATGG TTAGCTCAAA TTGTTAGAAG TTCACACTGA
7551 AATTACAGTG ATTTAATGAT ATGAACCTCC ACTTCTCTAT ACTTTACATG
7601 AAAAGGAAGC TTTGAGTTTG CCACATCTTT TGCTACAACT CCCAAAATCA
7651 TGCCCAACCA ACTTTTAAGT AAGGGCCACA ATCTTGACCC CAGCATTTAA
```

FIGURE 3B

```
 7701 GACCCTTAAC AATCAGGTCC TACCCTGCCA TTCGTCCTGG CTTTATTTCC
 7751 TGGTATATCT CTATATAGGC CCCATATTTC TGCCCAGCTG GATCACTTCT
 7801 CCTTCCTTGA GCTCTGATTT TACTTTTCTA CTTGTGCACC TGCATTTATG
 7851 ATGTTTCATC TCCAATTCGT TTAGCAAAAT TCTGCCTATG TTAGTCTTAT
 7901 ACCATCTCAT CTTCCCTTCA CCTATTGAAT CCTAGTATCT CAGAAGTCCA
 7951 ACTCAGAATA TCTCCATTCT CTGACTACGT AAGTCAAAAA TGATACCTGA
 8001 CTTTGTATTC CTGTAGCAGA ATATTTATAC CACTCGCATT GTACTTTTAG
 8051 TGTTTTATCT CACAGAATAG GCATTTGTAT CAGTTGCAGG TTAGTTTCCC
 8101 CAGGAAACAG ACTCCTGAGA TGAAGATTGC ATGGAGGAAG TTTACTGGAA
 8151 AGGAATCTCA GGATCAGCAT CTGTGGAGGA ATGAAGGAAG AAGGCTTGGG
 8201 CAGAGGAGAA ACTGACCTGT GATGTAATCA CAACTATGGC CTCACCTGTT
 8251 CCTGTGGAGA GCCTTGAGGC TGGGTTGGCC TGGTAAAGTT GTCCCAAACT
 8301 GGGGCAAGCA GGCATGCCTT TGTAACCCCT GTTTATTAGT CACTGGGTGT
 8351 GGATTGTACC TTGGAGGAGG CATCATGTTG GGCAGCACAG CTCTCTTCAG
 8401 GCAAGGGCAA GTCCTAGAAA GGGACTCAGG TGAGAATATC AGCTGCCAAC
 8451 CCTCCCAGAA GCTGAGGATA CAAAGAAGCT GAGGAAAATAA GAGTTCATCC
 8501 CTGGATGGAG ATCTAGGCAG CAAAACGTGA CATCTACTAC AGTCCAACCC
 8551 TTTGTGTCAC TCAGGTCAAT TTTCTTCATA AAATAAGCTT TGAGATCAAC
 8601 TCTTCTGGGG TTTTGCTTGG TCCCTCTTCC TAAAGGAAAT ATACAAGAGG
 8651 AACGTTAGTG AAATAAACTA CAACCTTCAC AGCTACAGCT AGTCTCGAGG
 8701 CCATAACCAA TACTTGTCAT TCCTCTTCTC CCCTACCCGT TCTGTTTTCC
 8751 CCAAAGAGGT GCCCTTTGCT AGCACCTCTT CTAATCTAGG TGGTTTACCT
 8801 GGTGAGACAA CCCAGACCCT CAATCCTCAA GGATCTGAGT CATAATCACT
 8851 GGGCCCTCTT GGGCCATGGC TGCTGCAATT GTCTGTATAC ATCAAATTTG
 8901 GACAAGGGAA TATTACAGAA CGCCTAAGCT GGATTCCAAA CATATTCTTC
 8951 CCTGCCACAT TCAGTATGTA AGTGCAGCCC TCAATGTCCT TCTGATTATT
 9001 GGAGTCAATT ACCCTTCCTG CATGGCTAGA AAACCCATGG TAACTCCTCG
 9051 CCTTCCTGAT AATCAATCAC CATGAGGAAA CTGAAATGAC TGGACAGTAA
 9101 CAACAGCTTT CAGTTTAAAG GAACTCTTCC TATGCTCTCT GGAAACCGGA
 9151 ATTTTTATAA GTACAGAGTC CATATTTGTA GATTTAAAGT ACTAATTCTC
 9201 CGAGTGGGTT ACTTGGAGTG ACGGTATATG GAAACACTCC AACTTGGTTC
 9251 CTGGAACCAT GTATACTACC TAGTAGGGAC ACAGCACCAC ATGAGTATTG
 9301 ATTTAAAGTG TGCACTGGAG GATGTTGCCT TCCAAGTTAG CACCTCAATT
 9351 GATCCTTCAA CAAACCATTT TTATTTCAGT AACAGGATAG CAGCAACTAG
 9401 GTATTCTGGT ATGTGAGAGG CTAAGTGGAT TCCATGGTAA TGGACCCATT
 9451 TCTGCAATTC CCTTGTTGTA AAGTGGAGCC CATGATCTGA TAGGATGTTA
 9501 TGTGAGATGT TTTATCAGTG GTCAAACACT CCGTAAGCCC TTGTATGGTG
 9551 ATGCTTGCCT GAGGCCCTAC AGGCAGGCGA GATAAACCCA TACCCAGAGT
 9601 GGAAGAGGAC AGATGTAGTC AACTTACCAC CCAGTGACTA GCTGGTCTCT
 9651 ATGAGGAATG GTGCTGATTC CGGGGCTCAA CTTTGGTCTC CGTTGCTGGC
 9701 AAGTTAGACA TGGGGCAGCA ACAGTAGCTA GATCAGCCTT AATGAGAGGA
 9751 GTCCGTGCTG CTGGAGCCAT GCACACTTCA TCTCTGCCAT CAGGCTATTC
 9801 TGTTCTAGTG CCTTTTGTGC CAGCATTGGG GTGGCTGTTG ACACAGGCTG
 9851 ACTGACATCA ATGGCTGAG TCATTTGTTT ATGCAGCTGT TTAATGTCTA
 9901 TTCTGTTGTG GGTGCTCCTG GTTAGGCATT AATAAATGAT ACAAAGATCT
 9951 TCACACTTTC TGCCCACTCT CATAGTTCCA TTCACATCCC CCTTTCTCCA
10001 ATCTCTTTGT CTCCAATCTG TCAAGATTTC TTCTTCCAGG TTCTTGAGGG
10051 GTTTTCCAGT CATGTCACTT GCCACTCTCC ATGAATTCCT GCATATTCTA
10101 ACACTGGAAA CACCTTTTCC ACCCAAGGTG TATGATGAGA TGCAACACTG
10151 AAGCTCTGCC TATTTGGGAC GATTTCCCTC TCTGCTCTCT TTCGGTCACC
10201 CGAGTGAGTC CATAATGCAG CACCCACTTCA CTTTTTTTTT TCTTTTTTGA
10251 GATGGAGTCT CCCTCTGTCG CCCAGGCTAG AGTGCAGTGG TGCGATATTA
10301 GCTCACTACA ACCTCTGCCT CCTGGGTTCA AGCAATTCTC CTGCCTCAGC
10351 CTCCCAAGTA GCTGGCATTA CAGGTGCCCG CCACCATGCC CAGCTAATTT
10401 TTTGTATTTT TAGTAGAGAT GGGATTTCAC CATATTGGCC AGGCTCGTCT
10451 CGAACTCCTG ACCTCAGGTG ATCCACCCAC CTCGGCCTCC CAAAGTGCTG
10501 GGATTACAAG CGTGAGCCAC CGTGCCCAGC CCACTTCATT TTTTACTTGT
10551 ACCCATGCAC TATCAACTTG ACTGTCCATG TATCAGACTT CCTCTTCCTA
10601 CTTGTGTCAG TTATGATCCT CTGAGAAGCA GACACCAAGA TGGGATTAGC
10651 TGTGCAAGAG GTGTGTTGAG GAAAATGCTT GGGTGCAAGA AATGGGGAGA
10701 GGGCTGGAGG AGGCTGGGAG AGCCATGAGA CTGCAATGCA AGCTTAACCC
10751 CTGTGGAGGA GAGAGGAAAG GAAGGAAGCA GGTAGGGAAC ATTTCAGGTC
10801 GTAGTGCAGT TCTAAGAAAG TTTTGGCAAA ACCAACCAAG AGTCCTGGCC
10851 AGGCACGGTG GCTCACACCT GTAATCCCAG CACTTTGAGA GGCCGAGGTG
10901 TGTGGATTAC CTGAGGTCAG GAGTTCGAGA CCAGCCTTAC CAATATGGTG
10951 AATCCCCGTT TTTACTAAAA ATACAAAAAT TAGCCAGGTG TGGTGGTGCG
11001 TGCCTGTAAT CCCAGTTACT CGAGAGGCTG AGGCAGGAGA ATCACTTGAA
11051 CCCACGAGGC AGAATTGTAG TGAGCCAAGA TTGCTCCATT GCACTCCAGC
11101 CTGGGTGACA AGAGCAAAAC TCTGTCTCAA AAAAAAAAAA AAAAAAAAAA
11151 AGTCCTATAG GCAGAGTCAC ACATCAGAAG AGTTTCCAGT TTTGTAGAAA
11201 GAGCCTCCCT TAGTATCCCC ACCATACTCA GTTATTAGCT GCAAGAAGCC
11251 AGTGGGAAAT GTGGTATTAG CACTAACACA GGGACAGATT TCAGAGCACA
11301 GTAGCTGGGG GCTTATATCA AGTACACATC TTGCAGCTGG AGAGTGAGAA
11351 AGTTAATTAA AGCTGAGGCA AGACTGTAAA TATGCACTGG TGTCTGTCCC
11401 AAGTGGATGT TAACTGTTCT GATGCTTTTT CCGACTGACA TATCCAGCGC
11451 AATAGCTGAA TACCATATGC CTGAGACTCT ACCCCGGCAA AGATGCCACA
11501 TCAAGCACTA TGGCTGCAAT TGAGATTGTT GCTTGGTTGA GTTTGATTGT
```

FIGURE 3C

```
11551 TTGCTGTCGT TTTCCAGGAT CCATCTGGTT TTTGTGGGAT CCAGATGGCA
11601 AATTAAATGT GGTTTTGATG GGATCTATCA TCCCTGCATC TTTTAGGTCT
11651 TTAAGGGTGG TACTGATATT TGTCATTTCC CCTCAAGGAT GAATTTTTTT
11701 TTTTTAATTT TGATATCTTG GCTGGGAGGT TGGGCAATTT CAGAGGTTTC
11751 CTTTTGGCTT TTCCCACTAT GATAGCTCTG GTCTTACAGT CAAGGAAACA
11801 ATGTGGAGGT TCTGCCAACT ACCTAGTATG TTCATGTCAA TTATACATTT
11851 GGTGACCAGG GAAATAATGA TGGGGGAATC CATTAACATG GTGCACCCGC
11901 TATGAGCTAG TCTTAGGCTA GGGCTCCAGA TACCCAAGTT TCAAAATCAA
11951 CTTGGATAGT GACCCTGCAT CCAACACACC TGAAAATATT TGAGTATTAC
12001 CCTTTCCCCA GGGTGCAGAC TTACCTGAGG AAATTTCCAT AGGTCTCTTT
12051 GGGAAAGGAC TGAAGGAGTC ATGATCTTTT TAGATTCTTT TTTTATACAG
12101 TTGCAGGGTC TTTCCTTGTG GGGACCTGAC TCCTCCTTCA GGCAAGAAAT
12151 TCTGGGTCTA AGAACAGCTC AGATCTGGAA AAGGGCAATG GATTATGACT
12201 TTTGATTAGG ATAGCTGTCC TCAGCCTCTC TCATTATCCA GCTTTGATTT
12251 ATTTTTATTG TAAAGATTGA GCAATCCTTT TGTTGGCTGC TTCTCTATCT
12301 TGCCCCTAAG AACTCTGTGT TCTCCTAACC GACTCCACAA TTTTCTAAGG
12351 GTCATGGTCC TCTGGCTGCC ATCTCCGACCT TACTGCTCAT TGTAATAACT
12401 GTGCCCAACT TGTTACTGGT GGTTAAGCCC TCCCGCCTGG CTTCTCTATA
12451 CAGGGATCTT AACATCTCCA TTGGTATCAG AGAGCTCAGT TCTGTAATGG
12501 CATGTCCTGT AGTTAGCCCT CAGGATCTAT TCCCACCTCC CCTCCTGGCC
12551 TTCAAGCCAA TAACCTAGGG TAGTCACAAC ATAAGCTGGC TGTGGAAGTG
12601 CTGGGCATGT TAACAAAGGA AAGGGACTAT ACCCCAAAGG AGGTGCACTC
12651 ACCCATGCTA CAGAATTTAA CATTCTAGTT AGTTCCTTGA GAGGTGGTAC
12701 AAACATGCTG TTAGGGTAGT TTTTGGAAGC TTGGAGAAAG CATGGCCTGC
12751 ACCATCTGAG CTAGAAATGT CAGAGCGAAT GTGGCAGATG GTGAAAAAAG
12801 AGATAGAGCA CACTAGAATA AAAATGCTAT GTAAGGCTAG AAAACCCACT
12851 GGGTGACTAT GCTACTCCAA GGGCCCAGAG AACATTCTGT TTATGAAAAT
12901 AATAAGGAAT GTGCTGGTGA GATGAGAGGG TTACCAGCAT CACTGAGAAG
12951 CTTGTTAGTG GCTTTTTCAC AGTCAAAGGA GATTTTTCTT TAAATTTAAT
13001 TTTCTTGAAT AAATACAAGA ATAGGAGTTC TTTTGGGTTT AAAAAGTAAA
13051 CAATACAGAA AAGCATAAAA TTAGGGAGAA AATACTAAAA TTTCACCATC
13101 CTGGTGAAAA TATGAACATG TTTGTGATCA TCCTTTCATA CATTTCTCCA
13151 CATAGTTATA CCTCCCTGGG TATAATTGTA TACTAGTTCA ATGTTGTATC
13201 TCCTATTGGT ACTATAGAAA CCTTTCTTTT AAAAAGAATC TCATTTGTTC
13251 TTCCCCTGCC ACTTACCCAA GGCTTCAATT GCCATTTCCC ACCCTCCAAA
13301 TCAAAGCTAA CAATGTGTTG TTTATTTATG TATAATTTTC TCCTGATTTT
13351 AACACATATA ATTTTTCTTT ATCTTTTCCA CTTTTTTCCA AAAATAGGAT
13401 CATATTTCAT AAAGTTCTCC ATATCTTGCT TTTCTCCCTT AATATGCCAT
13451 TTAAAGCCCC CAAGTTAACT GTTATAAATC AAACTCATTT TTTATAATGA
13501 CTGAAAAGCA TTCTAGAATG TGGAGACACT ACCAACATTC GACAATTCTG
13551 TTACTGCTGA GCATTCACAT GGTTTTTAGG TTTTGTTACT ATGAATAATG
13601 CCGTAATACA CATCCTTGAA CATGTATCTT TAATCAGTGG TTTAATAGTT
13651 TATGCTAAAC TTGTACCAGA GATTGACATA AAATTTCTCA GTCTAGCTAC
13701 TTTTCCCCTC TTCTAATAAG CAAGTCTCTC CATAGACTTA TTTCCAGAAT
13751 TCAGAATATT TTACTCAGGA TTTCCAAAAT AAAGCCACCC TCCACCCTTG
13801 TTAAAGTTAT CCTTGGTGGG CGCGGTGGCT CACGCCTGTA ATCCCAGCAT
13851 TTTGGGAGGC TGAGGCGGGT GGATTGTCTG AGGTCAGGAG TTCAAGACCA
13901 GCCTGACCAA CATGGTGAAA CCCCATCTCT ACTAAAAATA CAAAAATTAG
13951 CCGGGCATGG TGGTGCACGC CTGTAATCCC AGCTACTCAG GAGGCTAAGG
14001 CAGGAGAATC GCTTGAACCC AGAAGGTGGA GGTTGCAGTG AGCCAAGATC
14051 ACGCCATTGC ACTCCAGCCT GGGTGACAGA GCGAGACTCC ATCTCAAAAA
14101 CAAACAAACA AACAAAAACA AACAAAGGAA AACAAATAAA ATTATCCCTA
14151 TAAATCACAG CTCAAATGTT ACCTTTCTAA CTTCTAATTG CCTACAAGAT
14201 AAAGTCCAAA TTTCTCAGCA TGCATTCAAG ACCTTCTCTA GGGAAGGATG
14251 AACATAACTT CCCACACTCA TTTCTGTTTA GCTCCCATTC TTCTCTTGCT
14301 TTAAACACCC GTATCCTATA CTTGGCAACA ATGAACAAGA GCCATTTTTC
14351 CAAAAATGCC CTTTATCTCT TGCTATTGTG CCTTTACCCA CTCTTAGACA
14401 TTCTTACACA CCCAGACATC CCTTCTATGA AGCCTTTGCT AATAATGACA
14451 AACAGAAGTT ATCATAACCT CTTTTGTGCT TTGAGAGCTC TTGGTACATG
14501 GTTTTCTTAA ATAAGATGAT TTATTTGGAA TATTTTTAGA TTTACAGAAA
14551 AGTTGCCAAT TGTAATACAA CTGTATACCC CTCACCCAAT ATACCCTAAT
14601 GTTAACATTT TATATTATCA TGATGTATTA GTAAAAACTG AGAAATCAAC
14651 ATTGTTATAT TACTATTAAC TAAACTCCAG ACTTTTTTGG ATTTCACCAG
14701 TTTTCCCACT AAAGCTCTTT TTCTGTTCCG AGATCTAATC CAGAACACCA
14751 TGTTGCATTT AGTCATAATG TTGCTGTTGT CTAATGTCTT GAGTGCTGTT
14801 GTTCCATACA TTTTGTCCAG GTTTTTAGTT ATTTCATAAA GGAGGGTATA
14851 ACTGGAAGCA AAGTCTAAGA TTAGTTTTAA ATAAAGCAAG AGGAAGCATT
14901 TTTTCTAATT TAAAATATAT CTATCGTCAT ATTTCAAGGG CAATATTTGT
14951 TTGAAAATAA AAGAAAAATC TCGTTCAGTT AAAAAAAAGG GGGGGCTCAG
15001 AGCTGGCAAA TGCCACCAAC ATGCTTAATT TTAATTTAAA TAAAATAGTT
15051 CTTGTGAGGT TACTCAGTGG TATACTGGAA ACCTGAGAAT GCCATTGCCG
15101 TTAACAGAGT CCACAATCCC TCACCTCACT GCTTCCTTTC TCTCCTTATC
15151 ACTTACCTAT AAAACTGGAT GGAGAGCTGC AGAAATGAGG ACATTTGCTA
15201 AGAAATTCTT TCTTTTCTAA GTGGTATGTG AAAATAAAGT AAATTCATGT
15251 TGAGTCACAT TAATCTATTG CCTTGGCTGT GTAAGAATCA CCAAGAATTC
15301 TCACAACCTT AGCAACAGTT GCAAAATAGA AATACAACAA AGCAAAGGTG
15351 AGAAAACCAA CCAAGTGTCT GCTTTTTAAA CAATCTATTG ATATAATTCA
```

FIGURE 3D

```
15401 CCACATTAAG ATATTAAGCC AGAAAACCCA TATGCTCATC TTATAGAAAG
15451 CATTTAAAAT CCACACTTAT TCATCATAAA AACTCTTAAC AAAGAGCAAG
15501 GAGTTTTTTA AAACTGATAA AAGACATCTA CCAAAAATCT ACAACAAGCA
15551 TTCTAATGGT AAAATATTTT AAGGTTTTTC TTAAAAATCA GGAATCATGC
15601 ATTTTATCTC CACTTCTATT CAATGTTGTA CTGAAGTCCC AGGCAACACA
15651 GCAAGACAAA AAGGAAGGGG AAAAGGGGCT CTATAAGCAT TGAAATTAAA
15701 GAAGCAGAAC GTATTAAAAG TACATTAAGT ACATTAAAAG TAACGGCAAA
15751 AACCGCAATT ACTTTTGCAC CAACCTAATA GTGTGTGCAG ATGTAATGAT
15801 TACTTGCAAA GAGAAATATC CCCCAAAATA TCTATACCAA AATTATCAAA
15851 ACTACCAAGA GAGCTAAATA GAAAATCAAC ACCAAAAATC ATTTTTATTT
15901 CTATATCTTA GCAAAAAAGA GCTTAGAGGT GGCATGTTAA AAGTTACCAT
15951 TTACTAACGA AAAGGCAAAT TTGTTAGAAG AAAACATAAT TTAAAAATGT
16001 GCAGCCGGGC ACGGTGGCTC ACGCCTGTAA TCCCAGCACT TTGGGAGGCT
16051 GAGGCAGGAG GATCACGAGG TCAGGAGTTC GAGACCAGCC TGACCAACAT
16101 GGTGAAACCC AGTCTCTACT AAAAATACAA AAAATTAGCC AGGTGTGTTG
16151 GTGTGCACCT GTAATCCCAG CTACTCAGGA GGCTTGAGGC AGGAAAATCG
16201 CTTGAACCAG GGACGTGGAG GTTGCAGTGA GCCGAGATGG CGCCACTGCA
16251 CTCCAGTCTG GGCAAAAGAG CGAGACTCCG TCTCAAAAAG AAAAAAAAAA
16301 AAGTGCAACA TCTTTATGGA TAAAATTGTA AAACTTTTGG AAAGGCATTA
16351 AAGAATAGAT AAATGGGCTG TGTGCAGTGG CTCACACCTG TAATCCCAGC
16401 ACTTTGGGAG GCTGAGGCGG GTGGATCACG GGGTCAGGAG TTCGAGACCA
16451 GCCTGACTAA CATGGTGAAA CCACGTCTCT ACTAAAAAAT ACAAAAATTA
16501 GCCAGCCATG GTGGTGTGCA CCTGTAATCC CAGCTACTCA GGAGGCCGAG
16551 TCAGGAGAAT TGCTTGAACC TGGGAGGCGG AGGTTGCCCT GAGCCAAGAT
16601 CGCTCCATTG CACTCCTGCC TGGGTGACAG AGTGAGACTC CATCTCCAAA
16651 AAAAAAAAAA AAAAAGAATA GACAAATAGA CAAATTCACT GTATTTATTA
16701 ATAATGACAC TCAGAATCGT GAGTATATCT GTTCTTTCCA AATTATTAAT
16751 CTATTGATCC AATATAATTC TAATGAAAAT TTCATTTTTT TCATGAAACA
16801 TAACAAGCTG ATTTTTAAAA ATTATGTGAA AAAGCAAAGG ATCAAGACAA
16851 GAGGCTTGTA AAAAAAAAAG AATTGGGCAG GGCAGAGGGG AAGCAAGAGT
16901 TTGTTCTCTA AGATATTAGG ATGTAATATG AAGCTACCAT CACTAAGATG
16951 AGTAGTATTG GCTCAAGGGT AGACAAATAT ATCAATGAAA CATAATAGAG
17001 AACTAAGAAA TAGAGCACAT TATATTAGCA AGGGTAATCC TTGATTATGC
17051 TATAATCACT AATAAAACCT GAAACAGCTT TACTTAATAC AATATAGGGT
17101 TAATTCTGTC TTAGTACGTT TGGGCAGTTA TAACAAAACA TACCTTAAGT
17151 GGTGTAGCTT ATAAACAACA GAAATTTATT CTCACGGTTC TGGAGGCTGG
17201 GAAGTTCATG ACAAAGCACC AGCTAATTCT TGTGTTTGGG GAGGGACTAT
17251 CTTCCGCATA GACAGAACCT TCCCGCTATA TATTCACATG GTGGAAGGGG
17301 GAGGGGATCT CTTTTTTAAG GTCACTAATC CCATTCATGA AGCCTCTCCC
17351 CTTATGACCT AATCACCTCC CAAAACCCTC ATCTCCTAAT ACCTTGGAGG
17401 TTAGGATTTC AACATAGGAA TTTTGGGGGG ACACAAACAT TCAGATCAGA
17451 GCAATTTCTC ACTCATAATA CTAATTGATG AAGGTCATAG AACTCTCCCT
17501 GGTGCTCTCC TTCAACTTGG AGATCTTGGC TGCTTCCATT ATGCAACTCC
17551 ACATTTGAGG CTCTTTGCTT CTGGCCGAGC GATGAGAGGG GGCACGTGCA
17601 CATGAAGACA CACCTACTCT TAGGCACCTA TAACACTCCC ACGCATTCCC
17651 ATTGGCAAAG CTCAGGCACT GGCTCTCAAC ACAACCACAC GGAAGGCTGG
17701 GTAATGAAGT TTTTCTGTCT ATGCAGGAAG AGGCAGTGGT GTTGATGAAC
17751 CAACATTTTC TCTGCCAAAC AGATATGGAA CTTGATATAT GACAAAATTG
17801 ACATAGTGGA TCCCTGGGAA AAATATAGAT GATGTAAAAA ATCATAATAA
17851 TAAACGATGC TAAGAAGAAA AAAAAGAAG TCTATTTCTT CTTTACACTG
17901 CACCCAACCA AATAATTTTC AATTGAATTT AAAATTTAAA TAAGAAGGAC
17951 AGAAGAAGTA TATGAGAATA TCTTTATATC CCAGATATCT AGAAAGACAT
18001 CTTAAACCAC ACAAACCTGG AAGGAAATGA TTAAAAAAAA AAAAGCACAT
18051 CATCAAGAAA GAGAAAAGAC AAATTACAAA CTGCTAGAAG ATATTTGCAA
18101 TACATATAAC TGACAAGAAA TTAGTATTTA GAATATATAA AGAAATTATA
18151 CAAATTAACT ACTACAAAAA TACAAGTAAA TTAGAAAAAA ATGGGCAGTT
18201 GATCTGAATA AACATAACAT ATAAGCAAAA ATATGAATGG CCAATAATCA
18251 AATATAAACA ACTGTACTTC ATTAATAAGT CAGAAAATGA AAATCAAAAT
18301 CACAAGAAAA TTTCATTTCA TAAAAATTTG ATTGCAAAAG TTGAAAAGTC
18351 AGAGAGCATC AGGTATTGGC AAGGAGGAAG AACAACAGGA AATCTTTTCC
18401 ACTGCTACTG ACAATATAAA TTGATACAAA AAACTTGAGG ACTGATATGA
18451 CACTATCCTA TGAAATTAAA ACTGTGCATA TCCCATGAAA TGGCAATTCC
18501 ACTTGTAAGA AAATGCTTTC ATGTGTGAAC TGTGGCTAGC TACTTCAACA
18551 CAGATGATAA TCTTGAGAAT ACAATACTGA ACAAAAGAAA AACAAGATTC
18601 AGAAGAATAC ATATAGTATA CCATTTTTAT AAAGTTGAAT CAGGCAAATC
18651 TAAGGGTATT GTTTCAGAAT TCACACATAC ATGTGTTTAA AAATCCATGC
18701 TATAAAGAAA AACAAGGGAA TGAGCAAAAG TCAAAATTTA AGGTAGAGGA
18751 TACCTCTGGT GATGTGGCAA GGGGGTAGGA CAGAGAGGAG CACACAAGGA
18801 TCTTCAGGAT GTCAAGGAAG CTGGACTTTT TAAGTGGGGT GATGGGTTCA
18851 CAGGCATTCA TTTTTATTGTA TAATTAACTA GGATCAGCAT AAATATTCCC
18901 TTATGCATCA AATATTTAAT TTTTAAATT AAAACACACA TGCACGCACA
18951 AGAAAAAGGA AAGAAGTAAA TACTCTGTAA ACTGACCCCC AGTCAAGAGA
19001 GCTGTTGATT TTGCAATTGC TTAGGAGCAT AAAGACTGAG AGTATATGTT
19051 CTCTTATTAC ACTGAATCTG TAGTAAGATC CTCTGTCCTA ATAACATTTT
19101 AAATTTTGTT TCCCTTTTGC AATTACCTAA AAGCTCCTCA CAGTATAATA
19151 TATTCCATCT TTACTCTTTA TTTAATATCA AAATCCTCTT TTATTTTTTT
19201 CCCCAGTGGC CAAGTTCTAG CTGCTCTTCC TAGAACCTCT AGGCAAGTTC
```

FIGURE 3E

```
19251 AAGTTCTACA GAATCTTACT ACAACATATG AGGTAATTTC TCCCTAATTT
19301 ATGTTTATAT TGGTTTCACT TTGTATAAGC ACTGGGTGTT GAGTTTCCTC
19351 CTGTATGTTG TCTGGCTTAC ATGTATCTGG TATGAACTCT TCTTCTCATA
19401 GTCTTCTCTC CCTTCTCATA ATCACATGAT TTTGTTGGTT CCCCAAATCA
19451 ACACTTCTTC ACTTGTGCTA TTGGCTTTCC AGCCAATTTC ATAATAGTAC
19501 CTTGGGATAT AAAGTGTGCA CTTACAAAGA GGCTACAGTA ACAGAAATTA
19551 AAATATTTAT AAATAAAACC TTACTCATGA AACAATGGTT CTTAACCAAG
19601 GATGCACCAG AAAGACAGAG TACATTTATT AAAATTCTCA CCCAGGCACC
19651 CATCTCGACA TAATGTCTAA GATGTAGAAA ATTGACAAGA ATTACAGAAT
19701 ATTAATGGCA GTGGCGGCCC ATCTAGAGCG GCTGCTGCCA TGCGGGAGGC
19751 ACGGCTGGGG CTGTGTGCTC CACGGAGCCA GCAGAAGCCA GGAGGAGGTA
19801 AAAGTCCCGC CCCCTTCTGT GATGGCAGGG CGGCAGCCTC ATGCTCCCCA
19851 GGCGCAGCTG CAGCTGCCCG CTGCAGCTAC AGACCTGGAC ATCCCTGTGC
19901 TCTTGGGGGC CAGGAGCAGG CAGGAGCCCT GCCCTCCTGG GCGCAGCTGC
19951 AGCTGCCCAG CTGGGGTTGC AGACCCAGGC ATTTCTGCAC TCTCAGTGTT
20001 CTGAGAAGGA CCCTCATTCC CCTACAGGCT CGGAAGTGCC TGCTCCCACT
20051 GTCTGGTCTC TCCGAGTTCC TGGTGCTCAC TCCAATCTTG GAGCAAAATT
20101 GAGGCTGAGC CTAGGTGTTG TCACAACCTG GCTGGCTGTG TGCATGATCA
20151 GAGCGGTACT GACATGCTAG CCCCCTGCTG CCTCAGCCCC CTCTGGACTT
20201 TGGGTACTGA CGAGCACAGG AGGGAAGCCA AGGGGGTGGC TGAGGGCTTC
20251 TCGGCACTGG CCTGCAGGCC CCCTCAGCTG GAAAATCCTG GGTGCCATAA
20301 ATAGCCGTAG GAGGCAGACA GGATCCTAGG CAGAAAAGGG CGGGTCCCTG
20351 GTGAAGCCCC ACCTTCAAGC CCAGGAAGGC TGCCAGTCCC GTGGACCGCA
20401 GTGGGAACTG ACGGTGATTT TTCCGCACCC GCCTATGGCC ACCCATGAAC
20451 CAATCAGCAC TCACTTCCTC CCATCTGAAG CCCATAGAAA TCCCCCGGAT
20501 TCAGCCAGAC TCTTCTGGAG AGACATGGGG AGGACCAGCT GTAGAGAGGA
20551 GCCACCCACT CCAGGGTCTC CTCTCTGCTG AGAACTAACA CTCATCAGGA
20601 CACCCTGGCT GCAGAGAGGA GCTACCCACC GCGAGTCTCC TCTGAGCTGT
20651 TCTATTACTC AGTAAAGCTC CTCTTCACCT TGCTCACCCT CCGCTTGTCC
20701 ACGTACGTCA TTGTTCCCGG GCGCTGAACC TGCCAAATGG TGGAGGTGAA
20751 AGAGCTCTAA CACAAACAGG GCTGAAACAC GCCCCTTGCT TGCCACGTTG
20801 TGGGTGACAA GAAGGAGAGA AGAGCTGCAG CCTTTTGGGG AGCTCAGACC
20851 TAAGAACTCC CCGAGGCAGG ACTATGACAC CCTCTTTAGG GCTCTGTGGT
20901 TCCTGACGTC TCCAAACTTC TGGGTGCCAC CACCTTCCCC GGTGCCAGCC
20951 ATTGAAGCTG CTTGAGGGAC ACCTGGTCCA GCCACAGCCT TGCAGGGAGC
21001 CGAAAGATGC CCACCCTGCC GCAGCCAGCA TGCCTCGCTG TGTGTAGTAG
21051 CTGGACCCCA CACCTGCTCA CTCACACACC CCTCACCGCT CAGCTCGCCC
21101 TTGGCACGAA TGAGACCCAA GCCAGTAGCA CGAGATGAGT GCAGCCTGCC
21151 AGGCCGAGTG GGCTCAGCGG GCCTGAGCAA AGCTTAGGCA AAGGCGCCAC
21201 TGACCACAGA GGTTTCTGCT GGTGAAGCGA CCCCAGGGAT CCTGTAACAA
21251 TATCATGGTA CAAAATTGAT GGCTCCTTGT TTGTTAGTGT TTTCCAAGAA
21301 GCAGAGGTCA AGACTAGACT GGAGGAGCAA GCGATGAGGG GAATGCTGTT
21351 GGAGGATAGA GGCGGGAGCT GGAGAAGGCA GAGAGCATCA TCAGACCATG
21401 TCATAGCTCT GACACCTCTG CAGAAAGGGG AATTTTGTTT GGAGAATCTC
21451 AGACTATAGG GCAGGTCCAA AGAAGGCTGG GCTAGGTCAG TCTCAGTCTG
21501 GCAAGAATGG GCCTGCATTA ACACTTCCAC AGGACTCGGT TACTGGCTGG
21551 ATGCAGCCCT GAGACCACAT GGCCTCAGCT TCTAGTGGGT CACCAGGGCA
21601 GCCACTGAAA ACACCAGCCA ACTGTATTTC TCTCAACCGA AGAGCTAAAT
21651 GGTGCATATT CACGACCACC ACATCATGGT AAAGAGGAAA TACTACAAGA
21701 GGAAGCATCT GAGATTTAGA ATTCTAGTTC TTGTTCTGTC ATTTCTAGGT
21751 GTATGATTTT AGATGTCAGG TATGAACCTT AATTTCTTCA CCTGAACAAT
21801 GCAAATAATA ACACCTGCCT AGTCTATATC AAAGCGTTAT AAATATCAAA
21851 GGAAATGAGT GTGAAAGTGC TTTGAAAAAG TACGTGTAGT GGCTCGTGCC
21901 TGTAATCCCA GCACTTTGGA GGGCCGAGGT GGGCGGATCA CGAGGTCAGG
21951 AGATCGAGAC CATCCTGGCT AACACGGTGA AACCCCGTCT CTACTAAAAA
22001 TACAAAAAAT TAGCCGGGCG TGGTGGCGGG CGCCTGTAGT CCCAGCTACC
22051 CGGGAGGCTG AGGCAGGAGA ATGGCGAGAA CTCGGGAGGC AGAGCTTGCA
22101 GTGAGCCAAG ATCGCGCCAC TGCACTCCAG CCTGGGAGAC AGCCAGACTC
22151 CGTCTCAAAA AAAAAATAAA AAATAAAAAA TAAATAAAATA AATAAATAAA
22201 AAGCACATTA AGAGAGAAAA AATGTAAATC TTATTGGAAG CCTTTTTAAA
22251 AAAAGGAACA ATGACATGAT GATAATTACA AGAACATGAA ATTTTTATTA
22301 AATAAAATCA ATGTTTAATC AACTTTCTTT CTAGAAAAAA TTTTGTTTCC
22351 TTTCAAAATAT CTGATGTACA CATGCAATTT TACAGTTAAG CCATGAATAT
22401 AGTCATTCAT TCATCATTGT CTCATCAAAT ATTTATGGAT TATCTTGTAT
22451 ATTCCAGGCC CTTTTATTTT ATTTTTTTTT AGCAACTAGA GTTATAGAAA
22501 GGAATTTTAA AAAACTCACT GCAAAATAAA TGTTTATATT ACCATGTGTG
22551 TGGATGGGGA CCAGCACCAG GGAGTGTCCT TTTCATACTC CTTATAGATA
22601 AAACTGTCAT GGCTCTAGCT ACAGATGAGA ATGATGTGAA CAACTCTTTT
22651 TTAATTTTAT CAATTTTGCC CCTTAAACTG TAGATTGTTC TCTGGCAGCC
22701 GGTAACAGCT GACCTTATTG TGAAGAAAAA ACAAGTCCAT TTTTTTGTAA
22751 ATGCATCTGA TGTCGACAAT GTGAAAGCCC ATTTAAATGT GGGCGGAATT
22801 CCATGCAGGT AGGCACCGTT CAATACGTAT TGAGTAGTTA TTATAAACAC
22851 TTACTATGCA CTTGACTAGG GTATGGTATA ATTGCTTCCT GGAAAAATAA
22901 AATGTATTAA CCATGGCAGC ATAGAAGTCT CTGACTGGAC CAAATGGACT
22951 GGTGATAAAG CCTAAGGTCC AGCTCTGTGA TCTTGGATAA ATGGTTCAAC
23001 CCCTCATGAC CTCCGTCCCT TATCTAAAAT GCAGGTTAGA CTCAGTGATT
23051 GGTAAAGGCT CTCATAGTTC CTTTTTCTCT GACTCTGTAC CCAGACTCAG
```

FIGURE 3F

```
23101 GGAGCAAAAC TGTCATTTGC CTTGGTAGGC TTTTTGATAT CTCCTGAAAA
23151 AGCAGCTTCG GGAGGGGATT TAGCTTCTGC TAATTCTTCT TCACAAAGAC
23201 AGTGACCATT TCTGAATGTC TGGCTTTAAA AAGTGTAACA GGTGGTTGGA
23251 CTCTGCAGAG ACCTCGGGTT AGTCTGGCAC TGCCCCTTAC CACCTATATG
23301 ACCCTGGGGG AATTATTCAC CTCTCTGCTC CCAAGTTTTG TATATTAAGG
23351 GTAAAAACAG CACCTACCCT GTGGATTAGA AATGATTTCC TTTTCTTAAA
23401 AAGTGTATCA GGTACAATTT CTGCTCACAG TCTAGCCTTC TTCTTATGGA
23451 GTCTCCTAAT ATCTCCCCTC CATATCCACT GCCCAACTGC CAGTACCTTC
23501 CTGGTGGCCT GGCCCCTTGA GACCATGCTC TCTTCTGTGT ATCAATGGGT
23551 GCCCCCTGGA TAATATGCTA TGTTAATTAT TAGTAATATA TTATAGAGTA
23601 TATTATAGGT GTGTACTGTT TTCCAGGAAC TGTGCTGAAC CTTTCTATTA
23651 ATTGACATTG TGTCTATTAA TCTTTATTTA ACCCCGTGAA GTAGATGCAA
23701 CCCCATTATA TAGATGAAAA AATATCCTTA CTTATAAAGG AATTTTTCAG
23751 GGTAAATCAG AAAGAACATG GCAGAGTTAG GAGTCGAACT TAGACCTTTC
23801 TGATGTCAAC ACTGCGGCTT TTATTTATTG GCCTAAATAA AAGTAAAGAA
23851 CCCTTTATTA GTATGATAGC TAACTTTCAA CTTGTCCATC TCAGGCGATA
23901 GAATGCCTGA ATTCAGCTAA AATATTTGCC TGGTTAACAA ATGTGGTGCT
23951 CTGAAGAGAA CTTGAATGAG ATGCCTTTCC TGTACTTCCC TTTTCCTGTT
24001 CTATTTCTTT GGCTCTGCAG AACATCTGAT GCAGGTCAAT GGGGAAAAA
24051 ATAAGAAAAA AAAAAAAAGA AAGAAAGGC TTTTCTGCTT CTTCTTCCTC
24101 TTTAACTGAA AACAGCATAA TACAGTGTTA GTCTGGATTG AACAAAGGTA
24151 CATTAATCCA TATATTCATA TAAAAGACAC TGAAGAATCA CCATTGAGTA
24201 ATGTTGGTAA TGGTGGGAAA CGGTGGTTTT TATGGAGGTC CTGAAAATAT
24251 ACCTAATAGG AGCTACTTTT TCTCTAGTGC CCATGTAGGC TCTACTGAAA
24301 GGGTTTGTCA ACCAGTTTAC CACAAGTCGA GATGTCTTAC TTTTACCTTG
24351 ATGAAATGCT TATGAAGTTT CTTAGTGATT TTTTTTCTTC ATGCTCACCT
24401 GCTGTGCCTG CAATGGGCCA TGTGGGAAGA TCCACCCTCT GCTTGGAAAC
24451 TAGCTCACTC TCTGTTTCAT CACCTAGTGT CTTGCTGGCA GACGTGGAAG
24501 ATCTTATTCA ACAGCAGATT TCCAACGACA CAGTCAGCCC CCGAGCCTCC
24551 GCATCGTACT ATGAACAGTA TCACTCACTA AATGAAGTAA GCCATCACAC
24601 AGCTCTTCAA AGCTACTATT TTCATTTAAC CAGTATTGCC ATTTCAATCA
24651 GGGGAATATT CAAGAATCAT AATTGGTGGA AGATGGTAAA AAATAAAACA
24701 CAAACACACT TAGGTTAATT AAATGGTGGT CATTCATTTT TTGGTAGATC
24751 TCTTCCCTGA GAAGACTGCA TCATATTTGG TAAACTGCAG GATGTTTGTC
24801 TACAGCTAAG AATATCTCTA ACTGCTGGGA ATAACACTTT ATGCTATGGA
24851 ACAACAGAAA TTAAAGAATT GGGGCTTTTA ATTAAAACTG CCACCAAAAA
24901 ATTACCAGTC CAATTAATCA TGTCTCTTTG GACCATTACC CTAATTTTAC
24951 TAATTACCAG ATTAGCTCAC TGAATTAAAG GAATATATTC ACTTATATTT
25001 AATACACTAT AACTAATTGC ATTTTATTCC TTAGAAGGAA GCTATTTAAA
25051 CTAATAATAA TAATAATGCC TTTGTTTTAA TCTGTAAGAA ATTGGATTTT
25101 TTTTCTATCA GTACTTACAG GTTCCACTCC TTCTAGAGAG AACTTGAGTA
25151 AGATGTTGAT GTGCAGGTGA GACCTCAGCA AGCTTTCACA TAATCCACTA
25201 AAAGCCATTC CCTGTATTTG TTAGTTGAAA GAATAAATTC GCAGGAGGAC
25251 TTTCTTTTTT ATATGATATT CTCCAAGTAG TAAAAATACC TTGATGCCTT
25301 TTTATGAGTA TGCAGCTATA TTGCCTAATA TAACTATTTT TGTCATCTTT
25351 GACTAAGTGC CCAGAAACTA TTAGGGACCA TATCCATATT TTTAAGACAT
25401 CTAAGACTTA GGTAATGAGA ATCAATTTTA TGTATATAAT CTTTAAAAGC
25451 ATCTGTTCCT TCCCAGTTAA TTAAGCCAGA GTCAGTATGC TTCTAGAATG
25501 TGTGCCTGGT TGATTGAGGG GGCCTTAAAA TTGCACCCCC CCTTTTTTAA
25551 TCTCTCCTAC ATCTATCCAA CTTAGACCAC CTCTCTCCAG CATCCATCAG
25601 CACGACTGCA TGAGCAAACT TGATGCAGAG AGGCTTCATA GGTGGGATTT
25651 CACCTTCATA GAAGGTGAAA CTGTCACTGC TGTGATAAGT TTGGTGGGGA
25701 GAGGGGAATG CCGTAAACAG AAGTATTTTT AAATATTTGT TAAAACATAT
25751 TTTAATTATT TTGTTCAAAA AAGTTATGTT TTCTTACGAT ATGTTCAGGA
25801 AAGAGTTGGA ATGACACAGG AGGAAAAAAT AAGCACATGG CTCTATTAGT
25851 TTTCTAGGGC TGTGGTAATA AAATACCACA GACTGTGTAG CTGAAATCAC
25901 AGAAATTTGT TTTCTCATGA TTCTAGAGGC TAGAAGATCA AGGTGTCAGT
25951 AGGTTTGGTT TCTACTGAGG CCTCTTTCCT CAGCTTGTAG GTAGTTGCCA
26001 TCTCACAGCG TTCTTCCTCA TATGCCTTTT CTTTCCTTTT TTTTTTTTTT
26051 TTTTTTGAGA CAGAGTTTCT CTCTGTCACC CAGGCTGGAG TGCGATAGCA
26101 TGATTTTGGC TCACTGCAAC CTGCGCCTCT TGGGTTCAAG CAATTCTCCT
26151 GCCTCAGCCT CCAGAGTAGC TGGGACTAGA GGCGCATACC ACCACGCTCA
26201 GCTAATTTTT TGTATTTTTA GTAGAGATGG GATTTCACCA TGTTGGACAG
26251 GCTGGTCTTG AATTCCTGAG CTCAAGTGAT CTGCTCGCCT TGGCCTCCCA
26301 AAATTCTAGG ATTACAGGCG TGAGCCACCA TGCCCAGCCT CATATGACCT
26351 TTTGTTTGTG CACATGCATC CCTGGTCTCT CTCTGTATAT CTTAATCTCC
26401 TCTTCATATA AGGACACCAG TCAGATTGGA TTCGTGCCCA CTCTAAGGGC
26451 CTCATGTTGA CTTGATCATC TCTTTAAAGG CCCTATCTCC AAATACAGTC
26501 ACTTTCTAAC CTACTGGGTA TTAGGGATTG AACATATGAA TTGGAGAAAG
26551 GGGTACAACA TCTACTCCTT AACTATGACA TTATAGAAAA TGTCTTGTGC
26601 TTCTCTTTGC ACCCCCGCCC CTATTATTTT CTAACAGGTT CATAGGAACC
26651 ATAAGCATTT TGCTCTCAGA ATATTCCTCT AAGTGCTTCT TTCCCTTTGA
26701 TCGGTGGTCT CTTGATCAGC CCTACCTACA AGATGGACTG GTGGGCAGCA
26751 GGGTTATTT TGTCATTGAC TCACACCAGG AGATCTTAAA TGATCCGGTG
26801 TAGGGAGAAA GAAACAAATG GCCAAAAATT ACTTCTTAGA AGAAATGGTG
26851 AGAGAAAAGA GTTCTTCAAA GGATGTTACA TTATTACCCC AGCTTAGTTT
26901 GAGAAATGAA TAAAGTCTGT CGGTTAAACT GCCTTCATAT TATACAGCCT
```

FIGURE 3G

```
26951 CTCCTGTTAG AGGAAATCTA CTGAAGTATC AATGCATAAA TTATTTTTTT
27001 GTGGTAGCTT TCTCAGATGT ATTTATGCCT AGAAGAGTAA CACAGGAAAT
27051 GGAGATTCAA TTAGGAAATT GCTGACAGTT ACATTTCTGA CACCCCAGAC
27101 ACTGACAGGG TCGGTACTTG GTGGCAGGAG GGCAGGAGCC CTTAATTCTC
27151 AGCATGGGGA CAACCACTCA CACCTACCAC TCATGCTGGT TATGTGATCT
27201 CAGAGAACCC AAGGATAAAT GGTGCTCCAG TTTTTACCAG CTAGGATTGC
27251 TATTTGAAAT CACCTCTAGA AAAGTTCCCA GAGATAAAGC CAGGGTTTGA
27301 TTGCTTCTGT TTCAGAAGGC ATCAGAGTTT AAGAATGGAC CCTGGAAAGT
27351 TGGTCCAAAT TAAAACATAA CCCAGTTCAA TCCCAGCAAT CCCAAACCAG
27401 ACAATAATTC AATGTTTGCT TTGAAGTGGG TGCTAGCCTA AAGTCAGAAT
27451 TTTTTTCTTT TCTTTTCTTT TCTTTTCTTT TTTTTTTTTT TTTTTGCTTT
27501 TTCCTTCCCC TATTATCTTG ACAGAACCTC AAATACAACT GGACTTCCAC
27551 CCAAGAGAGA GGTCCAGAAT CGAACTACTT CTTGGGGGGA TAATTGAGTT
27601 TGTTTGTTTT TCCTCCAGAT GGTCCCCACC TTTGCCTCTC ATCATTGTGC
27651 CAATCTCACT GTGCTTGCAC AGGTCTTTAG TGGGAAACAA TGATGCTTCC
27701 ATTTATCCTG CATGAAGACA GTGCTAAGGG CTCCCTTCAT CTTGAAAAGT
27751 GCATTTTTAA AAAAGTCTCA TATAAAAGTG AACTTTTGAA TGAATGAGAA
27801 CAAGAATTTC ATACACAGGG GCAGTGACTC AATGTGATGA CTTTAAAAGT
27851 AACTTTCAGG GGCCATAGTT TATAGATTAA CTTTTCCTAC CTCATTATAA
27901 GTATCTTAGC ACTTTTTCAC TCTTTCTCAA AACCTTGACA CTTATCAAAA
27951 CTTTAATTTT ATTAATTTCC CTAAACAGCA GAAGAAACAC CCTGCCCTAA
28001 GTGCTTTAGG TCCTCGTGCA TTCCACATAC AGAGGTTTTC CTTTCTCTGA
28051 AGAAGTTGTC TGCTTGCTTT GGTCAGGGAA ATGCTTTGAA CTTGGCTTCG
28101 TGACTAACCT CTGGTTTCCA TTTTGCTAGA TCTATTCTTG GATAGAATTT
28151 ATAACTGAGA GGCATCCTGA TATGCTTACA AAAATCCACA TTGGATCCTC
28201 ATTTGAGAAG TACCCACTCT ATGTTTTAAA GGTATGTTGT GGGGAAAGTT
28251 GTTGATCTTT CACTGTGAGG GGAGGGATTA ATTCTCCAGT CGTGTTTGTT
28301 AAAACTTGAG TTTGTTTCCT TTGAGTTCTG AAAATATTTG CATTACAAGT
28351 GTTCCTCAAC TTTAATACCT GGCTATTTAG GGGTTGGTTA TTTTTCCCAT
28401 TAATAATATA GTCTTGTCCT GGTCTGTATG TCCTAATCTC CTCCCACAAG
28451 GACACCAGTC AGTCTGGATT AGTACACACC CTAAGGGCCT CATGTTAACT
28501 TAATCACCTC TTTAAAGGCC CTATCTCCAA ATACAGTCTC TAGGGGGTTA
28551 AGGCTTCAAT TCTAGATGAA TCCCAGTTCT AGAATTAACT CTGTTTCTGT
28601 TTATGTGACA TTAGATAAGC CATTTAACAT TTCCATAAAA TGAAGGAAGT
28651 GGTGTTTATT TTTTTCAAGT CCTTGTTTTA TTTTCGTTAG TGGACAAACA
28701 CTATTTCTGT TAGGGGACAA ACACTAACAG AAAATAAAAC AGGGACTTGA
28751 AAAAATAAAA TTAAAAATTA AAAAAGTGG TGCAGCTTTT TGATGTTAAT
28801 TTTTAAAAAT TGATACATAA TAATTGTACA TGTTTCTGGG GTACATGTGA
28851 TTTTTTTTCT CCCTCCCTCC TCACATGTGA TGTTTTGATA CATGCATACA
28901 ATGTGTAAAT CAGGGTATTT GGGATATCCA TCACTTCAAA CATTTATCAT
28951 TTCTTTGTGT TGGGAACATT TTAAGTTCAT CTTCTAGCTA TTTTGAAATA
29001 TTGTTGATTC TCGTCACCCT ACTGTGCTAC TACACACTAG AACTTATTCC
29051 TTCTATCTAT TTTGTACCCA CTAATTAATC TCTCTTTATC CTCCTTTCCC
29101 AGCCTCTGGT AATCACCATT CTACTCTCTA CCTCTATGAG ATCAACGTTT
29151 TCCACTCCCC ATATCAGTGA GAACATGTAG TATTTGTCTT TCCCTACATA
29201 GCTTATTTCA GGGCATGTTG CTGCAAATGA TAGGATTTTA TTCCTTTTAA
29251 TGCCTGAGTA ATATTCCATT TGTTATCCAC ATTTTCCACA TGCATATCCA
29301 CATTTTCTTT ATCCACATCC ACATTTTCTT TATCCATTCA TCTGTTGAAG
29351 AACACTTAGG TTGATTCTAT ATCTTGACTA TTGTGAATGG TGCTGTAATA
29401 AACATGGGAG TGCAGGTATC TTTTTGATAT ACTGATTTCC TTTCTTTTGG
29451 ATACATACCC AATAATAGGA CTGCTGGCTT ATATGGTAGT TCCATTTTTA
29501 GTTTTTTGAG GAACCTCCAC ATGGTTTTTC ATAGTGGCTG AACTAATTTA
29551 CATTCCTACC AACAGTGTAC AAGGGTTCCC CTTTCTCCAC ATCCTCTCTA
29601 GCATTCGTAA TTGCCTGTCT TTTGGATAAA AGCCATTTTA ACTGGAATGA
29651 GATGACATTG CATTGTGGTT TTAATTCACA TTTCCCTGAT GATTAGTGAT
29701 GTTGAGGATT TTTTCATATA CCTGTTGCCC ATTTGTGTGT CTTCTTTTGA
29751 GAAATGTCTG TTCAGATTCC TTTCTCATTT TTAAAATTGG ATTATTTGTT
29801 TTTTTCCTTT TGAATTGTTT GCGTTCCTTA TATATTCTGG TTATTAAGTC
29851 CCTGTTGGCT GGATAGCTTG CACATATTTT CTCCCATTTT TTTCTTTTCA
29901 CGCTGTTATT TCCTTTGCTG TGCAGAAGCA AATTTTCAGT TTGATGTAAT
29951 CCCCTTTATC TATTTTTGCT TCTGTTGACT GTGCTTTTGA GATCTTACCC
30001 AAAAAATCTT TGCTGAGACC AAAGTCCTGA ATTGTTTTCC CAATGTTTTC
30051 TTCTAGTAGT TTTATAGTTT TAGGTATTAC ATTTAATTCT AATCTGTTTT
30101 TAGTTGATTT TATATATAAG GCGAGAGATA GGCATTTAGT TTGAATTTTA
30151 TGAATAAAAT TTTTCCCAAT ACCATTTATT GACAAGACTG TCCTTTTCCC
30201 AATGTATGTT CTTGGTGCCT TTGTTGAAAA TGAGTTAACT GTAGATCTGT
30251 GGATTTATTT CTGGGTTCTC TATTCTAATC CATTGGTCCA TGTGTCTGTT
30301 TTTATGCCAG TACCATGCTG TTTTAGTACT CCAGCTTTGC TCATTCTGTT
30351 CAGCATTGCT TTGGATTTTC AAGATCTCTT ATGGCTCCAT ATGAATTTTA
30401 GAATTTTTTT TCTCTTTCTA TGAAGAGTAT ATTGATATTG ACAGGGATTG
30451 CATTGAATCT GTAGATTCCA TTCGGTAGTA TGGACATTTT AACAATATTA
30501 ATTCTTAAGC CCGTGAGCAT GAGGTATCTT TTCATTTTTT TGTGTGTTCT
30551 CTTCAGTTTC TTTCATCAGT GTTCTATGGT CTTAATTGTA GGTCTTTCAC
30601 TTCTTTGGTT AGATTTATTA CAGGTTTTTT TTTTTTGGTC ATTGTAAATG
30651 GTATTTCTTT CTTGATTTTT GTCTGCTATT GTTGTATATA
30701 AATGCTACTG ATTTTGTGTG CTGATTTTAT AACCTGCAAT TTACTGAATT
30751 TATCAGTTCT AACACAGTTT TTTGGTGGAG GCTAGGTTTT TCTAAATATA
```

FIGURE 3H

```
30801 AGATCGTGTC ATCTAAAACC AAGGATAATT TGATTTTTCC CTTCCAATTT
30851 AGATGCCTTT TATTTCTTTC TCTTACCTGT TTGCTCTGGT TAGTACTTCC
30901 TGGTACAGCT TTTGAAACTA AAGTAAGACC AGGACAACAA ATCCCAGCGA
30951 GGGACAAACA GCCGGACAAG GCTGAAGTCC TTTGCAGTAG GGTTCTTATG
31001 ATGGTTTCTA CTCCAATTTC CACCCATTTG GTTATTTATT TTCAGTCGCA
31051 AAATATTATG CAAGAGAAAT TGATTAACCT AACTTGGATT GGATGTCTTC
31101 TCTCTTGAAT AAATTGACCT TAGTAAAGGT CAGTGAACAT AGCCACAGCC
31151 AATTGTTTTC AGAACTAGGA AACAACTCTA TAGTTCTGTT TTCTACCTCT
31201 CTCTCTTAAA AAAAATTTTT TTTAAAGCTC TGGAAAATAA TGTAGTCACT
31251 AAAAATGTAC ATTTAATTTA GTAACATATA ATTTATGCAC AGTATCCCAA
31301 TATTATCTAA ATTGTGATAG GTGAGCCTCT TCAGTCATTC AAAGATAAGA
31351 CTTTGGGTTA GGACTTCTCA ATTTTAATCT GTCGTTTACA AGAACTTACA
31401 GTGCAGACTC AAGGCAGACA TATGAAATGT TGGGTCCCCT TGGTTATTGA
31451 GTTGGTCAAT CAGATTGGAT CCATGTATCA TGGCATATCC ACCCATGACA
31501 TTTGCTTTCA GCCATGTTGT GTGTAGTCCT TGGAACATAC TTATCTGGAA
31551 CCTGTACACG TTGAAAAATC ATGCATTCTG GATGGTTTGG TCCTACTCTT
31601 ACTTGATCAA GGATGTGCAG ATAATGTGAG TCTCTGGGAT TTTGCCAACT
31651 TTTCGGTGTC AGAACCAGTG CCAAGAAAAT TGGCCCAGGA CTTAGAAAGG
31701 TCAAGTAAAG TAATGAATCC AGACAACTTA AGATTTTCTT TGCATTGAGT
31751 AGATTAAGCT AGGTAGTTCT CTTTGACTAT ACAATTTGAC GATTAGTGGC
31801 CAATGCCATT GGGCTTTCTC ACTTACTATC CTGTTAAATA TTGCTAGCTC
31851 CAAGTTAGGA AAAAACCTCC TGGAGTGGTT CAAATGACAA TCTAAATATC
31901 TAACTCTTTC TTTTTCTTAT TTTGGAATTG CAAGTCTACA TATTTGTTTG
31951 ATTTTACAAC AGTCTTCTCC CTTCCCTCTA TACCAGTGGT CCTCAACCCC
32001 TGGGCTGCAG ACAGGTACCA GTCCATGGCC TGTTAGGAAC GAGGCCACGC
32051 AACTGGAGAT GAATAGCCAG CGAGCAAGCA TTACTGCCTG AGCAATGCTT
32101 CCTGTCAGAT CAGTGGCAGC GTTAGATTCT CATAGGAGCA CAAACCCCAC
32151 TGTGAACCGC GCATGCAAAG GATTTAGGTT GCATGCTCCT TATGAGAATC
32201 TAATGCCTGA TGATCTGAGG TGGAACAGTT TTATCCCCAA ACCATCCCCA
32251 CCACTGATTC CACCCCAACT CTGCCCCATC CATGGAAAAA TTGTCTTCCA
32301 TGAAACTGGT CCCTGGTGCC AAAAAGGTTG GGGACCACTG CTCTATACCC
32351 TAAACTGTGT TGTAGCTGAC TTTTAAAGGC AAATACATTA TGATTAATTT
32401 TGGAGGTGTT CTTGATAATT CTTCTAAAGA CATCAAAGGC TATTATTGAG
32451 AAAAGGTTGA TGATTCTTAT TCCAGAGTTA GCAGCTTGTG TTAGCCCACC
32501 ATACTGGGAA AAAAGCCTCT GTCCCTGGAT TTGCTGGTAA GTTCGTGAGA
32551 GGTTAGATGT ATGCTTCTTT TTGTGTGAAA TAAAGAAATA ATCCACATAA
32601 AAAAATATGC ACTCAGGAAA ATCTTGAGGG AGTTTTTGCT CCGGGTGTGT
32651 CTCCACACCT CCCGGGGAAG ATTGCCATCC AACTCACACC CATTTACCTC
32701 TAAATGAAGC ATGAAGATAC AGCCCAAATC ATTAGTTCTC TGGTCTCTTC
32751 TTTGAAACTT CCACATGCAG CTCTGACATG ACTGCATAAT TGTGGAGGAT
32801 AAAAACAGTT TTAAATCAAA GAGTCCTGGC TTCAAACTTC AGTTTCAATT
32851 CACACCAGCT TTGCTACCTT AACTAATGTC ACTTAGTATC ACCAGTGTTT
32901 AAATTTCCCT TGAGAATTTT CAAAGAAATG CAGAACAATG CATATCTCAG
32951 AGATTTGCTG AAACTATTAA ATATAAGCAC TATATAAATG AAAGTTATTA
33001 TCCTGAAGCT TATTGTTACT GTTTTTGCTA CTTTTGGGGT TTCTTTGAGC
33051 AGGTTTCTGG AAAAGAACAA GCAGCCAAAA ATGCCATATG GATTGACTGT
33101 GGAATCCATG CCAGAGAATG GATCTCTCCT GCTTTCTGCT TGTGGTTCAT
33151 AGGCCATGTA AGTATTCACA TTCTCTTAAC CCTATTTCTC AAAATGGTGC
33201 CCAAGATCAC CTGTGTCAGA CTCAACTGGG CTATTTATTA AAATGCATTT
33251 TCCTAGGTCA CATCATGAAG CTTGGGAATC TACAATTTTC ACAAGTTTCC
33301 CAGGTGACTT TTATGCATTA GTAAGTTGAA GAACATGACT TCAAGCATTT
33351 AAATCACCCA AAATATTTTT GGTCTTTTCT ACATTAAAAA AAAAAAAAAA
33401 AAAAAAAAAA AAAAAAAAGA AATAGTACAT TGATTATAAT ATGTTTACTA
33451 AGTAGAGGAA AGGACTGAAG GAGTTATCTA AGTTGGGGCC CAATTAATTT
33501 ATTTCTCTTT TGGTTTTAAT TATCCAGACA TCTTTTGCCA CCTTTGCCCT
33551 TGGAAATTGA ACATAAAGCA CAACATTACA GAGGTGAAAC AGAATATGTT
33601 TTCTCATATG TCATAATAGG GAATTTTCTT CCTGAAGAAG GGTTTTGCAT
33651 CAAAAAAGCC ATATATAAGA CAAACTGTAT GTTGGAAAAG TAAAAGATAT
33701 AACGACTATT AACCTCCCTG ATGAATGAAA ACAGTAAAAA TTATGCTTCA
33751 AATCCTATAA AATGGGCATA TATGTTCTCT ACACTGATTT CTACAAAGAA
33801 TCATAGCCAC TGGAAAAATA ACTCAAAATA TGTGTCTTTC TGATAATGAT
33851 TTTTGCAGTC TTTGCATTCA CAGATACATA GTAACAGAAT AAATGAGTTA
33901 GGAAATTAAG ATATTGGCAC TTATTAAGTA CATCAAGATA AAACTGTTTC
33951 TGTCTTTGCT TGACCTTCA AAATGCAACA TCCCTATTTG CCTTCATTCA
34001 CTGTGAATCT TCTATCCTCA ATTCTCCATG GATGGGAGCT GCAACCTCCC
34051 TGAGTCTACT GGAAATTCCC AAACACCATT GGTACTACCT TGGCCAAATG
34101 AGGATGATTC CAACTGATCA GACCCTTAAC ATATCCCAGT CACATCATGA
34151 TCTGGAACCT TCCCCAAGTT GAGTAGTTTG GTTATTTTAG GTAGTGAAGG
34201 GAGCAGCAGT TAATAGAGAA AGGTCCAAAG TAGGAGAGTA AGAACATTTA
34251 TTTTCCATTC TATCACTGAA CATGAGAAGG GCCAAGAAGA AACCTCCATT
34301 CATATTGACT CTAATTTATA TCGGTGAGGT TGTCCCTAAT GACTGCCCTT
34351 CTCACCCTGA CACCTCTGCC CTCCTATTAG ACATCCTACC CTCTACCCAA
34401 ACTGCTTGCT GAATCTTTGT AAGATTAAAT TATTTAATCC ACAAATATTT
34451 ATAAATTGCC TATGATGTTT CAGATCCTGG AAATACAAGG ATGAACAAAA
34501 TATAGCCCAA GGATCTTATA GCTGAGTATT TTGCTCCAAC AATGTGAACC
34551 TGATTTGTGT AGCCCAAAGA AACATAATCA ATAAGGGCTT TTTAAATCGA
34601 CATTTAAACT CCATTCTTGC CTGCCTAAAA CTAATTCAGA TCATCTGACT
```

FIGURE 3I

```
34651 CTCTTAGTAC TTCAAAGCAC TGGAGGAGGG AAAGTAAAAT AAAATATTTA
34701 CCTTTCAACA ATTGTGAAGG CAGGTTTTAT ATTCAAAAAC TAAACCACCC
34751 AAAGGCAAAT TAAAATCTTA GCTTTTAAGT CTCTCACTCT TTTCTACAAC
34801 TCAATAAGGA TTTCAAAAAT CTTATAATCT AGTCTCAGTG GAAATCCACT
34851 ACACTACACT TTGAGAAGCT TGAAGCCAGT CATTTCTTTC TAAGCTTCTC
34901 ATTCATGTAC TCTCGGGAGG CAAATTTAGA TCCTTCTCTT TCCGCAAAGG
34951 CAGAGCTGAG ACCAATTTGT GCATGACTGC ATCACCAAGC CAAAATCCGG
35001 CACAGGGCTG GCACATCATA GGACCCAGTG AATATATGTT AACCATCACA
35051 ACTTGCCAAG TACTTTTTCT GCCAAATGGC TTTTCTCACT GCTAACCTCC
35101 TGCCAAACCT CTGCCCTAGA AAACTCTCAT CTAATTGCAC ACAAAGTTAG
35151 AGCTCTACAA CCTCAGGGCC TTCACAGAAT TATCTCTGCC CCTCCTCACC
35201 ACAGCTGACA CATGACCTAA GGACACTGCT CCCTGGTGGC TCCTTCAAGT
35251 AGAGGGGCTG CTCTTTTTTT CACATCACCA TGTGCTGAGA GGCCTGGTGG
35301 AGTGGATCAG CATTCTCTTC TCCTGATACT ACCAATGATC CTTCTCTTCT
35351 CAGAAACTTA CACAAACTGG TTGCACTCTT ATTTTATTGC TATCGTGCAC
35401 TGACCTTCAG ATAATTTCCT GGTATCCGGT TCATGATTCT TTATTCCCCT
35451 CCAACTCTTG CCATCATTCT GAGTGAATTC AAAGTCCATG TGTGAGAGTC
35501 ACCTAACAAT GTATCTTCAC AGTTCCTTGT TCTCTGTTCT ACTAAACCTC
35551 ATCTCAACTC CTCTTTAGCA GATTTCTCCT GTAGCCATCC TCTGGATCTC
35601 AGAAGTAATG TTTTGCTGAT CCTTAGACCC AGAATGTGGC CATGGACAGC
35651 AACAAGGAAT GTTAGAAGAA GCCATCTAGC AATGTAACTT CTTAATTTCC
35701 TGTCTTCTCT CATTTCTCAC CCCTACTATG ACTGCTTTTT TTTCAACCTT
35751 AGCATATTTC TAGTTCCTAC ACAGATCTAT ATCATTTTAA TTTATCAGTC
35801 CCTTTCCAGG AACACTTTCT TCACTAATTG GTCCCATCAC AAATTCATCC
35851 GAACCCTCAA TTTCTTGCTC CCTTGACCTG CTCTTCTGGA GTTCCAACCC
35901 CAAACACTCC ACAGAATTAA CCATCCTTTT TCTGAGCCAC CTTGTACATC
35951 TTGCCATTGT TTATTATCAT ACTTATATTA ATAGCATTGA ACTGCTGCTT
36001 TTCCCTTTCC AACTTATCAC TTCTATTAGC TTTCTGAAGG CAGAGACCAA
36051 GTCTAAAGTA ATTTTTTTGT TCCCCATAAC CTGGTATATT GTTTGGTCAA
36101 CATAATTGGT GCTCAATATC CCTTGTGGA ATTTGAAATT TAAATTAATG
36151 TTGCAGGTTT AGGCTGACAT ACAATTTTGG GTTGCAGAGA GTATCTAAAC
36201 AGTACCTACT GTTGGGATAA ATACTTTATT GTCATTGGCT ACAGTTCAAA
36251 CTATACATAC ATATATAGAG ATTGGAGTAA AAACTGAGAC AGATAGCTCT
36301 CTGATATATT TGTAATGGTA ATGAAAATGA CATTTTGTTT TAAAATTTTC
36351 CCTTCATGTG TCTTATATTT TTTTTTAGCA ACCCCATTAA CTGACCTATA
36401 TGTCGTTATG TACTAATTTA TTATCTCTCA AATGGTCATT GGTTAATTCC
36451 TAGGCAGGAA TTGTTGTTGT TGTTGTTGTT GTTTAGGGCC ACATTAAAGG
36501 CAAAGCTTGA GTGCACCCCA GGCAAAGTGA GAGGAAGAGC TGAGTAATCA
36551 TTGACCACAG GCCAGCTGAT GGGAATCAAT CCCACCCTCT CATCACTCAG
36601 TCTTACACTC TTCTCCATTC TCCTCTATTC TCATCTTCTT TTTCTTTTAT
36651 ACAGAGGCTT CTCAATTTAT GGTGGGGTTA TGTCTCAATA TACCCAATAA
36701 ACAATCACAA CTGAAAATAT TCTAAGTAAA AAATGCATTT AATATACCTA
36751 ATCTACCGAG TACTGAATAT CATAGCCTAA CCTTCCTTAA ATGTGCTCAG
36801 AACACTTACG TTAGCCTACA GTAGGGCAAA ATCTTCTAAC ACAGAGCCTA
36851 ATTTATAATA AATTGCTGAA TATCCATATC ACTTATTAAA TACTGCACTA
36901 AAACTGAAAA ATGGAATGGT GGCATGGGTA TGGTTTCTAC TGAATATGCA
36951 TTGCTTTTGC GCTATTGTAA AGTCAAAAAA TCATAAGTGA AATCATTGTA
37001 TATTGCAGAC CATCTCTAGT AGGACAGGAT TTCAATTATG TTACTTGCCA
37051 TGTTGGTAAA TCGTACCTTC AACAAATATT TATTTGTCGT CAGGCAAAAT
37101 TTCTTCAGCC ACTTTGAAAA ACAATGTGGA AGTTCCTCAA AAGATTAAGT
37151 ATAGAGTTAC CATATGACCC AGCAGTTCTA CTCCTAGGTG TATACCCAAG
37201 ACAAGTGAAC ACATATGTTG ACAAATGATT ATAGCAATAT TATTTCATAAT
37251 AGTCAAAAAG TGGAAACAAC TCAAATTTCC ATCAACTTAT GAGCAGAAAA
37301 ACAAAATGCA GCATATTCAT GCAATGAAAC ATCAATCAGC AATCAAAAGG
37351 AATGAAGTAC TGATTCATGC TACAACATAG ATGAATCTTG AAAATACTAT
37401 GCTAAGTAAA AGAAACCAGA TACAAAATGC CACATATATT ATTCCATTTA
37451 TATGAAATGT CCAGAATGGG CAAATCCACA GAGACAGAAA GTTCATTAGT
37501 GATTGTCAGA GGCTTGGGGA AATGGCAGGA GGGAAAGGGG AGTGAGTTAT
37551 AATGGGCACA GGCATGGGGA TTTTTTATGA TGAAATGTTC CAAAAATCAG
37601 ATACTAGTGA TGGTTGCAAA ACTCTATGAA TACACCAAAA ACCGCTGAAT
37651 TTCACACTTT AAAATGGTGA ATTTCTGGAA TGTAAATTAT ATCTCAATAA
37701 GCTGTTAAAG AAAAAATGGG CACCCCTTCC TTCGGGATTG TAGCTATAGC
37751 CACACTTGAA GGTGTGGCTT GGCACACAGC ACAGACTGTA TTTCAGCCCT
37801 CACTCACTCC TTCTGTCTGG AGTCCTACCT ATTAGATAAA GAAATAGGTA
37851 ACATTGTTCT GGGCCTAACA TCGGTAATCT CTCAGAGCAT AACTTTTTGT
37901 AGAAAGATTC CCATCCAACC AGAGGTAAAT GTAGGAAGGA AATTTAAAAA
37951 GTGAAGCAGA AAAAGAAATT CATATGCTGC ATCTATTAAA AGTTTGGCCC
38001 ATGTTGTAGA AATGAAAATG AGAAATGCTT TATTATTTGC TTTATTATTT
38051 TAAAAGGAAC AGGCTCTCCT AATATTTTTC TAATAATGAA TGCTACATTA
38101 TTACTGAAAA GTGATGCTAA CATAAATTTA TAAATTCGTA GCATAAAAAT
38151 GTATTTAACT GGTTGCTCGA CTGTTTAAAA CATGGCTTCC CTGGAAACCA
38201 TCATTCTCAG CAAACTAACA CAAGAGCAAA AAACCAAACA CCACATGTTC
38251 TCACTCATAA GTGGGAGCTG AACAATGAGA ACACATGGAC ACAGGGAGGG
38301 GAACATCACA CACCGGGGCC TGTCGGGGGT GGGGGGCTAG GGGAGGGAGA
38351 GCATTAGGAG AAATACCTAA TGTAGATGAC GGGTTGATGG GTGCAGCTAA
38401 CCACCGTGGC ACGTGTATAA CTATGTAACA AACCTGCATG TTCTGCACAT
38451 GTATCCCAGA ACTTAAAGTA TAATAAAAAA CAAACAAACA AAAAACAAA
```

FIGURE 3J

```
38501 ACATGGCTTC CTTCATTCTA CAAATTTTGC TTCCTTTTCA TTAACCTTTT
38551 ATTTCTGACC TACAGTAGAT TTTAAAATAA CTTTTTTCTT TTCTTTCTCT
38601 CCGATTTCAT AAGTATTTAT TCATGGCAAA GATTTTTAAT GTGACTCTTG
38651 TGATTGTTCT AGGGAAATAT GAATATAATA TTTTAAACGT TTAAAGGGAA
38701 AATAGTAAAG TTTATAAAAG GCTTGTTTTT ATTTTGTCAA TAATGAAAAA
38751 GACATTTCTT AACAATGTCA TGAGTATGCT TTAAGGCAAC AAACAATTAT
38801 AAACTAAATT AAATATTTAA TGTAATTAAA TGTGAATTAA ATTAAAATAT
38851 AGCAATGTTG CCACAAATTA AGATTTTGAA CCAAAAGCTT TGTCCTAGAT
38901 GAAACGATTT GACCAGCTAA AATTTGTCTT TATAGTTCTC CTGCCTGTAC
38951 ATTTTGTCAT TTTGGGGTAA ACTTCTCAGT CACCAAATTT GGATGCCATT
39001 GGATCACACT GCAATATGTG CCACTAAGCT GGATGACTCT AAAGTAGAGA
39051 GGAACAAGTT TGAGATGATG TCCGTTAGGA ATTCATAGCC AGTTCCTAGG
39101 AAAAGCTACC CTAATTCTAC AGCTAGATGA TCAAAGCCTT GGGAAACACA
39151 CTCAATTCTA GCAAAACTTG AGCTCCACAA GTTCTAAGGA CAATGTAGCC
39201 AATATCATGT AATCACATCT GGGGATAAAA CATGGTAGGT AGTTTAAGCT
39251 CTGATGAACA TGAATTACAG AAAAAGGAGC TAAACTAAAT CTAGGTTTTT
39301 GTTTCCTTAA ATCTTCTTAG TGGGCTCTAT GGCTTTAATA AAGAATTAAT
39351 TTTATTTTTT AAGGAAAATT TAGAAAGTTT ATGGTTCGAT TGTCTGCCTT
39401 CATTAACTAG GAATACTGGA CCACGTGTAA GGCATTTATC ACCACTTCGT
39451 AGCACCCTAA GTTCAGTTCT TTTGAGGAAT TAGCACTCTT TCTGAAAGTT
39501 AAATCTGCAA ATCTAAACAT GCCAAATGAC AAATTAAAAA AAAGAAAAAG
39551 AAACACACTA AGTTTAGAAG AACTTAAAAC ATCTAATTAA ATATACTTGG
39601 TTTAATTTGC AGATAACTCA ATTCTATGGG ATAATAGGGC AATATACCAA
39651 TCTCCTGAGG CTTGTGGATT TCTATGTTAT GCCGGTGGTT AATGTGGATG
39701 GTTATGACTA CTCATGGAAA AAGGTAGGAG AAAAGGCAAA GAAGACAAAT
39751 CATGTTCTCC TTGGGGATAT AGGATATACA GGTTGAATTA TTCATAGAAT
39801 TCTGGATCTA GGCACAATGG CTTTATTATT AATTTTTTTT TAACTTTTAT
39851 TGTGGAAAAT GTCAAATATA TATATAAGTG CACATAATTG TGTAGTAAAC
39901 TTCTATCTAC CCATCATAGA GCTTCAACAA TAATTAACTC ATGACCAGTC
39951 TTGTTTCATC TGTATTCTCT CTACCCACTT CTACCTTACT CATTTTATTT
40001 TGAAGTAAAT CCTAGGTACC ATATCACTTC ATCAATAAAT ATTTCAGTAT
40051 GCATTTCTAA AAAAAAAAGA ACTCTGAAAA AAATAATTAT AGTATAATTA
40101 TACCTTAAAA ACTAGCTGTT TCTGAATACC ATAAAATATT GCCAGTATTT
40151 TCAATTGTAT AATAACTTTT TTTTTTTTTT TTTTTTGAGA TGGTGTCTTG
40201 CTCTGTCACC CAGGCTGGAG TGCAGTGGCA CGATCTCGGC TCACTGCAAC
40251 CTCCACCTCC CGGGTTCAAG AGATTTTTCT GCCTCAGCCT CCTGAGCCAC
40301 TGGGACTACG GGTGCCTGCC ACCATGCCCG GCTAAGCTTT TTGTATTTTT
40351 AGTAGAGACA GGGTTTCACC ATATTGGCCA GGCTGGTCTC AAACTCCTGC
40401 CCTTGTGATG CACCTGCCTC GGCCTCCCAA CGTGCTGAGA TTACAGGCAT
40451 GAGCCACCTC GCCCGGCCTC CTAACTTTTT AAAAAGTATG TTTCTTTGAT
40501 TCTGGATCCA AATAGGCTC TTACATTATG ATTGGTTTAT ATGTCTTTTA
40551 ATTCTATTTT AATCCATGAA CTCACATTCC ATCTTTTGCT CTTTCTCTCT
40601 CTTCTTTTTT TCCTTGCAAT TTATTTGTCA AAGAAAGAG TTTCCCATTA
40651 TCAGGATTTG CTAATTGCAT TACCATCTTG TAGTTTAACA TGCTCTTCTG
40701 TCTGTATTTT CTGGTTACTC AACATTGTGA TTCATGTAAA ATTACTCAAG
40751 CAATATGAAA TACTCTGCTT TCTAATTTAA AGAGGGGCAC ATAGAAACAT
40801 AACTAGGTAT ATATAAATTT AGAAAAACCT ACTTGAGTAG CACATATAAA
40851 TACTAAGAGG AATAAGATTA GTTGGTGTGA TTGGAAACAT GGAATTACAC
40901 ATGAATTATT TCATGTAGGA GGTAATTTAT GCAGAAGATA TGGAAATGGC
40951 ACAGGAGATT GAGGAAAAAG TCATCTCTGG TGAGAGGAAT ACTGTAACTG
41001 AAAATTTTGT AGGTGGAGGT GGGCAAATGC CAAACTAAGT AAATGAGAAT
41051 TACCTAGCAT AATGCCTAAC ACAAATTTGG TGTCCAATGA ATGGTCATAT
41101 CTGTAAACTG GTAATAAAGT ATATTTACAC CTTAACCTGA ATCACAGTGG
41151 AATTCAGTCA CCCTTTTAGAT TTCCAGCTTC CCAACTGTTC TTTGTATCAT
41201 TACCCTATTA TTAATTCCCA CAGTTTGAGA ACTTGATATC CCCAGGGCCT
41251 ATTGTTGCCA CGGAACCACA GGCCTGGGAG TGGTAACAGG CTGGAAGGCT
41301 TGGCGGAGGG TTGGTGAGAG TAGGAGAAAA GGGTGCTACA TCATCCCAAA
41351 CTCAGAACTT AAATGAATTA TGTGCAACTC TTTTTTTTTT TTTTTTTTTT
41401 TTTGAGACGG AGTCTTGCTC TGTCGCCCAG GCTGGAGTGC AGTGGCAAGA
41451 TCTCGGCTCA CTGCAAGCTC CGCCTCCCAG GTTCATGCCA TTCTCTTGCC
41501 TCAGCCTCCC GAGTAGCTGG GACTACAGGT GCCCGCCACC ACGCCTGGCT
41551 AATTTTTTCG TATTTTTAGT AGAGATGGGG TTTCACCGTG TTAGCCAGAA
41601 TGGTCTCGAT CTCCTGACCT CGTGATCCGC CCGCCTCGGC CTCCCAAAGT
41651 GCTGGGATTA CAGGCGTGAG CCACCGCGCC CGGCCTGTGC AACTCTTTAC
41701 ATGACCAAAC TTTCCCAGTT TACCCCAAGA ACCCAATAGG GAATTTGCTT
41751 TATATTTAAA AACCAGAGTC AAATCAGCAC AATCGAAGAA GTCATCAGAT
41801 TAAAGGTGTC TTCACATCTC CACCTTTTCT AGCTTTGAAA GGGGAGTGGT
41851 GAATTCTACC TAAAGAGAGC ATTTTAACTT ATGACTCAGC GTTCAGTTGA
41901 GACACAAAGT TATTTTGCTT TTCTTCGAAG GAGCTCAGAA TGACCCTGTG
41951 CATAAAATTA ATGTAAAGGA AACAAGACTA AACAAGAAGG CTAATAAGCA
42001 GCCTAGTGGA ATGAAAGGAA ATCTTTATTT GTATCAGTCA AAATTGATCA
42051 AATATTACCA TTATGTTTGG TTCAACTAAA ATAGTCTGAG TGGATGTGAT
42101 TGAAACCCGG ATAGCAATAG GGACCGTGCA AAGGAATATT GCAACAACAG
42151 TGATGTGATG AAGCCATGCA AGGTATGGGA TTGAAGGAGA GAAAGGCAAT
42201 TCTGGCTTCA TGGACTTTCA AATGCATGTC TTTCCTCAGG CCTTGAACGT
42251 GGCTACCCAG GTTGTCTGTT TGTATTTTGT TTATGTAGAA TCGAATGTGG
42301 AGAAAGAACC GTTCTTTCTA TGCGAACAAT CATTGCATCG GAACAGACCT
```

FIGURE 3K

```
42351 GAATAGGAAC TTTGCTTCCA AACACTGGTG TGGTAGGTTG TTGGCTTTAT
42401 TTCTTGCAAT GTCTCTTCAC TGAAAGGGTG ATGTTCACAG GGAAAGGCCC
42451 ATGAATTCAA ATTAAATACA GAGCTGGCCT GTCTGAATCA GGGAATAATT
42501 TAAATGATAA ATGCTTAGGT AAATGTAATG CTGCGACTGT TGGCCAGAGT
42551 CAGCAAATCA CTTTGGCCTC TCCTCTCTCC TGTTTCCCTA TCTTTAAAAT
42601 AAGAAAGTTG AATCAGTTTT TTAAGATCCC TTCTAGCTTC AAAATTCTAA
42651 AATCTATTAT CTTGGAATAA TAAAGAAGTG ACAGTTAAAG ATCCTATTTT
42701 AATAAACAAA AACATTCATC ATTAGAATAT CAAAGACCTG AGATGGGGGG
42751 GAGGACCTCT CTTTTTTTTT TGAGACAGAG TCTTGCTGTG TTGACCAGGC
42801 TGGAGTGCAG TGGCACAATC TTGGCTCACT GCAGCCTCTG CCTCCTAGGT
42851 TCAAGGATTC TCCTGCCTCA GCCTCCCAAG TAGCTGGGAC TACAGGCATA
42901 TGCCACCGTG CCTGGCTAAT TTTTGTATTT TTTTTAGTAC AGATGGGATT
42951 TCACCATGTT GGCCAGGCTG GTCTCAAACT CCTGGCCTTA AGTGATCCGC
43001 CCACCTCGGC CTCCCAAAGT GGCTCACAGG AGTGAGCCAC TGTGCCTGGC
43051 CTGGACCCCT CATTTTTAAT TGCACAAGTA AATGTTTACT TCTATAGTGT
43101 TTGAAGACAT TTTTTTCACT ATTCACTTTC TTAATTTCTT TAATAAATAA
43151 TATAAAGAAA ATATAAAAAT ATTAAAAATA GTATAAAAAG CAGCACAGTG
43201 GGAATTTATT ATTTCTTAAT TCGAATGAGT TAAGGCATTC GATGATGTTG
43251 AGTTATGCAT TCAAGAACAG TCTGCTTTCA GGAGTTTGAA GATTTTTTAA
43301 AGAACTAAAA GTAGAATTAC TATTTGACTC AGCAATCTCA TCACTGAGTA
43351 TATACTCATA GGAAAATGAA TCGATCTACC CAAAAGACAC ATGCAATCAT
43401 ATGTTCATTG CAGCACTATT CACAAGAGCA AAGACATGGA ATCAATCTAG
43451 GTGTCTGTCA ATGGCGGATT GGATAAAGAA AATGTGGTAA ATATACATCA
43501 TGGAATACTA CACAGCCATA AAAAAGAACA AAATTATGTC CTTTACAGCA
43551 ACATGGATGC AGCTGGAAGG CATTGTCCTA AGTAAATTAA CACAGAAACA
43601 GAAAATCAAA TACTGTATGG TCTCACTTAT AAGTAAAAGC TAAACACTGA
43651 GTATACACAG ACATAAAGAT GGGAATAGAC ACTGGGGACT CAAAAAAGGG
43701 GCAGGGAAGG AGAGAAGGGG GAAAGAGTTG AAAAAGTACC TAAGTGGTAC
43751 TGTGTTCACC ATTTGGGTGA TGGGTTCAAT AGAATCCCAA ACCTCAGCAT
43801 CACACAATAT ATCCATGGAA AAAACCTGCA CATGTACCCC CTGAACCCGA
43851 AGACAAAGAA GTTTGCTTTT AGGGGGGTAG GTGTTAGTTC ACTCTTTCTT
43901 CCCACCCACT CAACATTATT TTCATAGTA CTACATTTCA GAAACAGCTA
43951 CGAAAATAAA CTAACCCTGA CAAGGAGTAT GCATCATCTA TATTTTTGGG
44001 CTCCATGGGG CCCATAAGGG AGAGAAGCTA TTGTATCCAC AGAAACATCT
44051 TCTTCCTCCC AGACCTGGAC CCTATACAAT CCTATGCACA TAATTTTGCC
44101 TATTTCCTTT AAAAAGGTAA AATTTCATGA TTTTAAACAT TTTATCAAAA
44151 TCCCAGAATA CCTATTAAAA CCTCACAACA TTCAGCCTGG GAAAGCTGAT
44201 TGCTAAAACA AAAGAAAACC AAACCTCACA ACAAAGCACT TACCTTATTT
44251 CCTTATTTTT TTCCCTGTCT AGGTTAGAAA CTCCATGCAG ACAGAAACCA
44301 ATACCCATTA TCTAGTGCAG TGCCTGGCAC AAGGAGGGTC CTCATAAAAT
44351 ATTAACTAAA TGAGTCCATG AATGAATTTA GTTGCTCTGA GAGCTACAGA
44401 TATGGTAGGA ACTCAGAGGA AGAAGCAGTT CATCCCGACT TAGGTTCCAG
44451 GGAATCATTT AGTGGTTTCT CCCTAAAAAA CCACTCGTGT TCCCAGGACA
44501 CCAAAGTTTG CTGCGGCACT AATAACATGC CAGGGGCTCA CAGGAACAGC
44551 AGCCATGTAA AAAGAATCTA AGTAAATAGA GCTGACAGTT ACTCAGCGCT
44601 GAGCCATTGA CATAGTTCAT CTTCCAGATT TCATTATCTA TGAATCATAG
44651 ATGGAGAAAC CCGGGCTGAA AACAGTTAAG TCCCTTCCTC AAGGGCACGT
44701 AGCAAGTATG TGCAAGTACG TGGCAGAGCT GGGCTATAAA CCCAAGTTAT
44751 CAGTTCCCTT TTGGAAGTTT TTATTTTATC TTCAAGCTCT TTTGGTGCTT
44801 GATTTTACTT AATATTTTTC TTGGTGAAGT CAGTGTTATT TAATTTGGAT
44851 AGCCAAGTAG TCAAAATATA TTCTGTTATT GTCATCAAGA AATGTCTCAG
44901 TCCCCTCTTG GGCATGGTGC TATATTGTTA CGTATCATAA GAGTGAAAAA
44951 CAGAAACAGA AGCAGCAAGC ATATGGGTTT TTAACTAAAA AAAAAAAAAA
45001 AAAACCAAAT AAAAAGTAAT TGTAAGGAAC TGTCCTTATT ACCAACTGTT
45051 CCAGTATCTA TTCTGTACTA TGTAAGCAAG ACAGTGAGAA AGAAGAATTT
45101 AATCTTTTCT CATCCCTACA ACTAGAATGT GCCCCTATGA TTCTTTATAT
45151 AAAGGATCCA AAAACACCTC ACTTATTAAC AGGAAGTGAC ATATCAAACC
45201 TACTTACTCA TTTTATGCTC CTCTGTATTA AAATTTTTTG TGTGTGTGTG
45251 TTGGAGATGA GAGTGGAGGG TAGGTTGTAG GGGTGTCTTT GTCTTCTCAG
45301 GCTGCTATAA CCAAATACCA TAGGTTGGGT GGCTTAAACA ACAGAAATTT
45351 ATTTTCTCAC AGTTGAGGAT TGGGAGTCCA AAATCAAGGT ACCAGCAGAG
45401 TGAGGTCTTC CTGAGGATTC TCTCATTGGC TTGTAGATGG CTGCCTTCTC
45451 TCTGTGCCCT CACATGGCCT TCTCTTTCTG CACAAACCTC CCTGGTGTCT
45501 CTCTTTATTC CTATAAGGGC ACCAGTCACA TTGGATTAGA GCCCCATGCC
45551 TATGACTTCA TTTCACTTTG TCTCCTTAAA GGCCTTATCT TTAAATACAG
45601 TCACATTGGG GCTTAGGGCT TCAACATAGG AATTTGGGAG GATGCAATTC
45651 AGTTCATAAC AGGAGTACAT TATGAGAACC TTTGGTCTCA AACTTCCTAA
45701 GATAGCACCA CACATTTTCT AAAACACTGA GTTCAACTAC AAAGTTTTTG
45751 CAACTGGCTT GAATGGAAAA TTCTTTATTT CTTTTTCTAG GAGACTATAG
45801 TGTTTTTTAA AATTATTTTT TATTATGATA AAATACATGC AATATAAAAT
45851 TTGCCATTTT AACAATTTTT AATTGTACAG TTCAGTGGCA TTAAGTACAT
45901 TCACAATTAC TACTATCTAT TACTAAAATT TTTTAATTGT CCCAAAGAGA
45951 GATTTTTACT TATTTGTAACC AGTAGGCAAT ATCTCCTCAT CCCTACCTTC
46001 TCCCCAGCCC TTGGTAATTT CTTATCTACT TTCTGTCTCT ATGAATTTGC
46051 CTATTATAGA TATCTCACAG TGTGCTTGGT TCCATGTCTA TAGATCAAAG
46101 AATGCTTGAG CTTGGAGGGA TCCAGTGGCC CAAGTTCCTT CCTGGTACAG
46151 ATGAGGCCCC TGAGGCTGAG ACGATGAAGT AGTTGCCCAA ATTAACATGA
```

FIGURE 3L

```
46201 CTGCTTAATG GTAAAGCAGA GTCTCGACCT CAAGTTTCCT GCCTCTTCAG
46251 GGCTCTTTCC ACTAAAATGC TTGAAATCTC TAGAATGACA ATCATAGAAT
46301 GAGAATCTGA GGCTCACTGT CCAGCATAGT AGCCACTAAC CACATGTGGC
46351 TATCCAGTGC TTAAAATGTA GCTTGTCTGA ATTGAGACAT ACACTGAGTG
46401 TTAAATACAC ACCAGAATTT GAAGGCTTAG TATGAAAAAA GTAACATAAA
46451 ATATTTCAAG AATAATTTTT ATATTGGTTA CACTTGAAAT GATACTTTGT
46501 ACATATTTGG TTAAATAAAT TACAATATTG AATTAATCTC ACATATTTCT
46551 TTTTGTGTGT GTGTGTGTGG CAGGGTCTTG TTCTGTCATC CAGGCTGGAG
46601 TGCAGTGTCA TGATCTCAGC TCACTGCAAC CTCTGCCTCC TGGGTTCAAG
46651 CAAGTTTCGT GCCTCAGCCT CCCAAGTAGC TGGGATTACA GGCGTGCACC
46701 ACTATGCCTG GCTATTTTTG TATTTTTGGT AGAGACGGGG TTTCACCATG
46751 TTGGCCTCGC TGGTGTCAAA CTCCTGATCT CAAGTGATCC GCCTGCCTCA
46801 GCCTCCCAAA GTGCTGGGAT TATAGGTGTG AGCCACCGTG CCTGGCCTTC
46851 TTTTTATTTT TCTTAAAGTG GTAACTTGAA AATTTAAAGT AAATATGTGA
46901 CTTGCATTAT ATTTCTATTA AACAACCCTG GTCTGAGGAT TCATATTAGG
46951 GCACCACCTC TCTATTTAGT GGTTATGTCT TCCCCGACCT CCATACCCAA
47001 TATATAATCT CTATTCTCTA AGAATTATAT ATCACATAAA AGGGCAGGAA
47051 TATTCAAAGG TGACCGAACT ATCAAAAATG GTTTATCCAA TCACCTTATT
47101 GGTTAAAAAT GAAATACTTG GGAAGACCTT AGATGTTCAC ATTTCCTCTC
47151 AGGGAAACAA TTTTTTTAACA AACATTAATG TTGTGTTTGT ATAATAACAG
47201 GAATAAAGCA GAATGAGCTT AATTAAGAAA AGCAGGCTCT GTAAAGGATAG
47251 TGAGTAGCCT CAGCCATGGA CTCCTGAGGC AGAGATGCAG CTGGACTCAG
47301 AAACAGAAAG GAACTGGGCC TGGAGCCCTA GAGAGGCTCA GTGAATCCTT
47351 CCTCTCCCCT TCTCATCTCT GTGATGCACA CTGGCTTCTT TCAGGTCTCA
47401 GTCCACATGA TGATGATGAT GATGATGA ATGATGATGA TGATGATGAA
47451 CAGCAACAGT TATGAAATGC ATACTACATG CCAGGCACTG TGCAAAGCAC
47501 TTTGATGAA CTAGCTCATT TAATTCTCAT TCAATCAGCA TTTAATGTAT
47551 AATTTTTCAA TTTTGCAGAT AAGGAAATTG AGATACAGAT AGATTTTTAA
47601 AAATTTACCC AAAGCCATAT AGCTAATAAA TGGTAGTCAA GATTTAGAAT
47651 CAAGTAATTG GGTGCTTAAC AATATGCTGT ATAGCCTCTT ATTCTGAAGA
47701 ATGGTTACCA CCAAGAATAT CCAGATTGCA TCTCCTAAAA TGACAGTATT
47751 TACTTCATAG GGCTGCTGTA AGAATTACAT GAGATGTGGC AAAAATCTTA
47801 GCAGAGTTCC TGACGTACAG CATGTGCTCC ACAGGTGTCA GCTGGTAGTA
47851 TTACTATTTT TACTGTCTGT TCAAGAGAGC AGCTAGACTG AGACTAGACT
47901 CTTAGTATTG ATTTCAAGTT ATCTTTGAAG GGATTCAGAT TGGCAAGCAC
47951 AAGAGTCAGA CCCTATCCTG AGCCCTCAAC TGTTTGCAGG AAGGAATAAT
48001 CTCTTGTGTC ACATGCAGCT TGCTGGGGCT TCACCTTGTG AATTAGGGAC
48051 AGGGGGAGAA GTGTTGGAAG GCAGCCTACC ATCTCAAGTG ATGCAAATTA
48101 TAATCTACCA AAGGAATGAA TGAACGTTGG TCTGGCAACA AATATCACCA
48151 TCCCATTTTA TTTACTAAAC TTACTAAACC ACTTTAGCAA GTTAAAAGTA
48201 GCACTGAAGG CAGATTTACA TATTCTGAGC TCTGAAGTGA GGCTTTTCTT
48251 TTATGGGCTA TATTGATGGT AGCTTTAAAA CTACAAATAT CAGAAAAACT
48301 AAATTTACAG TGGATTAAGG AAAATGGGGT TTATTTTTTC TCCCATAACC
48351 ATAAGTCTGG AGACAGGGCT GGCATCTCTG AGGATCTCTT AGCCACTTTC
48401 TCAAGGTTGC AAGGGAGACA GGTGCTGGGA ATGACTGTTA GAAGGTCAGC
48451 TATGTGAGCA GATAAGTATT TGACTTCAAA AGAAACATAA ACTTAGTGG
48501 AACTATGTTC TTTGCAGAGC CCTACCTAAT CCATTCATCT AAAAGTGTTG
48551 CAACATAGGT AGGAGAATAC GTTGTCTGGG AAACCACAAA TTACAGTACT
48601 ATGTGCATCC CCTCATAATT TCACCTTAAC AATTTCGTTA CAGAGGAAGG
48651 TGCATCCAGT TCCTCTAGTT CGGAAACCTA CTGTGGACTT TATCCTGAGT
48701 CAGAACCAGA AGTGAAGGCA GTGGCTAGTT TCTTGAGAAG AAATATCAAC
48751 CAGATTAAAG CATACATCAG CATGCATTCA TACTCCCAGC ATATAGTGTT
48801 TCCATATTCC TATACACGAA GTAAAAGCAA AGACCATGAG GAACTGGTAA
48851 GTGCTACTTA ATTATTTTTC TCATTAGCAT TTTGGAAATA AAATAATACT
48901 TAGTTGAAGA ATCAAAAACT GGGAAAAATT TTGGCCTCTA GAAGGCAAAT
48951 GATAGATGTT TTAAATCATG GTGTGATCCT GTTGAGAGTC ACCCTGGGTC
49001 AGTGTTCTCT AAGGGAATAT AAAGAACGTG CCTTACCCTA ACAACACACA
49051 CTTTATTCTA GCACGTGGGC TTCCTAAGCA AATGTCAGAC AAATTCCTTG
49101 AAGGTTAGGA AGGAACTACT ACTACACTTG ACCTGATCTG CATGTGAAGC
49151 GGTATAAGCA AGGATGAGTA TGGAATCATG CGACAGCTTT GTGGTCACTA
49201 GCTTCCTACA ACAGCACACC ACAGATTAAG TCTCAACACA GCACTCATTG
49251 TTTTGGTATT AGCAGCAGGA ATTGTTCCTG CCCTGACTTC CTTAACCCTC
49301 AGGGTTTTGG TCCTATTAAA GTACCTCCAA TTTTAGCATT GAGGAGAGAG
49351 TCTGTTTTTT GGAACATAAC AGACAATACA GGAAATTCAA AGAGGACTCA
49401 CACAATTTGA TACTCCCTTA GCACTTTTTA GTCCAAGATA CTGTATGTTT
49451 GGGTTCATGG CAAAGATGC AAGGATTCTT GAAGGATTGT AGCTAGGCTT
49501 TGACAAATCC TCATCCCAGA TGCTCTCCAG ACAGTGGAAG TGTTACATCA
49551 ACAGCCCCAT TCTTGGGAAG GGACTAATTT TTAGGTAGTA GCTTGTTTCT
49601 TAGTGACTCA TTTTTTTTTC TGGCTCTCTT AACAGAATAA AATATAGTCA
49651 CATTACAGGA GCTAGCAATT GCTGATGACA AATATAAGAT TATTTGCATT
49701 CTCTGAAAAT AGCCCATTTA GAACATAAAT GTACTTGATA CTTGAGCTTT
49751 TTCTTCTCA AGGGAAAACT GTTAAGGAAA GCACCTTTCA AAAATATTAT
49801 CTTTGAAGAA ATAAAAGGAA ATTTATCATG ATTTGGGAAG TAGAATTAGT
49851 CTAATTATGC TTTTTTTTTT TTGCATCACT GCCAGCACAC ATATATGTTG
49901 AGAGCCATTA CGTGTAAAAT ACCTTGTCAA TGGATGTTTA AAGAAGCATT
49951 AGGTAAAATC CTGCCCTTTA AGAGAATGTG TTATGGTTAG GGAGCTCAAC
50001 CATTAGCAAA TGTTACAAAT AGTTGTACTC TAAGGCGACA TAGAGTAACT
```

FIGURE 3M

```
50051 ACTAAATACG TGGCACAGAC AGTACAACTC ACTTCTAACT AGAATATCAA
50101 GGGATGGCTT CACTAATGCA TTCAGAGGGA AATGCTGAGA TAAGTGAGGA
50151 GATAAAGTAG TTACTGTCCT TGAGGAATTT ACAATCTATT AAGGGGGGGA
50201 AAAACTACAA ATAATAAAGT GCTGTTGATG TCAAAGATCA GCTACATTTT
50251 AGACAGGCAT TGAAAGAGGA TTTCTATAGG CAGACAGGGA AGGAAGGACC
50301 TTCCAAGCAA AGAAGTTGGT GTTCACCATA AGAGGATGCA AAAGTGGAGG
50351 GTGATAGCAT CAGAAAGTAG ATTAGGTTGG CTTCTGAAGG GGTGTGACTG
50401 TCAGATAAAT TTGTATTTCA TTATGTAGAC AATGGGGTTA CATTAAAACT
50451 TATTTTTTGA ACAATGAGAT GGCATAAAAT AATATCCGCT GATAAATCTC
50501 TTGAGTTTTT CAAGAAGGTA ACAGTGTATA CCATGATGCT AGTTCCAATT
50551 TCCGAAAAGT TCCAGATAAG TGAGAACTTC AGAATAGATT TGACAAAATG
50601 AATATCAACA GACAAATGA AGTCAAATGG GGGTCTTAGT TATTATCCTG
50651 CTCCATACCA GAGGCATAAT CTTTTTTGAT TTGATGAATC TATGGAAGTC
50701 ATTAGACATT TTACACAAGA AGAAAATAGA AGTTGTGAGA AGGATAAGAA
50751 GTGAGTCATG CATGCATTAG GTGTTTGTAT GTGTTTAGAA AGGTTGGATT
50801 TAAAGTTTGG TGATAATTTT GTTCAGAAAT GGAGTACCTC TAAGCCTTTG
50851 AGATGTAGTT ATACTTCATT TTCCATAATA AATGAGTTCC CAAAAAGGCA
50901 TGTGATAATT TTTTTCTGCA AATTAATATA TTTATTTATA TAAATTATTT
50951 CAATATATTG AAATAGTTTA TGTTTAAAGC CACCCAATTG TGATTGCCAT
51001 AAAGTGCACA TATTTTAAAT TAATTTGTTT ACCTTATTTA TTTGCCTTTT
51051 AGATGAATCT AGATTTTCTA CCTGTATACT TTGATTCAAT TAATGTATGA
51101 TTATTTTTTA GAAACTTCTA CTTGTCATGT TTCAAAGCTG CACATTAACT
51151 GAAATTCTAT ATCTTTTTGC TTCCAGTCTC TAGTAGCCAG TGAAGCAGTT
51201 CGTGCTATTG AGAAAACTAG TAAAAATACC AGGTATACAC ATGGCCATGG
51251 CTCAGAAACC TTATGTAAGT ATTTCTTCTT ATGATCTTAG AGAACTTTGA
51301 GCTACTAAAG AAATCTGTGT GATCTGTTTT TCTTTGTGTA TTTAATTTTT
51351 CTGAATTAAA TAGGGTCACA TGTAATAACA CTGAATTGTA ATAATTAGGA
51401 ACAGAAGCAT AATAGCTATG ACAATGCTGA ACAAAGCTAT ATTAATAAAT
51451 GAGTTACTAA AAAGAAGCCA AAATCCTATT TAAGAAATCA TATTTATCAC
51501 AATCAAGTAG GAATTACAGA ATTGGCATCA TACTAGTTGA GTGAAGCAGA
51551 AAAGTTCATA AAACTTTTGC ATGATTCCCA GGGCCACCAT GGAAGGTTGT
51601 GCAGGTTGTA CACTACACTA ATCTAGGGCA TGCCATTTGC ATCAAGTGTT
51651 TTTTAGTGTT AGCCTGTTCC CAAGAGTATA GCTCATAACA CATTACAGTT
51701 GATTGTCTTT AATATATATT ACACACACAA AACTTGTGAC AAACTCTTAA
51751 CAAAAAGTTT TGATTAATTT TTGCTGAAAG ATATTTAGTG AGTAACTCCT
51801 ATCTACACAC AGTGGGAGGA CAGACTGATT TTGCCCTTTT GAAGTTTGAA
51851 GGGAGATGGG AAAAGAGGAG CATAAAATAA ACCTGTAACC AGGCATCAGA
51901 AAACTACAGC CTGAAGGCCA AATCCAGGTT TTTCCATTTT TTTTTTTTTT
51951 AATGATTAGA AAAAAACAAA AAGAGGCCAG GTGCTGTGGC TCATGCCTGT
52001 AATACCAGCA CTTTGGGAGG CTGAGGCAGG AGGATCACTT GAGGTCAGGA
52051 GTTCGAGACC AGACTGGCCA ACATGGTGAA ACCCTGTCTC TACTAAAAAT
52101 ACAAAAATTA GCTGGGCATG GGGCACTTCC TGTAATGCCA GCTACTTGGT
52151 TGGCTAATGC ATAAGAATTA CTTGAACCTG GGAGGTGGGG GTGGCAATGA
52201 GCTGAGATTG TGCAACTGCA CTCTAGCCTG GGTGACAGAG TGAGACTCCA
52251 TCTCAAAAAA GGTCGAAACT GTATTTATCA TGAACACTAA AATATGTACA
52301 CATTTTAGTT AACATGCATT AAACTGTAAC AAGTCTTCTG GCAATTGTAG
52351 CTTTCATGAG ATGCTTCCCA AACTGTATTA GATAGATGCT AAAATTATAA
52401 ATTAAAATTT TGGGTCAGAC TTTGCCATAA ACCTGGACTC AATTTAGCAC
52451 CCCCCCAAAA AAAGTCAGAT TATTCAATTA ATGCGGTTGG AAAACCTAAC
52501 AAGTTACCTA GAAAAAAATT AATTGGATTA TTAACATGTC TTTCACCAAA
52551 GTAAATTCCA GGTACAGCAT ATATTTTCAT ATGAAAACCC TGCATAAACC
52601 AAGTTGAAAT CTCAGTAAGG AGAAAAAATT CTTGTGAAAG GAGAAATGAA
52651 TGAAAGGAGA AAAAAAGGTC TACATGCCAA ACAAAGCTAA TAACACTAAT
52701 GTCGTTTTTA TAAGCAATTG ATAAAATGAA CCAAGTAGAC AAATGAGGAA
52751 GGACAATTGA TAGGAAATAT AAAGATAGCC AATAAAATATG CCAAACAAAT
52801 GTGCAACTCA CTGATAATCA AAAAACATAA ATTAAGACAG TTGGATATTA
52851 TTTTTCGCCC ATAAAATTAT CAGAATTCAT AATTCCTATT GATGGTATGG
52901 GAAGGGGAAA TGGGCAAATT CATACCCTGC TTGTGGAAGT ATAAATGAAT
52951 TCAGTTCTTT TGACGTCCAT TTGGGAACAT GCCGTAATTG CAAAAAGTAC
53001 AGAGCCTTAG ACTAGCAAAT CTATTCTAGG GAAGAATATT CTAAAGAGAC
53051 AAAGAAGCAA TTATGTATAA ACAAGGGTAC TCATTGTAAA GTTGTTTATA
53101 TTAGTTAAAA ACTGAAAAAA ATCTAAAGGT ATACAAACAA ATAAACATTT
53151 AAATCAAACA ATTCCCAGTT TGTAAATTAA TTTGAAACGT CTGTATTTCA
53201 ACAATTTCTT TCTTCTTCTT TTAGACCTAG CTCCTGGAGG TGGGGACGAT
53251 TGGATCTATG ATTTGGGCAT CAAATATTCG TTTACAATTG AACTTCGAGA
53301 TACGGGCACA TACGGATTCT TGCTGCCGGA GCGTTACATC AAACCCACCT
53351 GTAGAGAAGC TTTTGCCGCT GTCTCTAAAA TAGCTTGGCA TGTCATTAGG
53401 AATGTTTAAT GCCCCTGATT TTATCATTCT GCTTCCGTAT TTTAATTTAC
53451 TGATTCCAGC AAGACCAAAT CATTGTATCA GATTATTTTT AAGTTTTATC
53501 CGTAGTTTTG ATAAAAGATT TTCCTATTCC TTGGTTCTGT CAGAGAACCT
53551 AATAAGTGCT ACTTTGCCAT TAAGGCAGAC TAGGGTTCAT GTCTTTTTAC
53601 CCTTTAAAAA AAATTGTAAA AGTCTAGTTA CCTACTTTTT CTTTGATTTT
53651 CGACGTTTGA CTAGCCATCT CAAGCAACTT TCGACGTTTG ACTAGCCATC
53701 TCAAGCAAGT TTAATCAATG ATCATCTCAC GCTGATCATT GGATCCTACT
53751 CAACAAAAGG AAGGGTGGTC AGAAGTACAT TAAAGATTTC TGCTCCAAAT
53801 TTTCAATAAA TTTCTGCTTG TGCCTTTAGA AATACAACCA TGCATTCCGT
53851 TTGCTCCACG GTAATTAGGC GATGGCCCAG AAAGGGGAGG GGTGTCAAAA
```

FIGURE 3N

```
53901 ACGACAAACA TAGCCTCTCA TTCCAGCTCA GCTGCTCAAT AAACACTGTT
53951 GAACGAATGA ATGAGTGGCT CTAGGTACTG TCAACAAATG CCGCATTTTG
54001 CGCATTTACA ACAGCTGTTT ATGGTAAGGA ATTATGTAAT AAAAAGAGAA
54051 AACTCACTTA AATTCACTTT TAATTGGGAA TTTTAGTTCT CCCGGGCTCC
54101 CAGTTTCCTT TCCTAGGATC TCTCACAGAG CACAGATTCG ATTTCCAAGT
54151 CCCGCCGCAC TCTTACCGCT CGCATGGAAC CTTACGCCTA GAGGGCGTGT
54201 CCACGAAGGG TGGTGTCTGC GCACTGACGA CTAATCTGAC GGCCGGAAGC
54251 TGCCTGGGTC TACAGAGGAA CAGGGCAAAC CTCTGACTTC CGGCGGCATT
54301 TTGAGGCGGT CCTCCTAGCG GCCTGGTAGT GTTTTTGTTG CCTTTTCTTA
54351 ATCTACAATC TCTTCGTTAT TTTTCTTCCT GCGACCCAGT TTCGCTTGAC
54401 CCTGGAGAGG CGGCGGGCGG GTTGGTTCTG CTTCTCAGCC ATCCCGGGGG
54451 CTCCTCGCTA GCCAAGAGCC GGTTCCCGGG AGCCGCGCGC GCATCGCTTT
54501 CTCCTCGTCG TCGTCCTCCT GGGTCCAGGC GCGGGGACAG AGTCGCCTCC
54551 CCCGCTCCTC GGAGCGGCGG CGGCGGTGGT GCCTCCGGAC TGCACTTGCG
54601 AAGGGAGCTT GGGGAGGAAG TAAGCGTTCT GTGAATTGGT GTGGGTATCT
54651 GGGGAAGGCA TTGAGCGGAC CCGTAATGCG GAGGCCCGGG TTACCCCCCC
54701 CCGTCTTTGC TTGAGTCACT GGGATTTTGA GCTTTCCTTG AGCATCCCAC
54751 CCTTAACTCT GCAATAGCCC CCTGTGCTCA GGCGTAATTT CTCACTCTGA
54801 TTATGATTCT GGCATTTGTC TAAGGGCGAT AAGTAGACTC AGACAATAGG
54851 CTGTACCCCT CGTTACCATT TGATGTAAGC ACGGGAACCC TTGTATGGTG
54901 TTCGTATTTG TGTGCGATGG AAGGGTGCAG CAATTTGGGC TTAAATTTAG
54951 AATCTTCCTC TATACTCATT CCAGATCTGT TAGAGAAAAA CATCTTACTT
55001 GTGATTGGTC TTGTTTTTTT TTTTTTTTTT TTTTCCCTCA GCAGTGATAA
55051 CGATTTAGGT CCTGGGAATT GAGTGCTACT TTATCTTCAC AAGCCTTAGG
55101 TAGGTAGTTT TGGCAACTGT CAGAAACGGG GGAAAGTGGA ATAGAAAGAA
55151 GAGAGTCTGT TTGGCGGCAT TATCTCTCTG TAATAGGCTA ACGCAATTTA
55201 TGTGGTTTGA AAATTATTTA GAGTTGATAA TACTTGAATT ATGTTGGTAA
55251 GATGTTGTTT GTGAAGGGTA GTCTTAAGGT ATTTGGTTAT ACTATGGGGC
55301 TTTCAGGTAA TTCGAACTAC TTTGAAAATT ATGGGAGTAT GAAGTCTCTT
55351 AAGATTTTTG GATTTTTAAA GTAGTTTTAA AAATTTGGAA AACATCTTTA
55401 CACCTCAAGT TTTCGAAGTC CGCGATACCG TTGGAGAATA AATACTTATG
55451 CAGTTCAGTC TATGGGTATA TGGTGCCAGT TAGCGGGGTC TAGTTCTGTA
55501 ACATTTGAAA TTACTGGCTT TAGTACAATA TATTGGAGCG TTTTGTGAAT
55551 ACAATCTATA GATTTTCAAA TAATTTTTAA TTTCTTAATG AACTATTTAC
55601 ATTATAACAG ATGACAGTTT CAACTAGAGA CTAGCAAAGT TGATGCAAGC
55651 TTGTAACAAT TGCGGCTTTA AAAATAGTTG CACTCTGAAA CTAAGGCTTT
55701 CACTCTGTGC ATCTGGTAGG ATTCAGTTTT ATCAAATGTA TGCCTCTTAC
55751 TGGCTTCCTG ATTACTGGTC ATTCTAAATG AACATTGCAT ATTTTGAGAT
55801 TTGCAAGCTT ATGTGATTTT CATATTT
     (SEQ ID NO: 3)
```

FEATURES:

| | |
|---|---|
| Start: | 2017 |
| Exon: | 2017-2090 |
| Intron: | 2091-19206 |
| Exon: | 19207-19282 |
| Intron: | 19283-22683 |
| Exon: | 22684-22808 |
| Intron: | 22809-24477 |
| Exon: | 24478-24586 |
| Intron: | 24587-28129 |
| Exon: | 28130-28231 |
| Intron: | 28232-33052 |
| Exon: | 33053-33157 |
| Intron: | 33158-42288 |
| Exon: | 42289-42382 |
| Intron: | 42383-48643 |
| Exon: | 48644-48846 |
| Intron: | 48847-51176 |
| Exon: | 51177-51264 |
| Intron: | 51265-53224 |
| Exon: | 53225-53406 |
| Stop: | 53407 |

SNPs:

| DNA Position | Major | Minor | Domain | Protein Position | Major | Minor |
|---|---|---|---|---|---|---|
| 858 | G | T | Beyond ORF(5') | | | |
| 2122 | C | T | Intron | | | |
| 4088 | G | A | Intron | | | |
| 4240 | G | A | Intron | | | |
| 4417 | A | - | Intron | | | |
| 4434 | A | G | Intron | | | |
| 4969 | T | C | Intron | | | |
| 5868 | A | C | Intron | | | |

FIGURE 30

| | | | | | | |
|---|---|---|---|---|---|---|
| 6254 | C | T | | Intron | | |
| 10171 | G | C | | Intron | | |
| 10452 | G | A | | Intron | | |
| 11613 | T | A | | Intron | | |
| 12130 | C | T | | Intron | | |
| 17868 | - | A | | Intron | | |
| 18243 | A | G | | Intron | | |
| 22450 | T | C | | Intron | | |
| 23003 | C | T | | Intron | | |
| 24056 | - | A | | Intron | | |
| 24132 | T | C | | Intron | | |
| 25713 | G | A | | Intron | | |
| 28476 | A | C | | Intron | | |
| 29404 | A | G | | Intron | | |
| 31047 | C | T | | Intron | | |
| 31445 | C | T | | Intron | | |
| 31447 | C | T | | Intron | | |
| 31600 | C | T | | Intron | | |
| 31714 | T | C | | Intron | | |
| 31715 | G | T | | Intron | | |
| 32193 | T | G | | Intron | | |
| 32341 | G | A | C | Intron | | |
| 32561 | A | G | | Intron | | |
| 32601 | - | A | | Intron | | |
| 32642 | C | T | | Intron | | |
| 32794 | - | G | | Intron | | |
| 33071 | G | A | | Exon | 169 | A T |
| 34721 | C | T | | Intron | | |
| 35304 | G | A | | Intron | | |
| 35425 | T | C | | Intron | | |
| 36050 | A | G | | Intron | | |
| 36291 | A | G | | Intron | | |

Context:

DNA
Position

858
```
TGTCTCTTCTACCCTGTCTTTTCCAGTGTGTTTCCACTCACCTCCCGTGGATAACCAGTC
TCATTGATTTCTAATCTATCCTTCTTATGTTTCTTTCTCCACATATGAGCAGACACACAC
ATATTTTCTTATTTCTTCTTCTTTCTTATACAACAAGTGGTTACAGTGGAGGTCACTTTA
ATTCATTAAATATCATTCAATAGTTTTAAATCTCAAAAGGAAAAGTTTGAAATCTCAATC
ATTTTCTTCTGGCCAGGCACGATGGCTCACGCCTGTATTCCCAGCACTTTGGAAGGCAGA
[G,T]
GCAGGTGGATCTCCTGAGCTCAGGAGTTTGAGACCATCCAGGGCAACATGGTGCAACCCT
GTCTCTACTAAAAATACAAAAAAAATTAACCGGGTGTGGTGGGGCACACCTCTAGTCCCA
GCTACTTGGGAGGCTGAGGCAGGAGAATTGCTTGAGCCCCAGAGGTGAAGGTTGCAGTGA
GCCAAGATCACGCCTCTGCACTCCAGCTTGGGCTACAGAGTGAGACTCTGTCTCAAAAAA
AAAAAAAAAAGAAAAGAAAAAAGAAAAAAAATCATTTTCTTCTCAGAAGTTAATTGTGGG
```

2122
```
TCAAGCAACAGCCTAACTAAGCCAATAATATTTCTCTTTTTGGGAGTGGAAATGGAAGCT
AAGTTGATTGACCCACAGGAACAAGAGGGAACATGCCGTTATATTTTAACCAGTGTGTAA
AGAAGGCTGTTATGCAATCAATGATCTGGGTTTTTCTCTTCAGAGAAATTTGTTGTACAG
AAAATTGCTGTTGGGATGAAGCTTTGCAGCCTTGCAGTCCTTGTACCCATTGTTCTCTTC
TGTGAGCAGCATGTCTTCGCGTTTCAGAGGTAACCCAATAGAATCTTAGACTGTGGTGGG
[C,T]
CACTCTCCTCACTTGTTTGCCTCATGTCGTGTCAAGTCAGTGCACTGAGCTGGTGGACAA
AATGGTAAACTTTGAAGGCCAGGTCTTTCAGAACTTTCCAAGTTGCCCTGACAAATAAGT
AGACTTTAGCACAATGGGCTATCACTAAAGACAGGGTCTTTTTTCTTTCCTGGCTCTGGT
TTTATTATTGGGAGAACCTTGGATGATACGCATATCCAGTGACTATGGAGATTCAAGAAA
TTAAATCTTTTATAAACGTAACTATTTATACTCTAACTTGATGTATGATTCATATTCTTC
```

4088
```
CAGAGGTTGGCGGGCAGGTGGGCTCACTGCAGACCGCCATCTTGATCGTAGAGTAACCCA
AACTCTTGGATAGGATAATCAATAGCAAAACACACTAAAAGCTTTAGCACATCTCTTCAA
ATGAGTACGTGTATAGCAGCTTAGTGACACTAAATATAACGCAAATAGAAGAAGTAGCCA
ACAATAAAATAGTAAAAAAATGAGTGAGAACATATCTTCATGCATGGGCTTTGTTACTAT
TTGTTGCTTCAGCTTATACTCTGAAATCTGACTGATACTTATGCTTGAAAAAAGGAATGA
[G,A]
AATGTGACTATATTTTAACCAAAGAATATCACATTAAAAATATTTAATACTTTTGCATAC
TGCGAGGGTCCCTTTGCAGAGGAGAGGAGGTAGGAGGACCTCAGTATTGTAGACAGATGA
ATATCTGAATCCTGGTTCCCATCCCTTCACTGGAAATAACATTGCAAACTACTCTTTCTG
TGAGTAAAAATAAATTTTTTTACCAAATGTTTCTGTGCTCCACTTTTCCAGGAATGGCCT
ATTCCTGAAGCTAAAAAGGAAATCTAATTTCATTCAGGGCAACAGACTTTGATAAATTGT
```

4240
```
AATATAACGCAAATAGAAGAAGTAGCCAACAATAAAATAGTAAAAAAATGAGTGAGAACA
TATCTTCATGCATGGGCTTTGTTACTATTTGTTGCTTCAGCTTATACTCTGAAATCTGAC
```

FIGURE 3P

```
        TGATACTTATGCTTGAAAAAAGGAATGAGAATGTGACTATATTTTAACCAAAGAATATCA
        CATTAAAAATATTTAATACTTTTGCATACTGCGAGGGTCCCTTTGCAGAGGAGAGGAGGT
        AGGAGGACCTCAGTATTGTAGACAGATGAATATCTGAATCCTGGTTCCCATCCCTTCACT
        [G,A]
        GAAATAACATTGCAAACTACTCTTTCTGTGAGTAAAAATAAATTTTTTTTACCAAATGTTT
        CTGTGCTCCACTTTTCCAGGAATGGCCTATTCCTGAAGCTAAAAAGGAAATCTAATTTCA
        TTCAGGGCAACAGACTTTGATAAATTGTTGCTGGGGTTCAGAATATCAACCCTTCTAAAA
        AAAAAAAAAAAAAAACTAACAGTCTGGCTTTTTCTTAAAGCTGTTCTTTGTTTTTTTTTT
        TTTTTTTTGTCATAATCATTTTCCTACTAACAGTTTTTATTCATGCAGTCTCTTAGTGGC

4417    TCACATTAAAAATATTTAATACTTTTGCATACTGCGAGGGTCCCTTTGCAGAGGAGAGGA
        GGTAGGAGGACCTCAGTATTGTAGACAGATGAATATCTGAATCCTGGTTCCCATCCCTTC
        ACTGGAAATAACATTGCAAACTACTCTTTCTGTGAGTAAAAATAAATTTTTTTTACCAAAT
        GTTTCTGTGCTCCACTTTTCCAGGAATGGCCTATTCCTGAAGCTAAAAAGGAAATCTAAT
        TTCATTCAGGGCAACAGACTTTGATAAATTGTTGCTGGGGTTCAGAATATCAACCCTTCT
        [A,-]
        AAAAAAAAAAAAAAAAAAAACTAACAGTCTGGCTTTTTCTTAAAGCTGTTCTTTGTTTTTTT
        TTTTTTTTTTGTCATAATCATTTTCCTACTAACAGTTTTTATTCATGCAGTCTCTTAGT
        GGCTGATTTGTAGGTTCATTTTGATAAATTTCATCAGTGAAATGCCCTGGAACAACAACA
        AGTTTTAAAGGCATAAATATCATATGCCAAAGGGAAAGGCAGCCAAAAAATCATGACTCC
        ATATTCATTTGCTTTTAAAAGCCAAACACTATAAAGGGTAAAAATAAAATACTAGCAAGA

4434    AATACTTTTGCATACTGCGAGGGTCCCTTTGCAGAGGAGAGGAGGTAGGAGGACCTCAGT
        ATTGTAGACAGATGAATATCTGAATCCTGGTTCCCATCCCTTCACTGGAAATAACATTGC
        AAACTACTCTTTCTGTGAGTAAAAATAAATTTTTTTTACCAAATGTTTCTGTGCTCCACTT
        TTCCAGGAATGGCCTATTCCTGAAGCTAAAAAGGAAATCTAATTTCATTCAGGGCAACAG
        ACTTTGATAAATTGTTGCTGGGGTTCAGAATATCAACCCTTCTAAAAAAAAAAAAAAAAA
        [A,G]
        CTAACAGTCTGGCTTTTTCTTAAAGCTGTTCTTTGTTTTTTTTTTTTTTTTTTGTCATA
        ATCATTTTCCTACTAACAGTTTTTATTCATGCAGTCTCTTAGTGGCTGATTTGTAGGTTC
        ATTTTGATAAATTTCATCAGTGAAATGCCCTGGAACAACAACAAGTTTTAAAGGCATAAA
        TATCATATGCCAAAGGGAAAGGCAGCCAAAAAATCATGACTCCATATTCATTTGCTTTTA
        AAAGCCAAACACTATAAAGGGTAAAAATAAAATACTAGCAAGAATCTTGTAAACAGAATC

4969    CTTTTAAAAGCCAAACACTATAAAGGGTAAAAATAAAATACTAGCAAGAATCTTGTAAAC
        AGAATCAGTAATTGTATTGTGCAGTGATTACCTAAATGCAGCCTGCCAGCCCAGACTATT
        TGGAAAGAGGAAGTAAGAGACACTAGGAAGAAGACTTAGGAATTAGAGAGTGGAGGAGGG
        TTGAGGATAAAGGGCTTCTGAATTATTAATAGACCACAGGAAGTGTTCCTCTGTTGACTT
        CACATACTGTTTGGGTACCTGGAGACCAGTTTACTCTCTTTCACTTTGTTCCTACTGATG
        [T,C]
        ATTGTTTTCATCTCAAAGAACAGGCCACCAGTGGCCTTAAAACACTGTAATGTGTGCAAC
        AAAATTGCAGCCTTGGGCTATGTTCCATTGTTCAGAGACATCTTGCCAGCTTTTTAAATT
        CAAAATAATCTTTCAGAATGGTGAAAGTGTGAACCCTCCCCTGTAAACCATAGCAGGGGA
        TACACCCCAATGAACATAATGACATTCTCAGAAGGGAAGGAACAGAGGAAGTGTTGCATA
        GGTATTAAAAGCTCAGGATCTGGATTCGAGCCCCAGATCTGCTACTTATCACCCATGCAG

5868    GTCCTGCTAAAAATACAAATAGCCTCAATTTAGAAATTAGAATGTCACCTCCAACCAAGG
        TATTGTTCAAATATCCCCATCTTTGTTGTTAAAAGAAAATCTTTAAAAGAATTATATTTA
        GCAAAATTTAATTGAACAAAGAACAATTTTCTAATCAAGTAACCCTCAAAAACGAAAGAA
        GTTCAGAGAGTTCTGCTCAGCAAAGTGGGCAGGCAGCACTTATAAACAGCAAATGGAAAT
        GAGGTCCAGAAGCAGCTTGAGTAGTTACAGGTGAGCAGTTGTCTTACTGGGCATAGGCTG
        [A,C]
        TCAGTTGGCCACATGGGATTGGCTGTAGCTTGGCTGCTGTGATTGGCTGAGACTCACCTC
        GTTAGTACAAAAAAAAAATACTCCTAAGTTAGGTTGCAGTTTGTTATGTAGCGACTCAAG
        TTACGAGGCATCCTCAGACCAAATTTAGTTTAATTTAACATTATTTATAGGAAAACAACT
        GCCTCACCTCTTCCACAAACACACCTTACTCTTTTTCTTGTTAGTCTTTTTCTCGAGTTC
        TAACTTCTTAGAGTTGTGTGAGACATCTTTATTGGGGAAGCCTCTGGACCAGGACAGATG

6254    AAGTTAGGTTGCAGTTTGTTATGTAGCGACTCAAGTTACGAGGCATCCTCAGACCAAATT
        TAGTTTAATTTAACATTATTTATAGGAAAACAACTGCCTCACCTCTTCCACAAACACACC
        TTACTCTTTTTCTTGTTAGTCTTTTTCTCGAGTTCTAACTTCTTAGAGTTGTGTGAGACA
        TCTTTATTGGGGAAGCCTCTGGACCAGGACAGATGCTTCTTTGTCTAGGTTTTCACTTGC
        GACTCCATCCTTCCCCGCTAAGAGTCTTGCTTCTACCTCTGGGCTCTTGTTGTTGAGAAC
        [C,T]
        TTCCATCCCTTTAGGTGGCCCTATTGGATGGCATCTAACATTAAGTGTTTCTTTTCATTT
        TAACTACTACTATCTAGCCAACTAGAGACCAGCCACATGCAGGTTTAGCTTTATCAGGAG
        AAGCCAGGCACCAGTCTTTGTGTCTGTAAATTTGAGGAAACATCCAACTCTCTCATTATC
        TCCTGGAAGTCCCCCTACTAGGCTGAGGTAAGGGGAGTGCACCCCGAAACTTCATCCCTT
        TGGGAGGGTGGTGACTTACAGAACCATAAAAACATGCTAAAAAAAAAAATTCACAAATCCT

10171   TCATTTGTTTATGCAGCTGTTTAATGTCTATTCTGTTGTGGGTGCTCCTGGTTAGGCATT
        AATAAATGATACAAAGATCTTCACACTTTCTGCCCACTCTCATAGTTCCATTCACATCCC
        CCTTTCTCCAATCTCTTTGTCTCCAATCTGTCAAGATTTCTTCTTCCAGGTTCTTGAGGG
        GTTTTCCAGTCATGTCACTTGCCACTCTCCATGAATTCCTGCATATTCTAACACTGGAAA
        CACCTTTTCCACCCAAGGTGTATGATGAGATGCAACACTGAAGCTCTGCCTATTTGGGAC
        [G,C]
        ATTTCCCTCTCTGCTCTCTTTCGGTCACCCGAGTGAGTCCATAATGCAGCACCACTTCAC
```

FIGURE 3Q

```
         TTTTTTTTTTTCTTTTTTTGAGATGGAGTCTCCCTCTGTCGCCCAGGCTAGAGTGCAGTGGT
         GCGATATTAGCTCACTACAACCTCTGCCTCCTGGGTTCAAGCAATTCTCCTGCCTCAGCC
         TCCCAAGTAGCTGGCATTACAGGTGCCCGCCACCATGCCCAGCTAATTTTTTGTATTTTT
         AGTAGAGATGGGATTTCACCATATTGGCCAGGCTCGTCTCGAACTCCTGACCTCAGGTGA

10452    AGCTCTGCCTATTTGGGACGATTTCCCTCTCTGCTCTCTTTCGGTCACCCGAGTGAGTCC
         ATAATGCAGCACCACTTCACTTTTTTTTTTCTTTTTTTGAGATGGAGTCTCCCTCTGTCGC
         CCAGGCTAGAGTGCAGTGGTGCGATATTAGCTCACTACAACCTCTGCCTCCTGGGTTCAA
         GCAATTCTCCTGCCTCAGCCTCCCAAGTAGCTGGCATTACAGGTGCCCGCCACCATGCCC
         AGCTAATTTTTTGTATTTTTAGTAGAGATGGGATTTCACCATATTGGCCAGGCTCGTCTC
         [G,A]
         AACTCCTGACCTCAGGTGATCCACCCACCTCGGCCTCCCAAAGTGCTGGGATTACAAGCG
         TGAGCCACCGTGCCCAGCCCACTTCATTTTTTACTTGTACCCATGCACTATCAACTTGAC
         TGTCCATGTATCAGACTTCCTCTTCCTACTTGTGTCAGTTATGATCCTCTGAGAAGCAGA
         CACCAAGATGGGATTAGCTGTGCAAGAGGTGTGTTGAGGAAAATGCTTGGGTGCAAGAAA
         TGGGGAGAGGGCTGGAGGAGGCTGGGAGAGCCATGAGACTGCAATGCAAGCTTAACCCCT

11613    TTATATCAAGTACACATCTTGCAGCTGGAGAGTGAGAAAGTTAATTAAAGCTGAGGCAAG
         ACTGTAAATATGCACTGGTGTCTGTCCCAAGTGGATGTTAACTGTTCTGATGCTTTTTCC
         GACTGACATATCCAGCGCAATAGCTGAATACCATATGCCTGAGACTCTACCCCGGCAAAG
         ATGCCACATCAAGCACTATGGCTGCAATTGAGATTGTTGCTTGGTTGAGTTTGATTGTTT
         GCTGTCGTTTTCCAGGATCCATCTGGTTTTTGTGGGATCCAGATGGCAAATTAAATGTGG
         [T,A]
         TTTGATGGGATCTATCATCCCTGCATCTTTTAGGTCTTTAAGGGTGGTACTGATATTTGT
         CATTTCCCCTCAAGGATGAATTTTTTTTTTTTAATTTTGATATCTTGGCTGGGAGGTTGG
         GCAATTTCAGAGGTTTCCTTTTGGCTTTTCCCACTATGATAGCTCTGGTCTTACAGTCAA
         GGAAACAATGTGGAGGTTCTGCCAACTACCTAGTATGTTCATGTCAATTATACATTTGGT
         GACCAGGGAAATAATGATGGGGGAATCCATTAACATGGTGCACCCGCTATGAGCTAGTCT

12130    GTTCATGTCAATTATACATTTGGTGACCAGGGAAATAATGATGGGGGAATCCATTAACAT
         GGTGCACCCGCTATGAGCTAGTCTTAGGCTAGGGCTCCAGATACCCAAGTTTCAAAATCA
         ACTTGGATAGTGACCCTGCATCCAACACACCTGAAAATATTTGAGTATTACCCTTTCCCC
         AGGGTGCAGACTTACCTGAGGAAATTTCCATAGGTCTCTTTGGGAAAGGACTGAAGGAGT
         CATGATCTTTTTAGATTCTTTTTTTATACAGTTGCAGGGTCTTTCCTTGTGGGGACCTGA
         [C,T]
         TCCTCCTTCAGGCAAGAAATTCTGGGTCTAAGAACAGCTCAGATCTGGAAAAGGGCAATG
         GATTATGACTTTTGATTAGGATAGCTGTCCTCAGCCTCTCTCATTATCCAGCTTTGATTT
         ATTTTTATTGTAAAGATTGAGCAATCCTTTTGTTGGCTGCTTCTCTATCTTGCCCCTAAG
         AACTCTGTGTTCTCCTAACCGACTCCACAATTTTCTAAGGGTCATGGTCCTCTGGCTGCC
         ACTCCGACCTTACTGCTCATTGTAATAACTGTGCCCAACTTGTTACTGGTGGTTAAGCCC

17868    CTTCTGGCCGCAGGATGAGAGGGGGCACGTGCACATGAAGACACACCTACTCTTAGGCAC
         CTATAACACTCCCACGCATTCCCATTGGCAAAGCTCAGGCACTGGCTCTCAACACAACCA
         CACGGAAGGCTGGGTAATGAAGTTTTTCTGTCTATGCAGGAAGAGGCAGTGGTGTTGATG
         AACCAACATTTTCTCTGCCAAACAGTATGGAAACTTGATATATGACAAAATTGACATAGT
         GGATCCCTGGGAAAAATATAGATGATGTAAAAAATCATAATAATAAACGATGCTAAGAAG
         [-,A]
         AAAAAAAAGAAGTCTATTTCTTCTTTACACTGCACCCAACCAAATAATTTTCAATTGAAT
         TTAAAATTTAAATAAGAAGGACAGAAGAAGTATATGAGAATATCTTTATATCCCAGATAT
         CTAGAAAGACATCTTAAACCACACAAACCTGGAAGGAAATGATTAAAAAAAAAAAAGCAC
         ATCATCAAGAAAGAGAAAAGACAAATTACAAACTGCTAGAAGATATTTGCAATACATATA
         ACTGACAAGAAATTAGTATTTAGAATATATAAAGAAATTATACAAATTAACTACTACAAA

18243    AGAAGGACAGAAGAAGTATATGAGAATATCTTTATATCCCAGATATCTAGAAAGACATCT
         TAAACCACACAAACCTGGAAGGAAATGATTAAAAAAAAAAAAGCACATCATCAAGAAAGA
         GAAAAGACAAATTACAAACTGCTAGAAGATATTTGCAATACATATAACTGACAAGAAATT
         AGTATTTAGAATATATAAAGAAATTATACAAATTAACTACTACAAAAATACAAGTAAATT
         AGAAAAAAATGGGCAGTTGATCTGAATAAACATAACATATAAGCAAAAATATGAATGGCC
         [A,G]
         ATAATCAAATATAAACAACTGTACTTCATTAATAAGTCAGAAAATGAAAATCAAATCAC
         AAGAAAATTTCATTTCATAAAAATTTGATTGCAAAAGTTGAAAAGTCAGAGAGCATCAGG
         TATTGGCAAGGAGGAAGAAACAACAGGAAAATCTTTTCCACTGCTACTGACAATATAAATTG
         ATACAAAAAACTTGAGGACTGATATGACACTATCCTATGAAATTAAAACTGTGCATATCC
         CATGAAATGGCAATTCCACTTGTAAGAAAATGCTTTCATGTGTGAACTGTGGCTAGCTAC

22450    CCGTCTCAAAAAAAAAATAAAAATAAAAAATAAATAAATAAATAAATAAAAAGCACATT
         AAGAGAGAAAAATGTAAATCTTATTGGAAGCCTTTTTAAAAAAAGGAACAATGACATGA
         TGATAATTACAAGAACATGAAATTTTTATTAAATAAAATCAATGTTTAATCAACTTTCTT
         TCTAGAAAAAATTTTGTTTCCTTTCAAATATCTGATGTACACATGCAATTTTACAGTTAA
         GCCATGAATATAGTCATTCATTCATCATTGTCTCATCAAATATTTTATGGATTATCTTGTA
         [T,C]
         ATTCCAGGCCCTTTTATTTTATTTTTTTTTAGCAACTAGAGTTATAGAAAGGAATTTTAA
         AAAACTCACTGCAAAATAAATGTTTATATTACCATGTGTGTGGATGGGGACCAGCACCAG
         GGAGTGTCCTTTTCATACTCCTTATAGATAAAACTGTCATGGCTCTAGCTACAGATGAGA
         ATGATGTGAACAACTCTTTTTTAATTTTATCAATTTTGCCCCTTAAACTGTAGATTGTTC
         TCTGGCAGCCGGTAACAGCTGACCTTATTGTGAAGAAAAAACAAGTCCATTTTTTTGTAA
```

FIGURE 3R

23003    TAACAGCTGACCTTATTGTGAAGAAAAAACAAGTCCATTTTTTTGTAAATGCATCTGATG
         TCGACAATGTGAAAGCCCATTTAAATGTGAGCGGAATTCCATGCAGGTAGGCACCGTTCA
         ATACGTATTGAGTAGTTATTATAAACACTTACTATGCACTTGACTAGGGTATGGTATAAT
         TGCTTCCTGGAAAAATAAAATGTATTAACCATGGCAGCATAGAAGTCTCTGACTGGACCA
         AATGGACTGGTGATAAAGCCTAAGGTCCAGCTCTGTGATCTTGGATAAATGGTTCAACCC
         [C,T]
         TCATGACCTCCGTCCCTTATCTAAAATGCAGGTTAGACTCAGTGATTGGTAAAGGCTCTC
         ATAGTTCCTTTTTCTCTGACTCTGTACCCAGACTCAGGGAGCAAAACTGTCATTTGCCTT
         GGTAGGCTTTTTGATATCTCCTGAAAAAGCAGCTTCGGGAGGGGATTTAGCTTCTGCTAA
         TTCTTCTTCACAAAGACAGTGACCATTTCTGAATGTCTGGCTTTAAAAAGTGTAACAGGT
         GGTTGGACTCTGCAGAGACCTCGGGTTAGTCTGGCACTGCCCCTTACCACCTATATGACC

24056    ATCAGAAAGAACATGGCAGAGTTAGGAGTCGAACTTAGACCTTTCTGATGTCAACACTGC
         GGCTTTTATTTATTGGCCTAAATAAAAGTAAAGAACCCTTTATTAGTATGATAGCTAACT
         TTCAACTTGTCCATCTCAGGCGATAGAATGCCTGAATTCAGCTAAAATATTTGCCTGGTT
         AACAAATGTGGTGCTCTGAAGAGAACTTGAATGAGATGCCTTTCCTGTACTTCCCTTTTC
         CTGTTCTATTTCTTTGGCTCTGCAGAACATCTGATGCAGGTCAATGGGGGAAAAAATAAG
         [-,A]
         AAAAAAAAAAAAGAAAGAAAAGGCTTTTCTGCTTCTTCTTCCTCTTTAACTGAAAACAGC
         ATAATACAGTGTTAGTCTGGATTGAACAAAGGTACATTAATCCATATATTCATATAAAAG
         ACACTGAAGAATCACCATTGAGTAATGTTGGTAATGGTGGGAAACGGTGGTTTTTATGGA
         GGTCCTGAAAATATACCTAATAGGAGCTACTTTTTCTCTAGTGCCCATGTAGGCTCTACT
         GAAAGGGTTTGTCAACCAGTTTACCACAATGCGAGATGTCTTACTTTTACCTTGATGAAA

24132    CCTAAATAAAAGTAAAGAACCCTTTATTAGTATGATAGCTAACTTTCAACTTGTCCATCT
         CAGGCGATAGAATGCCTGAATTCAGCTAAAATATTTGCCTGGTTAACAAATGTGGTGCTC
         TGAAGAGAACTTGAATGAGATGCCTTTCCTGTACTTCCCTTTTCCTGTTCTATTTCTTTG
         GCTCTGCAGAACATCTGATGCAGGTCAATGGGGGAAAAAATAAGAAAAAAAAAAAAAGAA
         AGAAAAGGCTTTTCTGCTTCTTCTTCCTCTTTAACTGAAAACAGCATAATACAGTGTTAG
         [T,C]
         CTGGATTGAACAAAGGTACATTAATCCATATATTCATATAAAAGACACTGAAGAATCACC
         ATTGAGTAATGTTGGTAATGGTGGGAAACGGTGGTTTTTATGGAGGTCCTGAAAATATAC
         CTAATAGGAGCTACTTTTTCTCTAGTGCCCATGTAGGCTCTACTGAAAGGGTTTGTCAAC
         CAGTTTACCACAATGCGAGATGTCTTACTTTTACCTTGATGAAATGCTTATGAAGTTTCT
         TAGTGATTTTTTTTCTTCATGCTCACCTGCTGTGCCTGCAATGGGCCATGTGGGAAGATC

25713    TAATGAGAATCAATTTTATGTATATAATCTTTAAAAGCATCTGTTCCTTCCCAGTTAATT
         AAGCCAGAGTCAGTATGCTTCTAGAATGTGTGCCTGGTTGATTGAGGGGGCCTTAAAATT
         GCACCCCCCCTTTTTTAATCTCTCCTACATCTATCCAACTTAGACCACCTCTCTCCAGCA
         TCCATCAGCACGACTGCATGAGCAAACTTGATGCAGAGAGGCTTCATAGGTGGGATTTCA
         CCTTCATAGAAGGTGAAACTGTCACTGCTGTGATAAGTTTGGTGGGGAGAGGGGAATGCC
         [G,A]
         TAAACAGAAGTATTTTTAAATATTTGTTAAAACATATTTTAATTATTTTGTTCAAAAAAG
         TTATGTTTTCTTACGATATGTTCAGGAAAGAGTTGGAATGACACAGGAGGAAAAAATAAG
         CACATGGCTCTATTAGTTTTCTAGGGCTGTGGTAATAAAATACCACAGACTGTGTAGCTG
         AAATCACAGAAATTTGTTTTCTCATGATTCTAGAGGCTAGAAGATCAAGGTGTCAGTAGG
         TTTGGTTTCTACTGAGGCCTCTTTCCTCAGCTTGTAGGTAGTTGCCATCTCACAGCGTTC

28476    TTACAAAAATCCACATTGGATCCTCATTTGAGAAGTACCCACTCTATGTTTTAAAGGTAT
         GTTGTGGGGAAAGTTGTTGATCTTTCACTGTGAGGGGAGGGATTAATTCTCCAGTCGTGT
         TTGTTAAAACTTGAGTTTGTTTCCTTTGAGTTCTGAAAATATTTGCATTACAAGTGTTCC
         TCAACTTTAATACCTGGCTATTTAGGGGTTGGTTATTTTTCCCATTAATAATATAGTCTT
         GTCCTGGTCTGTATGTCCTAATCTCCTCCCACAAGGACACCAGTCAGTCTGGATTAGTAC
         [A,C]
         CACCCTAAGGGCCTCATGTTAACTTAATCACCTCTTTAAAGGCCCTATCTCCAAATACAG
         TCTCTAGGGGGTTAAGGCTTCAATTCTAGATGAATCCCAGTTCTAGAATTAACTCTGTTT
         CTGTTTATGTGACATTAGATAAGCCATTTAACATTTCCATAAAATGAAGGAAGTGGTGTT
         TATTTTTTTCAAGTCCTTGTTTTATTTTCGTTAGTGGACAAACACTATTTCTGTTAGGGG
         ACAAACACTAACAGAAAATAAAACAGGGACTTGAAAAAATAAAATTAAAAAATTAAAAAAA

29404    CTCTGGTAATCACCATTCTACTCTCTACCTCTATGAGATCAACGTTTTCCACTCCCCATA
         TCAGTGAGAACATGTAGTATTTGTCTTTCCCTACATAGCTTATTTCAGGGCATGTTGCTG
         CAAATGATAGGATTTTATTCCTTTTAATGCCTGAGTAATATTCCATTTGTTATCCACATT
         TTCCACATGCATATCCACATTTTCTTTATCCACATCCACATTTCTTTATCCATTCATCT
         GTTGAAGAACACTTAGGTTGATTCTATATCTTGACTATTGTGAATGGTGCTGTAATAAAC
         [A,G]
         TGGGAGTGCAGGTATCTTTTTGATATACTGATTTCCTTTCTTTTGGATACATACCCAATA
         ATAGGACTGCTGGCTTATATGGTAGTTCCATTTTTAGTTTTTTGAGGAACCTCCACATGG
         TTTTTCATAGTGGCTGAACTAATTTACATTCCTACCAACAGTGTACAAGGGTTCCCCTTT
         CTCCACATCCTCTCTAGCATTCGTAATTGCCTGTCTTTTGGATAAAAGCCATTTTAACTG
         GAATGAGATGACATTGCATTGTGGTTTTAATTCACATTTCCCTGATGATTAGTGATGTTG

31047    AATTTATCAGTTCTAACACAGTTTTTTGGTGGAGGCTAGGTTTTTCTAAATATAAGATCG
         TGTCATCTAAAACCAAGGATAATTTGATTTTTCCCTTCCAATTTAGATGCCTTTTATTTC
         TTTCTCTTACCTGTTTGCTCTGGTTAGTACTTCCTGGTACAGCTTTTGAAACTAAAGTAA
         GACCAGGACAACAAATCCCAGCGAGGGACAAACAGCCGGACAAGGCTGAAGTCCTTTGCA
         GTAGGGTTCTTATGATGGTTTCTACTCCAATTTCCACCCATTTGGTTATTTATTTTCAGT

FIGURE 3S

```
         [C,T]
         GCAAAATATTATGCAAGAGAAATTGATTAACCTAACTTGGATTGGATGTCTTCTCTCTTG
         AATAAAATTGACCTTAGTAAAGGTCAGTGAACATAGCCACAGCCAATTGTTTTCAGAACTA
         GGAAACAACTCTATAGTTCTGTTTTCTACCTCTCTCTCTTAAAAAAAATTTTTTTTAAAG
         CTCTGGAAAATAATGTAGTCACTAAAAATGTACATTTAATTTAGTAACATATAATTTATG
         CACAGTATCCCAATATTATCTAAATTGTGATAGGTGAGCCTCTTCAGTCATTCAAAGATA

31445    ACAGCCAATTGTTTTCAGAACTAGGAAACAACTCTATAGTTCTGTTTTCTACCTCTCTCT
         CTTAAAAAAAATTTTTTTTTAAAGCTCTGGAAAATAATGTAGTCACTAAAAATGTACATTT
         AATTTAGTAACATATAATTTATGCACAGTATCCCAATATTATCTAAATTGTGATAGGTGA
         GCCTCTTCAGTCATTCAAAGATAAGACTTTGGGTTAGGACTTCTCAATTTTAATCTGTCG
         TTTACAAGAACTTACAGTGCAGACTCAAGGCAGACATATGAAATGTTGGGTCCCCTTGGT
         [C,T]
         ATTGAGTTGGTCAATCAGATTGGATCCATGTATCATGGCATATCCACCCATGACATTTGC
         TTTCAGCCATGTTGTGTGTAGTCCTTGGAACATACTTATCTGGAACCTGTACACGTTGAA
         AAATCATGCATTCTGGATGGTTTGGTCCTACTCTTACTTGATCAAGGATGTGCAGATAAT
         GTGAGTCTCTGGGATTTTGCCAACTTTTCGGTGTCAGAACCAGTGCCAAGAAAATTGGCC
         CAGGACTTAGAAAGGTCAAGTAAAGTAATGAATCCAGACAACTTAAGATTTTCTTTGCAT

31447    AGCCAATTGTTTTCAGAACTAGGAAACAACTCTATAGTTCTGTTTTCTACCTCTCTCTCT
         TAAAAAAAATTTTTTTTTAAAGCTCTGGAAAATAATGTAGTCACTAAAAATGTACATTTAA
         TTTAGTAACATATAATTTATGCACAGTATCCCAATATTATCTAAATTGTGATAGGTGAGC
         CTCTTCAGTCATTCAAAGATAAGACTTTGGGTTAGGACTTCTCAATTTTAATCTGTCGTT
         TACAAGAACTTACAGTGCAGACTCAAGGCAGACATATGAAATGTTGGGTCCCCTTGGTTA
         [C,T]
         TGAGTTGGTCAATCAGATTGGATCCATGTATCATGGCATATCCACCCATGACATTTGCTT
         TCAGCCATGTTGTGTGTAGTCCTTGGAACATACTTATCTGGAACCTGTACACGTTGAAAA
         ATCATGCATTCTGGATGGTTTGGTCCTACTCTTACTTGATCAAGGATGTGCAGATAATGT
         GAGTCTCTGGGATTTTGCCAACTTTTCGGTGTCAGAACCAGTGCCAAGAAAATTGGCCCA
         GGACTTAGAAAGGTCAAGTAAAGTAATGAATCCAGACAACTTAAGATTTTCTTTGCATTG

31600    ATATTATCTAAATTGTGATAGGTGAGCCTCTTCAGTCATTCAAAGATAAGACTTTGGGTT
         AGGACTTCTCAATTTTAATCTGTCGTTTACAAGAACTTACAGTGCAGACTCAAGGCAGAC
         ATATGAAATGTTGGGTCCCCTTGGTTATTGAGTTGGTCAATCAGATTGGATCCATGTATC
         ATGGCATATCCACCCATGACATTTGCTTTCAGCCATGTTGTGTGTAGTCCTTGGAACATA
         CTTATCTGGAACCTGTACACGTTGAAAAATCATGCATTCTGGATGGTTTGGTCCTACTCT
         [C,T]
         ACTTGATCAAGGATGTGCAGATAATGTGAGTCTCTGGGATTTTGCCAACTTTTCGGTGTC
         AGAACCAGTGCCAAGAAAATTGGCCCAGGACTTAGAAAGGTCAAGTAAAGTAATGAATCC
         AGACAACTTAAGATTTTCTTTGCATTGAGTAGATTAAGCTAGGTAGTTCTCTTTGACTAT
         ACAATTTGACGATTAGTGGCCAATGCCATTGGGCTTTCTCACTTACTATCCTGTTAAATA
         TTGCTAGCTCCAAGTTAGGAAAAAACCTCCTGGAGTGGTTCAAATGACAATCTAAATATC

31714    GCAGACATATGAAATGTTGGGTCCCCTTGGTTATTGAGTTGGTCAATCAGATTGGATCCA
         TGTATCATGGCATATCCACCCATGACATTTGCTTTCAGCCATGTTGTGTGTAGTCCTTGG
         AACATACTTATCTGGAACCTGTACACGTTGAAAAATCATGCATTCTGGATGGTTTGGTCC
         TACTCTTACTTGATCAAGGATGTGCAGATAATGTGAGTCTCTGGGATTTTGCCAACTTTT
         CGGTGTCAGAACCAGTGCCAAGAAAATTGGCCCAGGACTTAGAAAGGTCAAGTAAAGTAA
         [T,C]
         GAATCCAGACAACTTAAGATTTTCTTTGCATTGAGTAGATTAAGCTAGGTAGTTCTCTTT
         GACTATACAATTTGACGATTAGTGGCCAATGCCATTGGGCTTTCTCACTTACTATCCTGT
         TAAATATTGCTAGCTCCAAGTTAGGAAAAAACCTCCTGGAGTGGTTCAAATGACAATCTA
         AATATCTAACTCTTTCTTTTTCTTATTTTGGAATTGCAAGTCTACATATTTGTTTGATTT
         TACAACAGTCTTCTCCCTTCCCTCTATACCAGTGGTCCTCAACCCCTGGGCTGCAGACAG

31715    CAGACATATGAAATGTTGGGTCCCCTTGGTTATTGAGTTGGTCAATCAGATTGGATCCAT
         GTATCATGGCATATCCACCCATGACATTTGCTTTCAGCCATGTTGTGTGTAGTCCTTGGA
         ACATACTTATCTGGAACCTGTACACGTTGAAAAATCATGCATTCTGGATGGTTTGGTCCT
         ACTCTTACTTGATCAAGGATGTGCAGATAATGTGAGTCTCTGGGATTTTGCCAACTTTTC
         GGTGTCAGAACCAGTGCCAAGAAAATTGGCCCAGGACTTAGAAAGGTCAAGTAAAGTAAT
         [G,T]
         AATCCAGACAACTTAAGATTTTCTTTGCATTGAGTAGATTAAGCTAGGTAGTTCTCTTTG
         ACTATACAATTTGACGATTAGTGGCCAATGCCATTGGGCTTTCTCACTTACTATCCTGTT
         AAATATTGCTAGCTCCAAGTTAGGAAAAAACCTCCTGGAGTGGTTCAAATGACAATCTAA
         ATATCTAACTCTTTCTTTTTCTTATTTTGGAATTGCAAGTCTACATATTTGTTTGATTTT
         ACAACAGTCTTCTCCCTTCCCTCTATACCAGTGGTCCTCAACCCCTGGGCTGCAGACAGG

32193    TAAATATCTAACTCTTTCTTTTTCTTATTTTGGAATTGCAAGTCTACATATTTGTTTGAT
         TTTACAACAGTCTTCTCCCTTCCCTCTATACCAGTGGTCCTCAACCCCTGGGCTGCAGAC
         AGGTACCAGTCCATGGCCTGTTAGGAACGAGGCCACGCAACTGGAGATGAATAGCCAGCG
         AGCAAGCATTACTGCCTGAGCAATGCTTCCTGTCAGATCAGTGGCAGCGTTAGATTCTCA
         TAGGAGCACAAACCCCACTGTGAACCGCGCATGCAAAGGATTTAGGTTGCATGCTCCTTA
         [T,G]
         GAGAATCTAATGCCTGATGATCTGAGGTGGAACAGTTTTATCCCCAAACCATCCCCACCA
         CTGATTCCACCCCAACTCTGCCCCATCCATGGAAAAATTGTCTTCCATGAAACTGGTCCC
         TGGTGCCAAAAAGGTTGGGGACCACTGCTCTATACCCTAAACTGTGTTGTAGCTGACTTT
         TAAAGGCAAATACATTATGATTAATTTTGGAGGTGTTCTTGATAATTCTTCTAAAGACAT
```

FIGURE 3T

```
        CAAAGGCTATTATTGAGAAAAGGTTGATGATTCTTATTCCAGAGTTAGCAGCTTGTGTTA
32341   GAGGCCACGCAACTGGAGATGAATAGCCAGCGAGCAAGCATTACTGCCTGAGCAATGCTT
        CCTGTCAGATCAGTGGCAGCGTTAGATTCTCATAGGAGCACAAACCCCACTGTGAACCGC
        GCATGCAAAGGATTTAGGTTGCATGCTCCTTATGAGAATCTAATGCCTGATGATCTGAGG
        TGGAACAGTTTTATCCCCAAACCATCCCCACCACTGATTCCACCCCAACTCTGCCCCATC
        CATGGAAAAATTGTCTTCCATGAAACTGGTCCCTGGTGCCAAAAAGGTTGGGGACCACTG
        [G,A,C]
        TCTATACCCTAAACTGTGTTGTAGCTGACTTTTAAAGGCAAATACATTATGATTAATTTT
        GGAGGTGTTCTTGATAATTCTTCTAAAGACATCAAAGGCTATTATTGAGAAAAGGTTGAT
        GATTCTTATTCCAGAGTTAGCAGCTTGTGTTAGCCCACCATACTGGGAAAAAAGCCTCTG
        TCCCTGGATTTGCTGGTAAGTTCGTGAGAGGTTAGATGTATGCTTCTTTTTGTGTGAAAT
        AAAGAAATAATCCACATAAAAAAATATGCACTCAGGAAAATCTTGAGGGAGTTTTTGCTC
32561   CACCCCAACTCTGCCCCATCCATGGAAAAATTGTCTTCCATGAAACTGGTCCCTGGTGCC
        AAAAAGGTTGGGGACCACTGCTCTATACCCTAAACTGTGTTGTAGCTGACTTTTAAAGGC
        AAATACATTATGATTAATTTTGGAGGTGTTCTTGATAATTCTTCTAAAGACATCAAAGGC
        TATTATTGAGAAAAGGTTGATGATTCTTATTCCAGAGTTAGCAGCTTGTGTTAGCCCACC
        ATACTGGGAAAAAAGCCTCTGTCCCTGGATTTGCTGGTAAGTTCGTGAGAGGTTAGATGT
        [A,G]
        TGCTTCTTTTTGTGTGAAATAAAGAAATAATCCACATAAAAAAATATGCACTCAGGAAAA
        TCTTGAGGGAGTTTTTGCTCCGGGTGTGTCTCCACACCTCCCGGGGAAGATTGCCATCCA
        ACTCACACCCATTTACCTCTAAATGAAGCATGAAGATACAGCCCAAATCATTAGTTCTCT
        GGTCTCTTCTTTGAAACTTCCACATGCAGCTCTGACATGACTGCATAATTGTGGAGGATA
        AAAACAGTTTTAAATCAAAGAGTCCTGGCTTCAAACTTCAGTTTCAATTCACACCAGCTT
32601   TGAAACTGGTCCCTGGTGCCAAAAAGGTTGGGGACCACTGCTCTATACCCTAAACTGTGT
        TGTAGCTGACTTTTAAAGGCAAATACATTATGATTAATTTTGGAGGTGTTCTTGATAATT
        CTTCTAAAGACATCAAAGGCTATTATTGAGAAAAGGTTGATGATTCTTATTCCAGAGTTA
        GCAGCTTGTGTTAGCCCACCATACTGGGAAAAAAGCCTCTGTCCCTGGATTTGCTGGTAA
        GTTCGTGAGAGGTTAGATGTATGCTTCTTTTTGTGTGAAATAAAGAAATAATCCACATAA
        [-,A]
        AAAATATGCACTCAGGAAAATCTTGAGGGAGTTTTTGCTCCGGGTGTGTCTCCACACCTC
        CCGGGGAAGATTGCCATCCAACTCACACCCATTTACCTCTAAATGAAGCATGAAGATACA
        GCCCAAATCATTAGTTCTCTGGTCTCTTCTTTGAAACTTCCACATGCAGCTCTGACATGA
        CTGCATAATTGTGGAGGATAAAAACAGTTTTAAATCAAAGAGTCCTGGCTTCAAACTTCA
        GTTTCAATTCACACCAGCTTTGCTACCTTAACTAATGTCACTTAGTATCACCAGTGTTTA
32642   TCTATACCCTAAACTGTGTTGTAGCTGACTTTTAAAGGCAAATACATTATGATTAATTTT
        GGAGGTGTTCTTGATAATTCTTCTAAAGACATCAAAGGCTATTATTGAGAAAAGGTTGAT
        GATTCTTATTCCAGAGTTAGCAGCTTGTGTTAGCCCACCATACTGGGAAAAAAGCCTCTG
        TCCCTGGATTTGCTGGTAAGTTCGTGAGAGGTTAGATGTATGCTTCTTTTTGTGTGAAAT
        AAAGAAATAATCCACATAAAAAAATATGCACTCAGGAAAATCTTGAGGGAGTTTTTGCTC
        [C,T]
        GGGTGTGTCTCCACACCTCCCGGGGAAGATTGCCATCCAACTCACACCCATTTACCTCTA
        AATGAAGCATGAAGATACAGCCCAAATCATTAGTTCTCTGGTCTCTTCTTTGAAACTTCC
        ACATGCAGCTCTGACATGACTGCATAATTGTGGAGGATAAAAACAGTTTTAAATCAAAGA
        GTCCTGGCTTCAAACTTCAGTTTCAATTCACACCAGCTTTGCTACCTTAACTAATGTCAC
        TTAGTATCACCAGTGTTTAAATTTCCCTTGAGAATTTTCAAAGAAATGCAGAACAATGCA
32794   GCCCACCATACTGGGAAAAAAGCCTCTGTCCCTGGATTTGCTGGTAAGTTCGTGAGAGGT
        TAGATGTATGCTTCTTTTTGTGTGAAATAAAGAAATAATCCACATAAAAAAATATGCACT
        CAGGAAAATCTTGAGGGAGTTTTTGCTCCGGGTGTGTCTCCACACCTCCCGGGGAAGATT
        GCCATCCAACTCACACCCATTTACCTCTAAATGAAGCATGAAGATACAGCCCAAATCATT
        AGTTCTCTGGTCTCTTCTTTGAAACTTCCACATGCAGCTCTGACATGACTGCATAATTGT
        [-,G]
        GAGGATAAAAACAGTTTTAAATCAAAGAGTCCTGGCTTCAAACTTCAGTTTCAATTCACA
        CCAGCTTTGCTACCTTAACTAATGTCACTTAGTATCACCAGTGTTTAAATTTCCCTTGAG
        AATTTTCAAAGAAATGCAGAACAATGCATATCTCAGAGATTTGCTGAAACTATTAAATAT
        AAGCACTATATAAATGAAAGTTATTATCCTGAAGCTTATTGTTACTGTTTTTGCTACTTT
        TGGGGTTTCTTTGAGCAGGTTTCTGGAAAAGAACAAGCAGCCAAAAATGCCATATGGATT
33071   CTCTGACATGACTGCATAATTGTGGAGGATAAAAACAGTTTTAAATCAAAGAGTCCTGGC
        TTCAAACTTCAGTTTCAATTCACACCAGCTTTGCTACCTTAACTAATGTCACTTAGTATC
        ACCAGTGTTTAAATTTCCCTTGAGAATTTTCAAAGAAATGCAGAACAATGCATATCTCAG
        AGATTTGCTGAAACTATTAAATATAAGCACTATATAAATGAAAGTTATTATCCTGAAGCT
        TATTGTTACTGTTTTTGCTACTTTTGGGGTTTCTTTGAGCAGGTTTCTGGAAAAGAACAA
        [G,A]
        CAGCCAAAAATGCCATATGGATTGACTGTGGAATCCATGCCAGAGAATGGATCTCTCCTG
        CTTTCTGCTTGTGGTTCATAGGCCATGTAAGTATTCACATTCTCTTAACCCTATTTCTCA
        AAATGGTGCCCAAGATCACCTGTGTCAGACTCAACTGGGCTATTTATTAAAATGCATTTT
        CCTAGGTCACATCATGAAGCTTGGGAATCTACAATTTTCACAAGTTTCCCAGGTGACTTT
        TATGCATTAGTAAGTTGAAGAACATGACTTCAAGCATTTAAATCACCCAAAATATTTTTG
34721   AAGATTAAATTATTTAATCCACAAATATTTATAAATTGCCTATGATGTTTCAGATCCTGG
        AAATACAAGGATGAACAAAATATAGCCCAAGGATCTTATAGCTGAGTATTTTGCTCCAAC
        AATGTGAACCTGATTTGTGTAGCCCAAAGAAACATAATCAATAAGGGCTTTTTAAATCGA
```

FIGURE 3U

```
        CATTTAAACTCCATTCTTGCCTGCCTAAAACTAATTCAGATCATCTGACTCTCTTAGTAC
        TTCAAAGCACTGGAGGAGGGAAAGTAAAATAAAATATTTACCTTTCAACAATTGTGAAGG
        [C,T]
        AGGTTTTATATTCAAAAACTAAACCACCCAAAGGCAAATTAAAATCTTAGCTTTTAAGTC
        TCTCACTCTTTTCTACAACTCAATAAGGATTTCAAAAATCTTATAATCTAGTCTCAGTGG
        AAATCCACTACACTACACTTTGAGAAGCTTGAAGCCAGTCATTTCTTTCTAAGCTTCTCA
        TTCATGTACTCTCGGGAGGCAAATTTAGATCCTTCTCTTTCCGCAAAGGCAGAGCTGAGA
        CCAATTTGTGCATGACTGCATCACCAAGCCAAAATCCGGCACAGGGCTGGCACATCATAG

35304   AGGGCTGGCACATCATAGGACCCAGTGAATATATGTTAACCATCACAACTTGCCAAGTAC
        TTTTTCTGCCAAATGGCTTTTCTCACTGCTAACCTCCTGCCAAACCTCTGCCCTAGAAAA
        CTCTCATCTAATTGCACACAAAGTTAGAGCTCTACAACCTCAGGGCCTTCACAGAATTAT
        CTCTGCCCCTCCTCACCACAGCTGACACATGACCTAAGGACACTGCTCCCTGGTGGCTCC
        TTCAAGTAGAGGGGCTGCTCTTTTTTTCACATCACCATGTGCTGAGAGGCCTGGTGGAGT
        [G,A]
        GATCAGCATTCTCTTCTCCTGATACTACCAATGATCCTTCTCTTCTCAGAAACTTACACA
        AACTGGTTGCACTCTTATTTTATTGCTATCGTGCACTGACCTTCAGATAATTTCCTGGTA
        TCCGGTTCATGATTCTTTATTCCCCTCCAACTCTTGCCATCATTCTGAGTGAATTCAAAG
        TCCATGTGTGAGAGTCACCTAACAATGTATCTTCACAGTTCCTTGTTCTCTGTTCTACTA
        AACCTCATCTCAACTCCTCTTTAGCAGATTTCTCCTGTAGCCATCCTCTGGATCTCAGAA

35425   TCTCATCTAATTGCACACAAAGTTAGAGCTCTACAACCTCAGGGCCTTCACAGAATTATC
        TCTGCCCCTCCTCACCACAGCTGACACATGACCTAAGGACACTGCTCCCTGGTGGCTCCT
        TCAAGTAGAGGGGCTGCTCTTTTTTTCACATCACCATGTGCTGAGAGGCCTGGTGGAGTG
        GATCAGCATTCTCTTCTCCTGATACTACCAATGATCCTTCTCTTCTCAGAAACTTACACA
        AACTGGTTGCACTCTTATTTTATTGCTATCGTGCACTGACCTTCAGATAATTTCCTGGTA
        [T,C]
        CCGGTTCATGATTCTTTATTCCCCTCCAACTCTTGCCATCATTCTGAGTGAATTCAAAGT
        CCATGTGTGAGAGTCACCTAACAATGTATCTTCACAGTTCCTTGTTCTCTGTTCTACTAA
        ACCTCATCTCAACTCCTCTTTAGCAGATTTCTCCTGTAGCCATCCTCTGGATCTCAGAAG
        TAATGTTTTGCTGATCCTTAGACCCAGAATGTGGCCATGGACAGCAACAAGGAATGTTAG
        AAGAAGCCATCTAGCAATGTAACTTCTTAATTTCCTGTCTTCTCTCATTTCTCACCCCTA

36050   TAGCATATTTCTAGTTCCTACACAGATCTATATCATTTTAATTTATCAGTCCCTTTCCAG
        GAACACTTTCTTCACTAATTGGTCCCATCACAAATTCATCCGAACCCTCAATTTCTTGCT
        CCCTTGACCTGCTCTTCTGGAGTTCCAACCCCAAACACTCCACAGAATTAACCATCCTTT
        TTCTGAGCCACCTTGTACATCTTGCCATTGTTTATTATCATACTTATATTAATAGCATTG
        AACTGCTGCTTTTCCCTTTCCAACTTATCACTTCTATTAGCTTTCTGAAGGCAGAGACCA
        [A,G]
        GTCTAAAGTAATTTTTTTTGTTCCCCATAACCTGGTATATTGTTTGGTCAACATAATTGGT
        GCTCAATATCCCCTTGTGGAATTTGAAATTTAAATTAATGTTGCAGGTTTAGGCTGACAT
        ACAATTTTGGGTTGCAGAGAGTATCTAAACAGTACCTACTGTTGGGATAAATACTTTATT
        GTCATTGGCTACAGTTCAAACTATACATACATATATAGAGATTGGAGTAAAAACTGAGAC
        AGATAGCTCTCTGATATATTTGTAATGGTAATGAAAATGACATTTTGTTTTAAAATTTTC

36291   ACTGCTGCTTTTCCCTTTCCAACTTATCACTTCTATTAGCTTTCTGAAGGCAGAGACCAA
        GTCTAAAGTAATTTTTTTTGTTCCCCATAACCTGGTATATTGTTTGGTCAACATAATTGGT
        GCTCAATATCCCCTTGTGGAATTTGAAATTTAAATTAATGTTGCAGGTTTAGGCTGACAT
        ACAATTTTGGGTTGCAGAGAGTATCTAAACAGTACCTACTGTTGGGATAAATACTTTATT
        GTCATTGGCTACAGTTCAAACTATACATACATATATAGAGATTGGAGTAAAAACTGAGAC
        [A,G]
        GATAGCTCTCTGATATATTTGTAATGGTAATGAAAATGACATTTTGTTTTAAAATTTTCC
        CTTCATGTGTCTTATATTTTTTTTTAGCAACCCCATTAACTGACCTATATGTCGTTATGT
        ACTAATTTATTATCTCTCAAATGGTCATTGGTTAATTCCTAGGCAGGAATTGTTGTTGTT
        GTTGTTGTTGTTTAGGGCCACATTAAAGGCAAAGCTTGAGTGCACCCCAGGCAAAGTGAG
        AGGAAGAGCTGAGTAATCATTGACCACAGGCCAGCTGATGGGAATCAATCCCACCCTCTC

Chromosome map
Chromosome No: 13
```

FIGURE 3V

US 6,818,429 B2

ISOLATED HUMAN PROTEASE PROTEINS, NUCLEIC ACID MOLECULES ENCODING HUMAN PROTEASE PROTEINS, AND USES THEREOF

RELATED APPLICATION

The present application is a divisional of U.S. application Ser. No. 09/813,313, filed on Mar. 21, 2001 and issued on Mar. 19, 2002 as U.S. Pat. No. 6,455,294.

FIELD OF THE INVENTION

The present invention is in the field of protease proteins that are related to the carboxypeptidase subfamily, recombinant DNA molecules, and protein production. The present invention specifically provides novel peptides and proteins that effect protein cleavage/processing/turnover and nucleic acid molecules encoding such peptide and protein molecules, all of which are useful in the development of human therapeutics and diagnostic compositions and methods.

BACKGROUND OF THE INVENTION

The proteases may be categorized into families by the different amino acid sequences (generally between 2 and 10 residues) located on either side of the cleavage site of the protease.

The proper functioning of the cell requires careful control of the levels of important structural proteins, enzymes, and regulatory proteins. One of the ways that cells can reduce the steady state level of a particular protein is by proteolytic degradation. Further, one of the ways cells produce functioning proteins is to produce pre or pro-protein precursors that are processed by proteolytic degradation to produce an active moiety. Thus, complex and highly-regulated mechanisms have been evolved to accomplish this degradation.

Proteases regulate many different cell proliferation, differentiation, and signaling processes by regulating protein turnover and processing. Uncontrolled protease activity (either increased or decreased) has been implicated in a variety of disease conditions including inflammation, cancer, arteriosclerosis, and degenerative disorders.

An additional role of intracellular proteolysis is in the stress-response. Cells that are subject to stress such as starvation, heat-shock, chemical insult or mutation respond by increasing the rates of proteolysis. One function of this enhanced proteolysis is to salvage amino acids from non-essential proteins. These amino acids can then be re-utilized in the synthesis of essential proteins or metabolized directly to provide energy. Another function is in the repair of damage caused by the stress. For example, oxidative stress has been shown to damage a variety of proteins and cause them to be rapidly degraded.

The International Union of Biochemistry and Molecular Biology (IUBMB) has recommended to use the term peptidase for the subset of peptide bond hydrolases ( Subclass E.C 3.4.). The widely used term protease is synonymous with peptidase. Peptidases comprise two groups of enzymes: the endopeptidases and the exopeptidases, which cleave peptide bonds at points within the protein and remove amino acids sequentially from either N or C-terminus respectively. The term proteinase is also used as a synonym word for endopeptidase and four mechanistic classes of proteinases are recognized by the IUBMB: two of these are described below (also see: *Handbook of Proteolytic Enzymes* by Barrett, Rawlings, and Woessner AP Press, NY 1998). Also, for a review of the various uses of proteases as drug targets, see: Weber M, Emerging treatments for hypertension: potential role for vasopeptidase inhibition; Am J Hypertens 1999 Nov;12(11 Pt 2):139S–147S; Kentsch M, Otter W, Novel neurohormonal modulators in cardiovascular disorders. The therapeutic potential of endopeptidase inhibitors, Drugs R D 1999 Apr; 1 (4):331–8; Scarborough R M, Coagulation factor Xa: the prothrombinase complex as an emerging therapeutic target for small molecule inhibitors, J Enzym Inhib 1998;14(1):15–25; Skotnicki J S, et al., Design and synthetic considerations of matrix metalloproteinase inhibitors, Ann N Y Acad Sci 1999 Jun 30;878:61–72; McKerrow J H, Engel J C, Caffrey C R, Cysteine protease inhibitors as chemotherapy for parasitic infections, Bioorg Med Chem 1999 Apr;7(4):639–44; Rice K D, Tanaka R D, Katz B A, Numerof R P, Moore W R, Inhibitors of tryptase for the treatment of mast cell-mediated diseases, Curr Pharm Des 1998 Oct;4(5):381–96; Materson B J, Will angiotensin converting enzyme genotype, receptor mutation identification, and other miracles of molecular biology permit reduction of NNT Am J Hypertens 1998 Aug;11(8 Pt 2):138S–142S Serine Proteases The serine proteases (SP) are a large family of proteolytic enzymes that include the digestive enzymes, trypsin and chymotrypsin, components of the complement cascade and of the blood-clotting cascade, and enzymes that control the degradation and turnover of macromolecules of the extracellular matrix. SP are so named because of the presence of a serine residue in the active catalytic site for protein cleavage. SP have a wide range of substrate specificities and can be subdivided into subfamilies on the basis of these specificities. The main sub-families are trypases (cleavage after arginine or lysine), aspases (cleavage after aspartate), chymases (cleavage after phenylalanine or leucine), metases (cleavage after methionine), and serases (cleavage after serine).

A series of six SP have been identified in murine cytotoxic T-lymphocytes (CTL) and natural killer (NK) cells. These SP are involved with CTL and NK cells in the destruction of virally transformed cells and tumor cells and in organ and tissue transplant rejection (Zunino, S. J. et al. (1990) J. Immunol. 144:2001–9; Sayers, T. J. et al. (1994) J. Immunol. 152:2289–97). Human homologs of most of these enzymes have been identified (Trapani, J. A. et al. (1988) Proc. Natl. Acad. Sci. 85:6924–28; Caputo, A. et al. (1990) J. Immunol. 145:737–44). Like all SP, the CTL-SP share three distinguishing features: 1) the presence of a catalytic triad of histidine, serine, and aspartate residues which comprise the active site; 2) the sequence glycine followed by asporfate followed by serine followed by 2 glycines followed by proline which contains the active site serine; and 3) an N-terminal two isoleveines followed by two glycines sequence which characterizes the mature SP.

The SP are secretory proteins which contain N-terminal signal peptides that serve to export the immature protein across the endoplasmic reticulum and are then cleaved (von Heijne (1986) Nuc. Acid. Res. 14:5683–90). Differences in these signal sequences provide one means of distinguishing individual SP. Some SP, particularly the digestive enzymes, exist as inactive precursors or preproenzymes, and contain a leader or activation peptide sequence 3' of the signal peptide. This activation peptide may be 2–12 amino acids in length, and it extends from the cleavage site of the signal peptide to the N-terminal two isoleviens followed by two glycines sequence of the active, mature protein. Cleavage of this sequence activates the enzyme. This sequence varies in different SP according to the biochemical pathway and/or its substrate (Zunino et al, supra; Sayers et al, supra). Other features that distinguish various SP are the presence or absence of N-linked glycosylation sites that provide membrane anchors, the number and distribution of cysteine residues that determine the secondary structure of the SP, and the sequence of a substrate binding sites such as S'. The S' substrate binding region is defined by residues extending from approximately +17 to +29 relative to the N-terminal I (+1). Differences in this region of the molecule are believed to determine SP substrate specificities (Zunino et al, supra).

Trypsinogens

The trypsinogens are serine proteases secreted by exocrine cells of the pancreas (Travis J and Roberts R. Biochemistry 1969; 8: 2884–9; Mallory P and Travis J, Biochemistry 1973; 12: 2847–51). Two major types of trypsinogen isoenzymes have been characterized, trypsinogen-1, also called cationic trypsinogen, and trypsinogen-2 or anionic trypsinogen. The trypsinogen proenzymes are activated to trypsins in the intestine by enterokinase, which removes an activation peptide from the N-terminus of the trypsinogens. The trypsinogens show a high degree of sequence homology, but they can be separated on the basis of charge differences by using electrophoresis or ion exchange chromatography. The major form of trypsinogen in the pancreas and pancreatic juice is trypsinogen-1 (Guy CO et al., Biochem Biophys Res Commun 1984; 125: 516–23). In serum of healthy subjects, trypsinogen-1 is also the major form, whereas in patients with pancreatitis, trypsinogen-2 is more strongly elevated (Itkonen et al., J Lab Clin Med 1990; 115:712–8). Trypsinogens also occur in certain ovarian tumors, in which trypsinogen-2 is the major form (Koivunen et al., Cancer Res 1990; 50: 2375–8). Trypsin-1 in complex with alpha-1-antitrypsin, also called alpha-1-antiprotease, has been found to occur in serum of patients with pancreatitis (Borgstrom A and Ohlsson K, Scand J Clin Lab Invest 1984; 44: 381–6) but determination of this complex has not been found useful for differentiation between pancreatic and other gastrointestinal diseases (Borgstrom et al., Scand J Clin Lab Invest 1989; 49:757–62).

Trypsinogen-1 and -2 are closely related immunologically (Kimland et al., Clin Chim Acta 1989; 184: 31–46; Itkonen et al., 1990), but by using monoclonal antibodies (Itkonen et al., 1990) or by absorbing polyclonal antisera (Kimland et al., 1989) it is possible to obtain reagents enabling specific measurement of each form of trypsinogen.

When active trypsin reaches the blood stream, it is inactivated by the major trypsin inhibitors alpha-2-macroglobulin and alpha-1-antitrypsin (AAT). AAT is a 58 kilodalton serine protease inhibitor synthesized in the liver and is one of the main protease inhibitors in blood. Whereas complexes between trypsin-1 and AAT are detectable in serum (Borgstrom and Ohlsson, 1984) the complexes with alpha-2-macroglobulin are not measurable with antibody-based assays (Ohlsson K, Acta Gastroenterol Belg 1988; 51: 3–12).

Inflammation of the pancreas or pancreatitis may be classified as either acute or chronic by clinical criteria. With treatment, acute pancreatitis can often be cured and normal function restored. Chronic pancreatitis often results in permanent damage. The precise mechanisms which trigger acute inflammation are not understood. However, some causes in the order of their importance are alcohol ingestion, biliary tract disease, post-operative trauma, and hereditary pancreatitis. One theory provides that autodigestion, the premature activation of proteolytic enzymes in the pancreas rather than in the duodenum, causes acute pancreatitis. Any number of other factors including endotoxins, exotoxins, viral infections, ischemia, anoxia, and direct trauma may activate the proenzymes. In addition, any internal or external blockage of pancreatic ducts can also cause an accumulation of pancreatic juices in the pancreas resulting cellular damage.

Anatomy, physiology, and diseases of the pancreas are reviewed, inter alia, in Guyton A C (1991) Textbook of Medical Physiology, W B Saunders Co, Philadelphia Pa.; Isselbacher K J et al (1994) Harrison's Principles of Internal Medicine, McGraw-Hill, New York City; Johnson K E (1991) Histology and Cell Biology, Harwal Publishing, Media Pa.; and The Merck Manual of Diagnosis and Therapy (1992) Merck Research Laboratories, Rahway N.J.

Metalloprotease

The metalloproteases may be one of the older classes of proteinases and are found in bacteria, fungi as well as in higher organisms. They differ widely in their sequences and their structures but the great majority of enzymes contain a zinc atom which is catalytically active. In some cases, zinc may be replaced by another metal such as cobalt or nickel without loss of the activity. Bacterial thermolysin has been well characterized and its crystallographic structure indicates that zinc is bound by two histidines and one glutamic acid. Many enzymes contain the sequence histidine followed by glutamatic followed by any two amino acids followed by histidine, which provides two histidine ligands for the zinc whereas the third ligand is either a glutamic acid (thermolysin, neprilysin, alanyl aminopeptidase) or a histidine (astacin). Other families exhibit a distinct mode of binding of the Zn atom. The catalytic mechanism leads to the formation of a non covalent tetrahedral intermediate after the attack of a zinc-bound water molecule on the carbonyl group of the scissile bond. This intermediate is further decomposed by transfer of the glutamic acid proton to the leaving group.

Metalloproteases contain a catalytic zinc metal center which participates in the hydrolysis of the peptide backbone (reviewed in Power and Harper, in Protease Inhibitors, A. J. Barrett and G. Salversen (eds.) Elsevier, Amsterdam, 1986, p. 219). The active zinc center differentiates some of these proteases from calpains and trypsins whose activities are dependent upon the presence of calcium. Examples of metalloproteases include carboxypeptidase A, carboxypeptidase B, and thermolysin.

Metalloproteases have been isolated from a number of procaryotic and eucaryotic sources, e.g. *Bacillus subtilis* (McConn et al., 1964, J. Biol. Chem. 239:3706); *Bacillus megaterium*; Serratia (Miyata et al., 1971, Agr. Biol. Chem. 35:460); *Clostridium bifermentans* (MacFarlane et al., 1992, App. Environ. Microbiol. 58:1195–1200), *Legionella pneumophila* (Moffat et al., 1994, Infection and Immunity 62:751–3). In particular, acidic metalloproteases have been isolated from broad-banded copperhead venoms (Johnson and Ownby, 1993, Int. J. Biochem. 25:267–278), rattlesnake venoms (Chlou et al., 1992, Biochem. Biophys. Res. Commun. 187:389–396) and articular cartilage (Treadwell et al., 1986, Arch. Biochem. Biophys. 251:715–723). Neutral metalloproteases, specifically those having optimal activity at neutral pH have, for example, been isolated from *Aspergillus sojae* (Sekine, 1973, Agric. Biol. Chem. 37:1945–1952). Neutral metalloproteases obtained from Aspergillus have been classified into two groups, npI and npII (Sekine, 1972, Agric. Biol. Chem. 36:207–216). So far, success in obtaining amino acid sequence information from these fungal neutral metalloproteases has been limited. An npII metalloprotease isolated from *Aspergillus oryzae* has been cloned based on amino acid sequence presented in the literature (Tatsumi et al., 1991, Mol. Gen. Genet. 228:97–103). However, to date, no npI fungal metalloprotease has been cloned or sequenced. Alkaline metalloproteases, for example, have been isolated from *Pseudomonas aeruginosa* (Baumann et al., 1993, EMBO J 12:3357–3364) and the insect pathogen *Xenorhabdus luminescens* (Schmidt et al., 1998, Appl. Environ. Microbiol. 54:2793–2797).

Metalloproteases have been devided into several distinct families based primarily on activity and sturcture: 1) water nucleophile; water bound by single zinc ion ligated to two His (within the motif histidine followed by glutomate followed by any 2 amino acids followed by histidine) and Glu, His or Asp; 2) water nucleophile; water bound by single zinc ion ligated to His, Glu (within the motif histidine followed by any 2 amino acids followed by glutamate) and His; 3) water nucleophile; water bound by single zinc ion ligated to His, Asp and His; 4) Water nucleophile; water bound by single zinc ion ligated to two His (within the motif histidine followed by any two amino acids followed by glutamate followed by histidine) and Glu and 5) water nucleophile; water bound by two zinc ions ligated by Lys, Asp, Asp, Asp, Glu.

Examples of members of the metalloproteinase family include, but are not limited to, membrane alanyl aminopeptidase (*Homo sapiens*), germinal peptidyl-dipeptidase A (*Homo sapiens*), thimet oligopeptidase (*Rattus norvegicus*), oligopeptidase F (*Lactococcus lactis*), mycolysin (*Streptomyces cacaoi*), immune inhibitor A (*Bacillus thuringiensis*), snapalysin (*Streptomyces lividans*), leishmanolysin (*Leishmania major*), microbial collagenase (*Vibrio alginolyticus*), microbial collagenase, class I (*Clostridium perfringens*), collagenase 1 (*Homo sapiens*), serralysin (*Serratia marcescens*), fragilysin (*Bacteroides fragilis*), gametolysin (*Chlamydomonas reinhardtii*), astacin (*Astacus fluviatilis*), adamalysin (*Crotalus adamanteus*), ADAM 10 (*Bos taurus*), neprilysin (*Homo sapiens*), carboxypeptidase A (*Homo sapiens*), carboxypeptidase E (*Bos taurus*), gamma-D-glutamyl-(L)-meso-diaminopimelate peptidase I (*Bacillus sphaericus*), vanY D-Ala-D-Ala carboxypeptidase (*Enterococcus faecium*), endolysin (bacteriophage A118), pitrilysin (*Escherichia coli*), mitochondrial processing peptidase (*Saccharomyces cerevisiae*), leucyl aminopeptidase (*Bos taurus*), aminopeptidase I (*Saccharomyces cerevisiae*), membrane dipeptidase (*Homo sapiens*), glutamate carboxypeptidase (*Pseudomonas* sp.), Gly-X carboxypeptidase (*Saccharomyces cerevisiae*), O-sialoglycoprotein endopeptidase (*Pasteurella haemolytica*), beta-lytic metalloendopeptidase (*Achromobacter lyticus*), methionyl aminopeptidase I (*Escherichia coli*), X-Pro aminopeptidase (*Escherichia coli*), X-His dipeptidase (*Escherichia coli*), IgA1-specific metalloendopeptidase (*Streptococcus sanguis*), tentoxilysin (*Clostridium tetani*), leucyl aminopeptidase (*Vibrio proteolyticus*), aminopeptidase (*Streptomyces griseus*), LAP aminopeptidase (*Escherichia coli*), aminopeptidase T (*Thermus aquaticus*), hyicolysin (*Staphylococcus hyicus*), carboxypeptidase Taq (*Thermus aquaticus*), anthrax lethal factor (*Bacillus anthracis*), penicillolysin (*Penicillium citrinum*), fungalysin (*Aspergillus fumigatus*), lysostaphin (*Staphylococcus simulans*), beta-aspartyl dipeptidase (*Escherichia coli*), carboxypeptidase Ss1 (*Sulfolobus solfataricus*), FtsH endopeptidase (*Escherichia coli*), glutamyl aminopeptidase (*Lactococcus lactis*), cytophagalysin (*Cytophaga* sp.), metalloendopeptidase (vaccinia virus), VanX D-Ala-D-Ala dipeptidase (*Enterococcus faecium*), Ste24p endopeptidase (*Saccharomyces cerevisiae*), dipeptidyl-peptidase III (*Rattus norvegicus*), S2P protease (*Homo sapiens*), sporulation factor SpoIVFB (*Bacillus subtilis*), and HYBD endopeptidase (*Escherichia coli*).

Metalloproteases have been found to have a number of uses. For example, there is strong evidence that a metalloprotease is involved in the in vivo proteolytic processing of the vasoconstrictor, endothelin-1. Rat metalloprotease has been found to be involved in peptide hormone processing. One important subfamily of the metalloproteases are the matrix metalloproteases.

A number of diseases are thought to be mediated by excess or undesired metalloprotease activity or by an imbalance in the ratio of the various members of the protease family of proteins. These include: a) osteoarthritis (Woessner, et al., J. Biol.Chem. 259(6), 3633, 1984; Phadke, et al., J. Rheumatol. 10, 852, 1983), b) rheumatoid arthritis (Mullins, et al., Biochim. Biophys. Acta 695, 117, 1983; Woolley, et al., Arthritis Rheum. 20, 1231, 1977; Gravallese, et al., Arthritis Rheum. 34, 1076, 1991), c) septic arthritis (Williams, et al., Arthritis Rheum. 33, 533, 1990), d) tumor metastasis (Reich, et al., Cancer Res. 48, 3307, 1988, and Matrisian, et al., Proc. Nat'l. Acad. Sci., USA 83, 9413, 1986), e) periodontal diseases (Overall, et al., J. Periodontal Res. 22, 81, 1987), f) corneal ulceration (Burns, et al., Invest. Opthalmol. Vis. Sci. 30, 1569, 1989), g) proteinuria (Baricos, et al., Biochem. J. 254, 609, 1988), h) coronary thrombosis from atherosclerotic plaque rupture (Henney, et al., Proc. Nat'l. Acad. Sci., USA 88, 8154–8158, 1991), i) aneurysmal aortic disease (Vine, et al., Clin. Sci. 81, 233, 1991), j) birth control (Woessner, et al., Steroids 54, 491, 1989), k) dystrophobic epidermolysis bullosa (Kronberger, et al., J. Invest. Dermatol. 79, 208, 1982), and l) degenerative cartilage loss following traumatic joint injury, m) conditions leading to inflammatory responses, osteopenias mediated by MMP activity, n) tempero mandibular joint disease, o) demyelating diseases of the nervous system (Chantry, et al., J. Neurochem. 50, 688, 1988).

Aspartic Protease

Aspartic proteases have been divided into several distinct families based primarily on activity and structure. These include 1) water nucleophile; water bound by two Asp from monomer or dimer; all endopeptidases, from eukaryote organisms, viruses or virus-like organisms and 2) endopeptidases that are water nucleophile and are water bound by Asp and Asn.

Most of aspartic proteases belong to the pepsin family. The pepsin family includes digestive enzymes such as pepsin and chymosin as well as lysosomal cathepsins D and processing enzymes such as renin, and certain fungal proteases (penicillopepsin, rhizopuspepsin, endothiapepsin). A second family comprises viral proteases such as the protease from the AIDS virus (HIV) also called retropepsin. Crystallographic studies have shown that these enzymes are bibbed molecules with the active site located between two homologous lobes. Each lobe contributes one aspartate residue of the catalytically active diad of aspartates. These two aspartyl residues are in close geometric proximity in the active molecule and one aspartate is ionized whereas the second one is unionized at the optimum pH range of 2–3. Retropepsins, are monomeric, i.e carry only one catalytic aspartate and then dimerization is required to form an active enzyme.

In contrast to serine and cysteine proteases, catalysis by aspartic protease do not involve a covalent intermediate though a tetrahedral intermediate exists. The nucleophilic attack is achieved by two simultaneous proton transfer: one from a water molecule to the diad of the two carboxyl groups and a second one from the diad to the carbonyl oxygen of the substrate with the concurrent CO—NH bond cleavage. This general acid-base catalysis, which may be called a "push-pull" mechanism leads to the formation of a non covalent neutral tetrahedral intermediate.

Examples of the aspartic protease family of proteins include, but are not limited to, pepsin A (*Homo sapiens*), HIV1 retropepsin (human immunodeficiency virus type 1), endopeptidase (cauliflower mosaic virus), baciiliform virus putative protease (rice tungro baciiliform virus), aspergillopepsin II (*Aspergillus niger*), thermopsin (*Sulfolobus acidocaldarius*), nodavirus endopeptidase (flock house virus), pseudomonapepsin (*Pseudomonas* sp. 101), signal peptidase II (*Escherichia coli*), polyprotein peptidase (human spumaretrovirus), copia transposon (*Drosophila melanogaster*), SIRE-1 peptidase (*Glycine max*), retrotransposon bs1 endopeptidase (*Zea mays*), retrotransposon peptidase (*Drosophila buzzatii*), Tas retrotransposon peptidase (*Ascaris lumbricoides*), Pao retrotransposon peptidase (*Bombyx mori*), putative proteinase of Skippy retrotransposon (*Fusarium oxysporum*), tetravirus endopeptidase (*Nudaurelia capensis* omega virus), presenilin 1 (*Homo sapiens*).

Carboxypeptidase

Carboxypeptidases are proteases that function in many physiological processes. These proteases remove a wide range of carboxyl-terminal amino acids, and in doing so are able to activate, inactivate, and modulate enzyme and peptide hormone activity. Many active forms of mammalian carboxypeptidases are located in lysosomes where they regulate intracellular protein processing, degradation and turnover. In plants and insects carboxypeptidases play a role in posttranslational protein modifications including mobilization of storage proteins and hormone activation.

Carboxypeptidase activities are regulated either by endogenous protein inhibitors or by enzymatic cleavage of a segment of a propeptide to release the active carboxypeptidase. Carboxypeptidases A and B (CPA and CPB, respectively) are pancreatic zinc-containing proteolytic enzymes which catalyze the hydrolysis of the carboxyl-terminal peptide bond in polypeptide chains. When transcribed in rat brain and other nonpancreatic tissues, CPA is unable to function as a protease (Normant, E. et al. (1995) J. Biol. Chem. 270: 20543–20549). This inability to function as a protease has been attributed to the presence of tissue-specific, endogenous protein inhibitors such as tissue carboxypeptidase inhibitor (TCI) or latexin (Normant, E. et al. (1995) Proc. Natl. Acad. Sci. 92: 12225–12229; Hatanaka, Y. et al. (1994) Eur. J. Neurosci. 6: 973–982).

Latexin and TCI are 222 and 223 amino acids in length, respectively. They contain several potential phosphorylation sites, but they do not show a membrane-specific signal peptide sequence (Normant et al., supra; Hatanaka et al., supra). TCI is a non-competitive, nearly irreversible, and potent inhibitor of CPA; it is less potent against CPB and does not act on various other proteases. TCI and latexin are both expressed and localized in the cytosol of a number of tissues including brain, lung, or digestive tract. It has been suggested that TCI or latexin may function in regulating tissue-specific, cytosolic protein degradation (Normant et al., supra).

Eaton et al purified a novel human plasma carboxypeptidase B (designated pCPB protein) that has an apparent Mr of 60,000. The deduced amino acid sequence reveals a primary translation product of 423 amino acids that is very similar to carboxypeptidase A and B and consists of a 22-amino acid signal peptide, a 92-amino acid activation peptide, and a 309-amino acid catalytic domain. This protein shows 44 and 40% similarity to rat procarboxypeptidase B and human mast cell procarboxypeptidase. The presence of aspartic acid at position 257 of the catalytic domain suggests that this protein is a basic carboxypeptidase. When activated by trypsin, it hydrolyzes carboxypeptidase B substrates, hippuryl-Arg and hippuryl-Lys, but not carboxypeptidase A substrates, and it is inhibited by the specific carboxypeptidase B inhibitor (DL-5-guanidinoethyl)mercaptosuccinic acid. Tsai and Drayna (1992) used PCR to identify the presence of the plasma carboxypeptidase B gene in somatic hybrid cell lines which is called carboxypeptidase B2 (CPB2), also called carboxypeptidase U (CPU). It is an unstable basic carboxypeptidase that circulates in human plasma in its proenzyme form. The most likely physiologic activator of pro-CPU is the thrombin-thrombomodulin complex. Vanhoof et al. (1996) noted that pro-CPU exhibits affinity for plasminogen and can be converted to its active form through the action of thrombin and plasmin. CPB2 gene is located on human chromosome 13. To regionalize the assignment of the gene on chromosome 13, Vanhoof et al. (1996) used fluorescence in situ hybridization. They found that it is localized to 13q14.11.

For a review of the carboxypeptidase, see Eaton et al., J. Biol. Chem. 266: 21833–21838, 1991; Tsai et al., Genomics 14: 549–550, 1992; Vanhoof et al., Genomics 38: 454–455, 1996; Pascual et al., Eur J Biochem Feb 15;179(3):609–16, 1989;

The protein of the present invention has a substantial similarity to the carboxypeptidase B as set forth above. Protease proteins, particularly members of the carboxypeptidase subfamily, are a major target for drug action and development. Accordingly, it is valuable to the field of pharmaceutical development to identify and characterize previously unknown members of this subfamily of protease proteins. The present invention advances the state of the art by providing a previously unidentified human protease proteins that have homology to members of the carboxypeptidase subfamily.

SUMMARY OF THE INVENTION

The present invention is based in part on the identification of amino acid sequences of human protease peptides and proteins that are related to the carboxypeptidase subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate protease activity in cells and tissues that express the protease. Experimental data as provided in FIG. 1 indicates expression in fetal brain, liver, hepatocellular carcinoma and whole liver.

DESCRIPTION OF THE FIGURE SHEETS

FIG. 1 provides the nucleotide sequence of a cDNA molecule or transcript sequence that encodes the protease protein of the present invention. (SEQ ID NO:1) In addition, structure and functional information is provided, such as ATG start, stop and tissue distribution, where available, that allows one to readily determine specific uses of inventions based on this molecular sequence. Experimental data as provided in FIG. 1 indicates expression in fetal brain, liver, hepatocellular carcinoma and whole liver.

FIG. 2 provides the predicted amino acid sequence of the protease of the present invention. (SEQ ID NO:2) In addition structure and functional information such as protein family, function, and modification sites is provided where available, allowing one to readily determine specific uses of inventions based on this molecular sequence.

FIG. 3 provides genomic sequences that span the gene encoding the protease protein of the present invention. (SEQ ID NO:3) In addition structure and functional information, such as intron/exon structure, promoter location, etc., is provided where available, allowing one to readily determine specific uses of inventions based on this molecular sequence. As illustrated in FIG. 3, SNPs, including insertion/deletion variants ("indels"), were identified at 40 different nucleotide positions.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a protease protein or part of a protease protein and are related to the carboxypeptidase subfamily. Utilizing these sequences, additional genomic sequences were assembled and transcript and/or cDNA sequences were isolated and characterized. Based on this analysis, the present invention provides amino acid sequences of human protease peptides and proteins that are related to the carboxypeptidase subfamily, nucleic acid sequences in the form of transcript sequences, cDNA sequences and/or genomic sequences that encode these protease peptides and proteins, nucleic acid variation (allelic information), tissue distribution of expression, and information about the closest art known protein/peptide/domain that has structural or sequence homology to the protease of the present invention.

In addition to being previously unknown, the peptides that are provided in the present invention are selected based on their ability to be used for the development of commercially important products and services. Specifically, the present peptides are selected based on homology and/or structural relatedness to known protease proteins of the carboxypeptidase subfamily and the expression pattern observed. Experimental data as provided in FIG. 1 indicates expression in fetal brain, liver, hepatocellular carcinoma and whole liver. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known carboxypeptidase family or subfamily of protease proteins.

Specific Embodiments

Peptide Molecules

The present invention provides nucleic acid sequences that encode protein molecules that have been identified as being members of the protease family of proteins and are related to the carboxypeptidase subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the protease peptides of the present invention, protease peptides, or peptides/proteins of the present invention.

The present invention provides isolated peptide and protein molecules that consist of, consist essentially of, or comprise the amino acid sequences of the protease peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the protease peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated protease peptide can be purified from cells that naturally express it, purified from cells that have been altered to express it (recombinant), or synthesized using known protein synthesis methods. Experimental data as provided in FIG. 1 indicates expression in fetal brain, liver, hepatocellular carcinoma and whole liver. For example, a nucleic acid molecule encoding the protease peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the protease peptides of the present invention are the naturally occurring mature proteins. A brief description of how various types of these proteins can be made/isolated is provided below.

The protease peptides of the present invention can be attached to heterologous sequences to form chimeric or fusion proteins. Such chimeric and fusion proteins comprise a protease peptide operatively linked to a heterologous protein having an amino acid sequence not substantially homologous to the protease peptide. "Operatively linked" indicates that the protease peptide and the heterologous protein are fused in-frame. The heterologous protein can be fused to the N-terminus or C-terminus of the protease peptide.

In some uses, the fusion protein does not affect the activity of the protease peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant protease peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., Current Protocols in Molecular Biology, 1992). Moreover, many expression vectors are commercially available that already encode a fusion moiety (e.g., a GST protein). A protease peptide-encoding nucleic acid can be cloned into such an expression vector such that the fusion moiety is linked in-frame to the protease peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the protease peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of the length of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). In a preferred embodiment, the percent identity between two amino acid sequences is determined using the Needleman and Wunsch (J. Mol. Biol. (48):444–453 (1970)) algorithm which has been incorporated into the GAP program in the GCG software package (available at .gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at .gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the protease peptides of the present invention as well as being encoded by the same genetic locus as the protease peptide provided herein. As indicated by the data presented in FIG. 3, the map position was determined to be on chromosome 13 by ePCR.

Allelic variants of a protease peptide can readily be identified as being a human protein having a high degree (significant) of sequence homology/identity to at least a portion of the protease peptide as well as being encoded by the same genetic locus as the protease peptide provided herein. Genetic locus can readily be determined based on the genomic information provided in FIG. 3, such as the genomic sequence mapped to the reference human. As indicated by the data presented in FIG. 3, the map position was determined to be on chromosome 13 by ePCR. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a protease peptide encoding nucleic acid molecule under stringent conditions as more fully described below.

FIG. 3 provides information on SNPs that have been identified in a gene encoding the transporter protein of the present invention. 40 SNP variants were found, including 5 indels (indicated by a "-") and 1 SNPs in exons, of which 5 of these cause changes in the amino acid sequence (i.e., nonsynonymous SNPs). SNPs, identified at different nucleotide positions in introns and regions 5' and 3' of the ORF, may affect control/regulatory elements.

Paralogs of a protease peptide can readily be identified as having some degree of significant sequence homology/ identity to at least a portion of the protease peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a protease peptide encoding nucleic acid molecule under moderate to stringent conditions as more fully described below.

Orthologs of a protease peptide can readily be identified as having some degree of significant sequence homology/ identity to at least a portion of the protease peptide as well as being encoded by a gene from another organism. Preferred orthologs will be isolated from mammals, preferably primates, for the development of human therapeutic targets and agents. Such orthologs will be encoded by a nucleic acid sequence that will hybridize to a protease peptide encoding nucleic acid molecule under moderate to stringent conditions, as more fully described below, depending on the degree of relatedness of the two organisms yielding the proteins. As indicated by the data presented in FIG. 3, the map position was determined to be on chromosome 13 by ePCR.

FIG. 3 provides information on SNPs that have been identified in a gene encoding the transporter protein of the present invention. 40 SNP variants were found, including 5 indels (indicated by a "-") and 1 SNPs in exons, of which 5 of these cause changes in the amino acid sequence (i.e., nonsynonymous SNPs). SNPs, identified at different nucleotide positions in introns and regions 5' and 3' of the ORF, may affect control/regulatory elements.

Non-naturally occurring variants of the protease peptides of the present invention can readily be generated using recombinant techniques. Such variants include, but are not limited to deletions, additions and substitutions in the amino acid sequence of the protease peptide. For example, one class of substitutions are conserved amino acid substitution. Such substitutions are those that substitute a given amino acid in a protease peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant protease peptides can be fully functional or can lack function in one or more activities, e.g. ability to bind substrate, ability to cleave substrate, ability to participate in a signaling pathway, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as protease activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the protease peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a protease peptide. Such fragments can be chosen based on the ability to retain one or more of the biological activities of the protease peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the protease peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in protease peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. NY. Acad. Sci.* 663:48–62 (1992)).

Accordingly, the protease peptides of the present invention also encompass derivatives or analogs in which a substituted amino acid residue is not one encoded by the genetic code, in which a substituent group is included, in which the mature protease peptide is fused with another compound, such as a compound to increase the half-life of the protease peptide (for example, polyethylene glycol), or in which the additional amino acids are fused to the mature protease peptide, such as a leader or secretory sequence or a sequence for purification of the mature protease peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a protease-effector protein interaction or protease-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

UTILITY_UTILITY

The potential uses of the peptides of the present invention are based primarily on the source of the protein as well as the class/action of the protein. For example, proteases isolated from humans and their human/mammalian orthologs serve as targets for identifying agents for use in mammalian therapeutic applications, e.g. a human drug, particularly in modulating a biological or pathological response in a cell or tissue that expresses the protease. Experimental data as provided in FIG. 1 indicates that protease proteins of the present invention are expressed in the fetal brain, liver, hepatocellular carcinoma by a virtual northern blot. In addition, PCR-based tissue screening panel indicates expression in whole liver. A large percentage of pharmaceutical agents are being developed that modulate the activity of protease proteins, particularly members of the carboxypeptidase subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in fetal brain, liver, hepatocellular carcinoma and whole liver. Such uses can readily be determined using the information provided herein, that which is known in the art, and routine experimentation.

The proteins of the present invention (including variants and fragments that may have been disclosed prior to the present invention) are useful for biological assays related to proteases that are related to members of the carboxypeptidase subfamily. Such assays involve any of the known protease functions or activities or properties useful for diagnosis and treatment of protease-related conditions that are specific for the subfamily of proteases that the one of the present invention belongs to, particularly in cells and tissues that express the protease. Experimental data as provided in FIG. 1 indicates that protease proteins of the present invention are expressed in the fetal brain, liver, hepatocellular carcinoma by a virtual northern blot. In addition, PCR-based tissue screening panel indicates expression in whole liver.

The proteins of the present invention are also useful in drug screening assays, in cell-based or cell-free systems. Cell-based systems can be native, i.e., cells that normally express the protease, as a biopsy or expanded in cell culture. Experimental data as provided in FIG. 1 indicates expression in fetal brain, liver, hepatocellular carcinoma and whole liver. In an alternate embodiment, cell-based assays involve recombinant host cells expressing the protease protein.

The polypeptides can be used to identify compounds that modulate protease activity of the protein in its natural state or an altered form that causes a specific disease or pathology associated with the protease. Both the proteases of the present invention and appropriate variants and fragments can be used in high-throughput screens to assay candidate compounds for the ability to bind to the protease. These compounds can be further screened against a functional protease to determine the effect of the compound on the protease activity. Further, these compounds can be tested in animal or invertebrate systems to determine activity/effectiveness. Compounds can be identified that activate (agonist) or inactivate (antagonist) the protease to a desired degree.

Further, the proteins of the present invention can be used to screen a compound for the ability to stimulate or inhibit interaction between the protease protein and a molecule that normally interacts with the protease protein, e.g. a substrate or a component of the signal pathway that the protease protein normally interacts (for example, a protease). Such assays typically include the steps of combining the protease protein with a candidate compound under conditions that allow the protease protein, or fragment, to interact with the target molecule, and to detect the formation of a complex between the protein and the target or to detect the biochemical consequence of the interaction with the protease protein and the target, such as any of the associated effects of signal transduction such as protein cleavage, cAMP turnover, and adenylate cyclase activation, etc.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for substrate binding. Other candidate compounds include mutant proteases or appropriate fragments containing mutations that affect protease function and thus compete for substrate. Accordingly, a fragment that competes for substrate, for example with a higher affinity, or a fragment that binds substrate but does not allow release, is encompassed by the invention.

The invention further includes other end point assays to identify compounds that modulate (stimulate or inhibit) protease activity. The assays typically involve an assay of events in the signal transduction pathway that indicate protease activity. Thus, the cleavage of a substrate, inactivation/activation of a protein, a change in the expression of genes that are up- or down-regulated in response to the protease protein dependent signal cascade can be assayed.

Any of the biological or biochemical functions mediated by the protease can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the protease can be assayed. Experimental data as provided in FIG. 1 indicates that protease proteins of the present invention are expressed in the fetal brain, liver, hepatocellular carcinoma by a virtual northern blot. In addition, PCR-based tissue screening panel indicates expression in whole liver.

Binding and/or activating compounds can also be screened by using chimeric protease proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a substrate-binding region can be used that interacts with a different substrate then that which is recognized by the native protease. Accordingly, a different set of signal transduction components is available as an end-point assay for activation. This allows for assays to be performed in other than the specific host cell from which the protease is derived.

The proteins of the present invention are also useful in competition binding assays in methods designed to discover compounds that interact with the protease (e.g. binding partners and/or ligands). Thus, a compound is exposed to a protease polypeptide under conditions that allow the compound to bind or to otherwise interact with the polypeptide. Soluble protease polypeptide is also added to the mixture. If the test compound interacts with the soluble protease polypeptide, it decreases the amount of complex formed or activity from the protease target. This type of assay is particularly useful in cases in which compounds are sought that interact with specific regions of the protease. Thus, the soluble polypeptide that competes with the target protease region is designed to contain peptide sequences corresponding to the region of interest.

To perform cell free drug screening assays, it is sometimes desirable to immobilize either the protease protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of protease-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a protease-binding protein and a candidate compound are incubated in the protease protein-presenting wells and the amount of complex trapped in the well can be quantitated. Methods for detecting such complexes, in addition to those described above for the GST-immobilized complexes, include immunodetection of complexes using antibodies reactive with the protease protein target molecule, or which are reactive with protease protein and compete with the target molecule, as well as enzyme-linked assays which rely on detecting an enzymatic activity associated with the target molecule.

Agents that modulate one of the proteases of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of protease protein activity identified according to these drug screening assays can be used to treat a subject with a disorder mediated by the protease pathway, by treating cells or tissues that express the protease. Experimental data as provided in FIG. 1 indicates expression in fetal brain, liver, hepatocellular carcinoma and whole liver. These methods of treatment include the steps of administering a modulator of protease activity in a pharmaceutical composition to a subject in need of such treatment, the modulator being identified as described herein.

In yet another aspect of the invention, the protease proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with the protease and are involved in protease activity. Such protease-binding proteins are also likely to be involved in the propagation of signals by the protease proteins or protease targets as, for example, downstream elements of a protease-mediated signaling pathway. Alternatively, such protease-binding proteins are likely to be protease inhibitors.

The two-hybrid system is based on the modular nature of most transcription factors, which consist of separable DNA-binding and activation domains. Briefly, the assay utilizes two different DNA constructs. In one construct, the gene that codes for a protease protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a protease-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the protease protein.

This invention further pertains to novel agents identified by the above-described screening assays. Accordingly, it is within the scope of this invention to further use an agent identified as described herein in an appropriate animal model. For example, an agent identified as described herein (e.g., a protease-modulating agent, an antisense protease nucleic acid molecule, a protease-specific antibody, or a protease-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The protease proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in fetal brain, liver, hepatocellular carcinoma and whole liver. The method involves contacting a biological sample with a compound capable of interacting with the protease protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered protease activity in cell-based or cell-free assay, alteration in substrate or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (Clin. Exp. Pharmacol. Physiol. 23(10–11):983–985 (1996)), and Linder, M. W. (Clin. Chem. 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the protease protein in which one or more of the protease functions in one population is different from those in another population. The peptides thus allow a target to ascertain a genetic predisposition that can affect treatment modality. Thus, in a ligand-based treatment, polymorphism may give rise to amino terminal extracellular domains and/or other substrate-binding regions that are more or less active in substrate binding, and protease activation. Accordingly, substrate dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in fetal brain, liver, hepatocellular carcinoma and whole liver. Accordingly, methods for treatment include the use of the protease protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or F(ab')$_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the protease proteins. Antibodies can be prepared from any region of the peptide as described herein. However, preferred regions will include those involved in function/activity and/or protease/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that protease proteins of the present invention are expressed in the fetal brain, liver, hepatocellular carcinoma by a virtual northern blot. In addition, PCR-based tissue screening panel indicates expression in whole liver. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in fetal brain, liver, hepatocellular carcinoma and whole liver. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in fetal brain, liver, hepatocellular carcinoma and whole liver. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in fetal brain, liver, hepatocellular carcinoma and whole liver. Thus, where a specific protein has been correlated with expression in a specific tissue, antibodies that are specific for this protein can be used to identify a tissue type.

The antibodies are also useful for inhibiting protein function, for example, blocking the binding of the protease peptide to a binding partner such as a substrate. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a protease peptide or protein of the present invention (cDNA, transcript and genomic sequence). Such nucleic acid molecules will consist of, consist essentially of, or comprise a nucleotide sequence that encodes one of the protease peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5 KB, 4 KB, 3 KB, 2 KB, or 1 KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprises several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the protease peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the protease proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45C, followed by one or more washes in 0.2× SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. As illustrated in FIG. 3, SNPs, including insertion/deletion variants ("indels"), were identified at 40 different nucleotide positions.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 13 by ePCR.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that protease proteins of the present invention are expressed in the fetal brain, liver, hepatocellular carcinoma by a virtual northern blot. In addition, PCR-based tissue screening panel indicates expression in whole liver. Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in protease protein expression relative to normal results.

In vitro techniques for detection of mRNA include Northern hybridizations and in situ hybridizations. In vitro techniques for detecting DNA includes Southern hybridizations and in situ hybridization.

Probes can be used as a part of a diagnostic test kit for identifying cells or tissues that express a protease protein, such as by measuring a level of a protease-encoding nucleic acid in a sample of cells from a subject e.g., mRNA or genomic DNA, or determining if a protease gene has been mutated. Experimental data as provided in FIG. 1 indicates that protease proteins of the present invention are expressed in the fetal brain, liver, hepatocellular carcinoma by a virtual northern blot. In addition, PCR-based tissue screening panel indicates expression in whole liver.

Nucleic acid expression assays are useful for drug screening to identify compounds that modulate protease nucleic acid expression.

The invention thus provides a method for identifying a compound that can be used to treat a disorder associated with nucleic acid expression of the protease gene, particularly biological and pathological processes that are mediated by the protease in cells and tissues that express it. Experimental data as provided in FIG. 1 indicates expression in fetal brain, liver, hepatocellular carcinoma and whole liver. The method typically includes assaying the ability of the compound to modulate the expression of the protease nucleic acid and thus identifying a compound that can be used to treat a disorder characterized by undesired protease nucleic acid expression. The assays can be performed in cell-based and cell-free systems. Cell-based assays include cells naturally expressing the protease nucleic acid or recombinant cells genetically engineered to express specific nucleic acid sequences.

The assay for protease nucleic acid expression can involve direct assay of nucleic acid levels, such as mRNA levels, or on collateral compounds involved in the signal pathway. Further, the expression of genes that are up- or down-regulated in response to the protease protein signal pathway can also be assayed. In this embodiment the regulatory regions of these genes can be operably linked to a reporter gene such as luciferase.

Thus, modulators of protease gene expression can be identified in a method wherein a cell is contacted with a candidate compound and the expression of mRNA determined. The level of expression of protease mRNA in the presence of the candidate compound is compared to the level of expression of protease mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate protease nucleic acid expression in cells and tissues that express the protease. Experimental data as provided in FIG. 1 indicates that protease proteins of the present invention are expressed in the fetal brain, liver, hepatocellular carcinoma by a virtual northern blot. In addition, PCR-based tissue screening panel indicates expression in whole liver. Modulation includes both up-regulation (i.e. activation or agonization) or down-regulation (suppression or antagonization) or nucleic acid expression.

Alternatively, a modulator for protease nucleic acid expression can be a small molecule or drug identified using the screening assays described herein as long as the drug or small molecule inhibits the protease nucleic acid expression in the cells and tissues that express the protein. Experimental data as provided in FIG. 1 indicates expression in fetal brain, liver, hepatocellular carcinoma and whole liver.

The nucleic acid molecules are also useful for monitoring the effectiveness of modulating compounds on the expression or activity of the protease gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in protease nucleic acid expression, and particularly in qualitative changes that lead to pathology. The nucleic acid molecules can be used to detect mutations in protease genes and gene expression products such as mRNA. The nucleic acid molecules can be used as hybridization probes to detect naturally occurring genetic mutations in the protease gene and thereby to determine whether a subject with the mutation is at risk for a disorder caused by the mutation. Mutations include a deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the protease gene associated with a dysfunction provides a diagnostic tool for an active disease or susceptibility to disease when the disease results from overexpression, underexpression, or altered expression of a protease protein.

Individuals carrying mutations in the protease gene can be detected at the nucleic acid level by a variety of techniques. FIG. 3 provides information on SNPs that have been identified in a gene encoding the transporter protein of the present invention. 40 SNP variants were found, including 5 indels (indicated by a "-") and 1 SNPs in exons, of which 5 of these cause changes in the amino acid sequence (i.e., nonsynonymous SNPs). SNPs, identified at different nucleotide positions in introns and regions 5' and 3' of the ORF, may affect control/regulatory elements. As indicated by the data presented in FIG. 3, the map position was determined to be on chromosome 13 by ePCR. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a protease gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant protease gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., Science 230:1242 (1985)); Cotton et al., PNAS 85:4397 (1988); Saleeba et al., Meth. Enzymol. 217:286–295 (1992)), electrophoretic mobility of mutant and wild type nucleic acid is compared (Orita et al., PNAS 86:2766 (1989); Cotton et al., Mutat. Res. 285:125–144 (1993); and Hayashi et al., Genet. Anal. Tech. Appl. 9:73–79 (1992)), and movement of mutant or wild-type fragments in polyacrylamide gels containing a gradient of denaturant is assayed using denaturing gradient gel electrophoresis (Myers et al., Nature 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the protease gene in an individual in order to select an appropriate compound or dosage regimen for treatment.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control protease gene expression in cells, tissues, and organisms. A DNA antisense nucleic acid molecule is designed to be complementary to a region of the gene involved in transcription, preventing transcription and hence production of protease protein. An antisense RNA or DNA nucleic acid molecule would hybridize to the mRNA and thus block translation of mRNA into protease protein. FIG. 3 provides information on SNPs that have been identified in a gene encoding the transporter protein of the present invention. 40 SNP variants were found, including 5 indels (indicated by a "-") and 1 SNPs in exons, of which 5 of these cause changes in the amino acid sequence (i.e., nonsynonymous SNPs). SNPs, identified at different nucleotide positions in introns and regions 5' and 3' of the ORF, may affect control/regulatory elements.

Alternatively, a class of antisense molecules can be used to inactivate mRNA in order to decrease expression of protease nucleic acid. Accordingly, these molecules can treat a disorder characterized by abnormal or undesired protease nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the protease protein, such as substrate binding.

The nucleic acid molecules also provide vectors for gene therapy in patients containing cells that are aberrant in protease gene expression. Thus, recombinant cells, which include the patient's cells that have been engineered ex vivo and returned to the patient, are introduced into an individual where the cells produce the desired protease protein to treat the individual.

The invention also encompasses kits for detecting the presence of a protease nucleic acid in a biological sample. Experimental data as provided in FIG. 1 indicates that protease proteins of the present invention are expressed in the fetal brain, liver, hepatocellular carcinoma by a virtual northern blot. In addition, PCR-based tissue screening panel indicates expression in whole liver. For example, the kit can comprise reagents such as a labeled or labelable nucleic acid or agent capable of detecting protease nucleic acid in a biological sample; means for determining the amount of protease nucleic acid in the sample; and means for comparing the amount of protease nucleic acid in the sample with a standard. The compound or agent can be packaged in a suitable container. The kit can further comprise instructions for using the kit to detect protease protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides which cover the full length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the protease proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the protease gene of the present invention. FIG. 3 provides information on SNPs that have been identified in a gene encoding the transporter protein of the present invention. 40 SNP variants were found, including 5 indels (indicated by a "-") and 1 SNPs in exons, of which 5 of these cause changes in the amino acid sequence (i.e., nonsynonymous SNPs). SNPs, identified at different nucleotide positions in introns and regions 5' and 3' of the ORF, may affect control/regulatory elements.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein.

Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified protease gene of the present invention can be routinely identified using the sequence information disclosed herein can be readily incorporated into one of the established kit formats which are well known in the art, particularly expression arrays.

Vectors/Host Cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in prokaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual. 2nd. ed.*, Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual. 2nd. ed.*, Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enteroprotease. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J* 6:229–234 (1987)), pMFa (Kurjan et al., *Cell* 30:933–943(1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al., *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual. 2nd, ed.*, Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will. occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as proteases, appropriate secretion signals are incorporated into the vector. The signal sequence can be endogenous to the peptides or heterologous to these peptides.

Where the peptide is not secreted into the medium, which is typically the case with proteases, the protein can be isolated from the host cell by standard disruption procedures, including freeze thaw, sonication, mechanical disruption, use of lysing agents and the like.

The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a protease protein or peptide that can be further purified to produce desired amounts of protease protein or fragments. Thus, host cells containing expression vectors are useful for peptide production.

Host cells are also useful for conducting cell-based assays involving the protease protein or protease protein fragments, such as those described above as well as other formats known in the art. Thus, a recombinant host cell expressing a native protease protein is useful for assaying compounds that stimulate or inhibit protease protein function.

Host cells are also useful for identifying protease protein mutants in which these functions are affected. If the mutants naturally occur and give rise to a pathology, host cells containing the mutations are useful to assay compounds that have a desired effect on the mutant protease protein (for example, stimulating or inhibiting function) which may not be indicated by their effect on the native protease protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA which is integrated into the genome of a cell from which a transgenic animal develops and which remains in the genome of the mature animal in one or more cell types or tissues of the transgenic animal. These animals are useful for studying the function of a protease protein and identifying and evaluating modulators of protease protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the protease protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the protease protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter Go phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect substrate binding, protease protein activity/activation, and signal transduction, may not be evident from in vitro cell-free or cell-based assays. Accordingly, it is useful to provide non-human transgenic animals to assay in vivo protease protein function, including substrate interaction, the effect of specific mutant protease proteins on protease protein function and substrate interaction, and the effect of chimeric protease proteins. It is also possible to assess the effect of null mutations, that is mutations that substantially or completely eliminate one or more protease protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated polypeptide consisting of the amino acid sequence of SEQ ID NO: 2.
2. An isolated polypeptide having an amino acid sequence comprising SEQ ID NO: 2.
3. A composition comprising the polypeptide of claim 1 and a carrier.
4. A composition comprising the polypeptide of claim 2 and a carrier.
5. An isolated polypeptide having an amino acid sequence comprising SEQ ID NO: 2 and a heterologous sequence.

* * * * *

SEQUENCE LISTING

<160> NUMBER OF SEQ ID NOS: 4

<210> SEQ ID NO 1
<211> LENGTH: 1625
<212> TYPE: DNA
<213> ORGANISM: Homo sapiens

<400> SEQUENCE: 1

```
gaaaattgct gttgggatga agctttgcag ccttgcagtc cttgtaccca ttgttctctt      60
ctgtgagcag catgtcttcg cgtttcagag tggccaagtt ctagctgctc ttcctagaac     120
ctctaggcaa gttcaagttc tacagaatct tactacaaca tatgagattg ttctctggca     180
gccggtaaca gctgacctta ttgtgaagaa aaaacaagtc catttttttg taaatgcatc     240
tgatgtcgac aatgtgaaag cccatttaaa tgtgagcgga attccatgca gtgtcttgct     300
```

-continued

```
ggcagatgtg gaagatctta ttcaacagca gatttccaac gacacagtca gcccccgagc      360
ctccgcatcg tactatgaac agtatcactc actaaatgaa atctattctt ggatagaatt      420
tataactgag aggcatcctg atatgcttac aaaaatccac attggatcct catttgagaa      480
gtacccactc tatgttttaa aggtttctgg aaaagaacaa gcagccaaaa atgccatatg      540
gattgactgt ggaatccatg ccagagaatg gatctctcct gctttctgct tgtggttcat      600
aggccataat cgaatgtgga gaaagaaccg ttctttctat gcaacaatc attgcatcgg       660 aacagacctg aataggaact tgcttccaa acactggtgt gaggaaggtg catccagttc       720
ctcatgctcg gaaacctact gtggacttta tcctgagtca gaaccagaag tgaaggcagt     780
ggctagtttc ttgagaagaa atatcaacca gattaaagca tacatcagca tgcattcata     840
ctcccagcat atagtgtttc catattccta tacacgaagt aaaagcaaag accatgagga     900
actgtctcta gtagccagtg aagcagttcg tgctattgag aaaattagta aaaataccag     960
gtatacacat ggccatggct cagaaaacctt atacctagct cctggaggtg gggacgattg   1020
gatctatgat ttgggcatca atattcgtt tacaattgaa cttcgagata cgggcacata     1080
cggattcttg ctgccggagc gttacatcaa acccacctgt agagaagctt ttgccgctgt    1140
ctctaaaata gcttggcatg tcattaggaa tgtttaatgc ccctgatttt atcattctgc    1200
ttccgtattt taatttactg attccagcaa gaccaaatca ttgtatcaga ttatttttaa    1260
gttttatccg tagttttgat aaaagatttt cctattcctt ggttctgtca gagaacctaa   1320
taagtgctac tttgccatta aggcagacta gggttcatgt cttttttaccc tttaaaaaaa   1380 attgtaaaag tctagttacc tacttttttct ttgattttcg acgtttgact agccatctca    1440
agcaagtttc gacgtttgac tagccatctc aagcaagttt aatcaatgat catctcacgc   1500
tgatcattgg atcctactca acaaaaggaa gggtggtcag aagtacatta aagatttctg   1560
ctccaaattt tcaataaatt tctgcttgtg cctttaaaaa aaaaaataaa aaaaaaaaa    1620 tacat                                                                1625
```

<210> SEQ ID NO 2
<211> LENGTH: 386
<212> TYPE: PRT
<213> ORGANISM: Homo sapiens

<400> SEQUENCE: 2

```
Met Lys Leu Cys Ser Leu Ala Val Leu Val Pro Ile Val Leu Phe Cys
 1               5                  10                  15

Glu Gln His Val Phe Ala Phe Gln Ser Gly Gln Val Leu Ala Ala Leu
             20                  25                  30

Pro Arg Thr Ser Arg Gln Val Gln Val Leu Gln Asn Leu Thr Thr Thr
         35                  40                  45

Tyr Glu Ile Val Leu Trp Gln Pro Val Thr Ala Asp Leu Ile Val Lys
     50                  55                  60

Lys Lys Gln Val His Phe Phe Val Asn Ala Ser Asp Val Asp Asn Val
 65                  70                  75                  80

Lys Ala His Leu Asn Val Ser Gly Ile Pro Cys Ser Val Leu Leu Ala
                 85                  90                  95

Asp Val Glu Asp Leu Ile Gln Gln Ile Ser Asn Asp Thr Val Ser
            100                 105                 110

Pro Arg Ala Ser Ala Ser Tyr Tyr Glu Gln Tyr His Ser Leu Asn Glu
        115                 120                 125

Ile Tyr Ser Trp Ile Glu Phe Ile Thr Glu Arg His Pro Asp Met Leu
```

-continued

```
            130                 135                 140
Thr Lys Ile His Ile Gly Ser Ser Phe Glu Lys Tyr Pro Leu Tyr Val
145                 150                 155                 160

Leu Lys Val Ser Gly Lys Glu Gln Ala Ala Lys Asn Ala Ile Trp Ile
                165                 170                 175

Asp Cys Gly Ile His Ala Arg Glu Trp Ile Ser Pro Ala Phe Cys Leu
            180                 185                 190

Trp Phe Ile Gly His Asn Arg Met Trp Arg Lys Asn Arg Ser Phe Tyr
        195                 200                 205

Ala Asn Asn His Cys Ile Gly Thr Asp Leu Asn Arg Asn Phe Ala Ser
210                 215                 220

Lys His Trp Cys Glu Glu Gly Ala Ser Ser Ser Cys Ser Glu Thr
225                 230                 235                 240

Tyr Cys Gly Leu Tyr Pro Glu Ser Glu Pro Glu Val Lys Ala Val Ala
                245                 250                 255

Ser Phe Leu Arg Arg Asn Ile Asn Gln Ile Lys Ala Tyr Ile Ser Met
                260                 265                 270

His Ser Tyr Ser Gln His Ile Val Phe Pro Tyr Ser Tyr Thr Arg Ser
        275                 280                 285

Lys Ser Lys Asp His Glu Glu Leu Ser Leu Val Ala Ser Glu Ala Val
        290                 295                 300

Arg Ala Ile Glu Lys Ile Ser Lys Asn Thr Arg Tyr Thr His Gly His
305                 310                 315                 320

Gly Ser Glu Thr Leu Tyr Leu Ala Pro Gly Gly Asp Trp Ile
                325                 330                 335

Tyr Asp Leu Gly Ile Lys Tyr Ser Phe Thr Ile Glu Leu Arg Asp Thr
            340                 345                 350

Gly Thr Tyr Gly Phe Leu Leu Pro Glu Arg Tyr Ile Lys Pro Thr Cys
            355                 360                 365

Arg Glu Ala Phe Ala Ala Val Ser Lys Ile Ala Trp His Val Ile Arg
370                 375                 380

Asn Val
385
```

<210> SEQ ID NO 3
<211> LENGTH: 55827
<212> TYPE: DNA
<213> ORGANISM: Homo sapiens

<400> SEQUENCE: 3

```
tcgaatatta cattcagcta aactagtact tgaaagtgaa ggcaaaagaa agttattgtt      60
aaagatacag agcataaaag attttatcac ctgtagactt ttgctatagg aacttttaaa    120
agattgcttc agcaataaga aatgtaattt aaaatttatt gttttttatg cactctgttt    180
cttttgtatc ctgtttctgt ttccccagag aggaaacagg acataaaata aagaagaaac    240
acagatacaa aataagtagc acaaaaattg atagaattta ttagcatatt ttaactattt    300
tgactgttta ttttaaagtt aacttttatg ttaaaaagat aaggtaaaag ttacttgggt    360
tagttttttct ttctctccctt cagtgtgatt atgttattca tttgaaacac aggttcgttt    420
ttgtttgtat tattttttaa aatttatttg tttgcttgtt ttaagtacat atgtgaaaag    480
aacatggttc taaaattcag agtagttcta aagttcagaa ctattcaaaa cacttcaccc    540
aaagaagcgt ccctccctgt ctcttctacc ctgtctttc cagtgtgttt ccactcacct    600
cccgtggata accagtctca ttgatttcta atctatcctt cttatgtttc tttctccaca    660
```

-continued

```
tatgagcaga cacacacata ttttcttatt tcttcttctt tcttatacaa caagtggtta      720
cagtggaggt cactttaatt cattaaatat cattcaatag ttttaaatct caaaaggaaa      780
agtttgaaat ctcaatcatt ttcttctggc caggcacgat ggctcacgcc tgtattccca      840
gcactttgga aggcagaggc aggtggatct cctgagctca ggagtttgag accatccagg      900
gcaacatggt gcaaccctgt ctctactaaa aatacaaaaa aaattaaccg ggtgtggtgg      960
ggcacacctc tagtcccagc tacttgggag gctgaggcag gagaattgct tgagcccag     1020 aggtgaaggt tgcagtgagc caagatcacg cctctgcact ccagcttggg ctacagagtg     1080
agactctgtc tcaaaaaaaa aaaaaaaga aagaaaaaa gaaaaaaat cattttcttc       1140 tcagaagtta attgtgggca ggctgattta ttttgcaaat ttgccaattc tgacttcaag     1200
aacattcaag tgcattaacc aatgggaatg tagggaaga gggctccact cacttacaga      1260
gggtaggata tggcctcata ctagacaaaa tgttatttga tgctactttc aagatgatag     1320
gggatgggcc tggatttaat tgatggctat tatggtgacc tttaaataaa tgagattcaa     1380
agtaacctga tgtctttact gcttgaacca gcttccatga aatagtattc ctattggggg     1440
tgggcctatc attccatatg gtcaaggaaa catcttttg aacagagatc ctgtaatcat     1500
ccttacaaac tgcacttcaa cattggattg gattagccag atttgaggaa ctcacttttt     1560
acgtcttcat aaatttaaaa tgttgaaaaa gtcagaggca agggaagaca tttatagtac     1620
ttcacggtag atctccctca acatgggcta tatatccatt agtcaatatt ctatagctat     1680
tgttctgcaa taaaccagac aagatcctac tgtattacta ccctttattt cttggcccta     1740
ccttccccaa ggagttacac attttctaga tagtctaaat taagagcaac tctcatcata     1800 ctcttttttga gtgtttaatt atcaagcaac agcctaacta agccaataat atttctcttt     1860
ttgggagtgg aaatggaagc taagttgatt gacccacagg aacaagaggg aacatgccgt     1920
tatattttaa ccagtgtgta aagaaggctg ttatgcaatc aatgatctgg ttttttctct     1980
tcagagaaat ttgttgtaca gaaaattgct gttgggatga agctttgcag ccttgcagtc     2040
cttgtaccca ttgttctctt ctgtgagcag catgtcttcg cgtttcagag gtaacccaat     2100
agaatcttag actgtggtgg gccactctcc tcacttgttt gcctcatgtc gtgtcaagtc     2160
agtgcactga gctggtggac aaaatggtaa actttgaagg ccaggtcttt cagaactttc     2220
caagttgccc tgacaaataa gtagacttta gcacaatggg ctatcactaa agacagggtc     2280
ttttttcttt cctggctctg gttttattat tgggagaacc ttggatgata cgcatatcca     2340
gtgactatgg agattcaaga aattaaatct tttataaacg taactatta tactctaact      2400 tgatgtgatga ttcatattct tcctgtcttc acataaaaaa agttaactat ggatcattta     2460
ttttcccctt gtacatggaa cataggagga agaagagggt gaagtgttaa ataggaggtt     2520
tggatcatgc atgattattt agcatggaat atgaaaggaa gaagagttgt gtgataaaga     2580
actattatct gattcttatt ttgcttagta gattcccta ggataaacta tctagaagaa      2640
cacaaatgaa ttcatgctat agcacatgca atgcatggag aaaatagttc cagggtatat     2700
gtaatgtaat ttattaagta gtcaattttt aggctttaaa acattgatat tgtttccttt     2760
ggaattatct tattttttcc ccttttgtttt ggttctatga tcgctttctc ctccaattat    2820
ctttgagaca gatccctctc ctcatgttag taaatgacaa agaaagaaga gacataaggc     2880
aaaggaatat accagtgaca aggaacattc taccaccaaa aaaatgttca cggtcataaa     2940
taaccatagg acaatggttt ggaaaataga tcttgacttg tgagcctgaa gctgtgtttg     3000
```

-continued

```
tacatgatca ctgaactgat tatagttgat tgatcttctt ttgttcaaca tgattgtcga    3060
atgtcgagca acaaattcta tcataaaatg atattatttt tgttatttaa ttgacgtggg    3120
ggtcaagatt gctgcaatga tcagtgactt atgtctttct ctgtatttta tcggtgaatc    3180
atatggtcag gatttctaag gttcttgcta gttctaatat tccataactt gataattggc    3240
ttcagttaag ggaaaggggg agaagagaaa aattggtatc aacatgtcca acttggctac    3300
tgtacacagt ggcagtacca ttgacagtta ggggaaaggg aggaaacctc tgcttattta    3360
gtgcctgtgt ttgtgccagg cactgaacta gtcacttaga aatgttatct ctttaaatgc    3420
ataaaatcct acatgctagg aatctttact gacattttac aaaggaggaa actgagcctc    3480
aggaagaata ataattggc ccaagatcaa acagtaaatg tagagcttgg attcaaaccc     3540
actttagcct catttcaact ccatgcactg acagcattg cctccataaa atctggaaat     3600
taggaagaga gccagtttga aggaaggtca gatttagtca aagggagttg caggcagcag    3660
ttggtttgga aagtagcttg gaagagaggt tcgggattag aggttcagtc tcatggttct    3720
cacccactag cagatctaat catggccttg gcgtcagccc agtgcaatta tcctcagctg    3780
gttgttgcag aggttggcgg gcaggtgggc tcactgcaga ccgccatctt gatcgtagag    3840
taacccaaac tcttggatag gataatcaat agcaaaacac actaaaagct ttagcacatc    3900
tcttcaaatg agtacgtgta tagcagctta gtgacactaa atataacgca aatagaagaa    3960
gtagccaaca ataaaatagt aaaaaaatga gtgagaacat atcttcatgc atgggctttg    4020
ttactatttg ttgcttcagc ttatactctg aaatctgact gatacttatg cttgaaaaaa    4080
ggaatgagaa tgtgactata ttttaaccaa agaatatcac attaaaaata tttaatactt    4140
ttgcatactg cgagggtccc tttgcagagg agaggaggta ggaggacctc agtattgtag    4200
acagatgaat atctgaatcc tggttcccat cccttcactg gaaataacat tgcaaactac    4260
tctttctgtg agtaaaaata aattttttta ccaaatgttt ctgtgctcca cttttccagg    4320
aatggcctat tcctgaagct aaaaaggaaa tctaatttca ttcagggcaa cagactttga    4380
taaattgttg ctggggttca gaatatcaac ccttctaaaa aaaaaaaaaa aaaactaaca    4440
gtctggcttt ttcttaaagc tgttctttgt tttttttttt ttttttttgt cataatcatt    4500
ttcctactaa cagttttttat tcatgcagtc tcttagtggc tgatttgtag gttcattttg    4560
ataaatttca tcagtgaaat gccctggaac aacaacaagt tttaaaggca taaatatcat    4620
atgccaaagg gaaaggcagc caaaaaatca tgactccata ttcatttgct tttaaaagcc    4680
aaacactata aagggtaaaa ataaaatact agcaagaatc ttgtaaacag aatcagtaat    4740
tgtattgtgc agtgattacc taaatgcagc ctgccagccc agactatttg gaaagaggaa    4800
gtaagagaca ctaggaagaa gacttaggaa ttagagagtg gaggagggtt gaggataaag    4860
ggcttctgaa ttattaatag accacaggaa gtgttcctct gttgacttca catactgttt    4920
gggtacctgg agaccagttt actctctttc actttgttcc tactgatgta ttgttttcat    4980
ctcaaagaac aggccaccag tggccttaaa acactgtaat gtgtgcaaca aaattgcagc    5040
cttgggctat gttccattgt tcagagacat cttgccagct ttttaaattc aaaataatct    5100
ttcagaatgg tgaaagtgtg aaccctcccc tgtaaccat agcagggat acaccccaat     5160 gaacataatg acattctcag aagggaagga acagaggaag tgttgcatag gtattaaaag    5220
ctcaggatct ggattcgagc cccagatctg ctacttatca cccatgcaga cttgggcaat    5280
ttgctcgtcc ccttctcagcc tttacttttt ttgtaaagtg acctgttact tcactgtgct    5340
tgtacttctc attcgatttt tggtgcaagg ctgttctttt ttctcaagtg gttattgtgt    5400
```

-continued

```
aagtgctata atcgtatcat tcagagacgc agttgaaaca cagctttagt ttttgtctcc   5460
cattgcccca tgacattttg cgtagtgggg ttatctatca ctgctctcgc atggaaagtt   5520
agaaaatttc aaggcttttt agcctgcttt taagtgacag tccttgggtc ctgctaaaaa   5580
tacaaatagc ctcaatttag aaattagaat gtcacctcca accaaggtat tgttcaaata   5640
tccccatctt tgttgttaaa agaaaatctt taaaagaatt atatttagca aaatttaatt   5700
gaacaaagaa caattttcta atcaagtaac cctcaaaaac gaaagaagtt cagagagttc   5760
tgctcagcaa agtgggcagg cagcacttat aaacagcaaa tggaaatgag gtccagaagc   5820
agcttgagta gttacaggtg agcagttgtc ttactgggca taggctgatc agttggccac   5880
atgggattgg ctgtagcttg gctgctgtga ttggctgaga ctcacctcgt tagtacaaaa   5940
aaaaaatact cctaagttag gttgcagttt gttatgtagc gactcaagtt acgaggcatc   6000
ctcagaccaa atttagttta atttaacatt atttatagga aaacaactgc ctcacctctt   6060
ccacaaacac accttactct ttttcttgtt agtcttttc tcgagttcta acttcttaga    6120
gttgtgtgag acatctttat tggggaagcc tctggaccag acagatgct  tctttgtcta   6180 ggttttcact tgcgactcca tccttccccg ctaagagtct tgcttctacc tctgggctct   6240
tgttgttgag aactttccat ccctttaggt ggccctattg gatggcatct aacattaagt   6300
gtttcttttc attttaacta ctactatcta gccaactaga gaccagccac atgcaggttt   6360
agctttatca ggagaagcca ggcaccagtc tttgtgtctg taaatttgag gaaacatcca   6420
actctctcat tatctcctgg aagtccccct actaggctga ggtaagggga gtgcaccccg   6480
aaacttcatc cctttgggag ggtggtgact tacagaacca taaaaacatg ctaaaaaaaa   6540
aattcacaaa tcctctccct ctttccactc tgacagcttt ttatatagcc tgtttatgac   6600
taagtaaggg gaagcagtca tgaaaccagt ttccaaaaat agagtgatct gactgaccct   6660
catcccatta cctaactctg ttgtgttagc actttgctca aattctgcat aagaagagtc   6720
tgttcactac aagctgaact tggacatatc aataaatttt tggtgaattt ttaacttcat   6780
aattttactc actatttcct aacttatttt ttgaatttcc tttatttttt cttcttaaga   6840
ggtctcattt ggataacata cattttttacc tttatatttt cttctttct ctgcttgttg    6900 actaattttt atacttttct ccttctttaa tacattaggt tttttttta tttaatactg    6960 cccactcaac atttttttgtt cattattttc tttctttctt ttgagaccta gtcatgctct   7020
cttacccagg ctgagtcca gtggtgtgat tttggctcac tgtaacctcc acctcgtggg    7080
ttcaagtgat tctcgtgctt cagccttctg agtagctggg actacaggtg tgagctacta   7140
tgccacgctt atttttgtat ttttagtaaa gacagggttt caccatgttg gtcaggctgg   7200
tcttgaactc ctgacctcag gtgatccacc cacctcggcc tcccaaagtg ctgggattac   7260
aggcgtgagc cactgtgcct ggcccattat tttcaatata atagattatc taccatactg   7320
ccttgtgagg attaaataag aatacctgta aagcacttag cacaatatcc aagttactaa   7380
atatcagtaa aaaagaagaa aagtccccc agacatatta tgctctagtc aacacaagac    7440
ttcctctaca tggacttgaa attcagcatc tctttagata atgaagagct cattgcttga   7500
taaggtgtcc tatctcatgg ttagctcaaa ttgttagaag ttcacactga aattacagtg   7560
atttaatgat atgaacctcc acttctctat actttacatg aaaaggaagc tttgagtttg   7620
ccacatcttt tgctcaaact cccaaaatca tgcccaacca acttttaagt aagggccaca   7680
atcttgaccc cagcatttaa gacccttaac aatcaggtcc taccctgcca ttcgtcctgg   7740
```

```
ctttatttcc tggtatatct ctatataggc cccatatttc tgcccagctg gatcacttct    7800
ccttccttga gctctgattt tacttttcta cttgtgcacc tgcatttatg atgtttcatc    7860
tccaattcgt ttagcaaaat tctgcctatg ttagtcttat accatctcat cttcccttca    7920
cctattgaat cctagtatct cagaagtcca actcagaata tctccattct ctgactacgt    7980
aagtcaaaaa tgatacctga ctttgtattc ctgtagcaga atatttatac cactcgcatt    8040
gtacttttag tgttttatct cacagaatag gcatttgtat cagttgcagg ttagtttccc    8100
caggaaacag actcctgaga tgaagattgc atggaggaag tttactggaa aggaatctca    8160
ggatcagcat ctgtggagga atgaaggaag aaggcttggg cagaggagaa actgacctgt    8220
gatgtaatca aactatggc ctcacctgtt cctgtggaga gccttgaggc tgggttggcc    8280
tggtaaagtt gtcccaaact ggggcaagca ggcatgcctt tgtaacccct gtttattagt    8340
cactgggtgt ggattgtacc ttggaggagg catcatgttg ggcagcacag ctctcttcag    8400
gcaagggcaa gtcctagaaa gggactcagg tgagaatatc agctgccaac cctcccagaa    8460
gctgaggaga caaagaagct gaggaaataa gagttcatcc ctggatggag atctaggcag    8520
caaaacgtga catctactac agtccaaccc tttgtgtcac tcaggtcaat tttcttcata    8580
aaataagctt tgagatcaac tcttctgggg ttttgcttgg tccctcttcc taaaggaaat    8640
atacaagagg aacgttagtg aaataaacta caaccttcac agctacagct agtctcgagg    8700
ccataaccaa tacttgtcat tcctcttctc ccctacccgt tctgttttcc ccaaagaggt    8760
gccctttgct agcacctctt ctaatctagg tggtttacct ggtgagacaa cccagaccct    8820
caatcctcaa ggatctgagt cataatcact gggccctctt gggccatggc tgctgcaatt    8880
gtctgtatac atcaaatttg gacaagggaa tattacagaa cgcctaagct ggattccaaa    8940
catattcttc cctgccacat tcagtatgta agtgcagccc tcaatgtcct tctgattatt    9000
ggagtcaatt acccttcctg catggctaga aaacccatgg taactcctcg ccttcctgat    9060
aatcaatcag catgaggaaa ctgaaatgac tggacagtaa caacagcttt cagtttaaag    9120
gaactcttcc tatgctctct ggaaaccgga attttttataa gtacagagtc catatttgta    9180
gatttaaagt actaattctc cgagtgggtt acttggagtg acggtatatg gaaacactcc    9240
aacttggttc ctggaaccat gtatactacc tagtagggac acagcaccac atgagtattg    9300
atttaaagtg tgcactggag gatgttgcct tccaagttag cacctcaatt gatccttcaa    9360
caaaccattt ttatttcagt aacaggatag cagcaactag gtattctggt atgtgagagg    9420
ctaagtggat tccatggtaa tggacccatt tctgcaattc ccttgttgta aagtggagcc    9480
catgatctga taggatgtta tgtgagatgt tttatcagtg gtcaaacact ccgtaagccc    9540
ttgtatggtg atgcttgcct gaggccctac aggcaggcga gataaaccca tacccagagt    9600
ggaagaggac agatgtagtc aacttaccac ccagtgacta gctggtctct atgaggaatg    9660
gtgctgattc cggggctcaa ctttggtctc cgttgctggc aagttagaca tggggcagca    9720
acagtagcta gatcagcctt aatgagagga gtccgtgctg ctggagccat gcacacttca    9780
tctctgccat caggctattc tgttctagtg ccttttgtgc cagcattggg gtggctgttg    9840
acacaggctg actgacatca actggctgag tcatttgttt atgcagctgt ttaatgtcta    9900
ttctgttgtg ggtgctcctg gttaggcatt aataaatgat acaaagatct tcacacttc    9960 tgcccactct catagttcca ttcacatccc cctttctcca atctctttgt ctccaatctg   10020
tcaagatttc ttcttccagg ttcttgaggg ttttccagt catgtcactt gccactctcc   10080
atgaattcct gcatattcta acactggaaa cacctttcc acccaaggtg tatgatgaga   10140
```

-continued

```
tgcaacactg aagctctgcc tatttgggac gatttccctc tctgctctct ttcggtcacc    10200
cgagtgagtc cataatgcag caccacttca ctttttttt  tcttttttga gatggagtct    10260
ccctctgtcg cccaggctag agtgcagtgg tgcgatatta gctcactaca acctctgcct    10320
cctgggttca agcaattctc ctgcctcagc ctcccaagta gctggcatta caggtgcccg    10380
ccaccatgcc cagctaattt tttgtatttt tagtagagat gggatttcac catattggcc    10440
aggctcgtct cgaactcctg acctcaggtg atccacccac ctcggcctcc caaagtgctg    10500
ggattacaag cgtgagccac cgtgcccagc ccacttcatt ttttacttgt acccatgcac    10560
tatcaacttg actgtccatg tatcagactt cctcttccta cttgtgtcag ttatgatcct    10620
ctgagaagca gacaccaaga tgggattagc tgtgcaagag gtgtgttgag gaaaatgctt    10680
gggtgcaaga aatggggaga gggctggagg aggctgggag agccatgaga ctgcaatgca    10740
agcttaaccc ctgtggagga gagaggaaag gaaggaagca ggtagggaac atttcaggtc    10800
gtagtgcagt tctaagaaag ttttggcaaa accaaccaag agtcctggcc aggcacggtg    10860
gctcacacct gtaatcccag cactttgaga ggccgaggtg tgtggattac ctgaggtcag    10920
gagttcgaga ccagccttac caatatggtg aatccccgtt tttactaaaa atacaaaaat    10980
tagccaggtg tggtggtgcg tgcctgtaat cccagttact cgagaggctg aggcaggaga    11040
atcacttgaa cccacgaggc agaattgtag tgagccaaga ttgctccatt gcactccagc    11100
ctgggtgaca agagcaaaac tctgtctcaa aaaaaaaaa  aaaaaaaaaa agtcctatag    11160
gcagagtcac acatcagaag agtttccagt tttgtagaaa gagcctccct tagtatcccc    11220
accatactca gttattagct gcaagaagcc agtgggaaat gtggtattag cactaacaca    11280
gggacagatt tcagagcaca gtagctgggg gcttatatca agtacacatc ttgcagctgg    11340
agagtgagaa agttaattaa agctgaggca agactgtaaa tatgcactgg tgtctgtccc    11400
aagtggatgt taactgttct gatgcttttt ccgactgaca tatccagcgc aatagctgaa    11460
taccatatgc ctgagactct accccggcaa agatgccaca tcaagcacta ggctgcaat    11520 tgagattgtt gcttggttga gtttgattgt ttgctgtcgt tttccaggat ccatctggtt    11580
tttgtgggat ccagatggca aattaaatgt ggttttgatg ggatctatca tccctgcatc    11640
ttttaggtct ttaagggtgg tactgatatt tgtcatttcc cctcaaggat gaatttttt     11700 tttttaattt tgatatcttg gctgggaggt tgggcaattt cagaggtttc cttttggctt    11760
ttcccactat gatagctctg gtcttacagt caaggaaaca atgtggaggt tctgccaact    11820
acctagtatg ttcatgtcaa ttatacattt ggtgaccagg gaaataatga tgggggaatc    11880
cattaacatg gtgcacccgc tatgagctag tcttaggcta gggctccaga tacccaagtt    11940
tcaaaatcaa cttggatagt gaccctgcat ccaacacacc tgaaaatatt tgagtattac    12000
cctttcccca gggtgcagac ttacctgagg aaatttccat aggtctcttt gggaaaggac    12060
tgaaggagtc atgatctttt tagattcttt ttttatacag ttgcagggtc tttccttgtg    12120
gggacctgac tcctccttca ggcaagaaat tctgggtcta agaacagctc agatctggaa    12180
aagggcaatg gattatgact tttgattagg atagctgtcc tcagcctctc tcattatcca    12240
gctttgattt attttttattg taaagattga gcaatccttt tgttggctgc ttctctatct    12300
tgcccctaag aactctgtgt tctcctaacc gactccacaa ttttctaagg gtcatggtcc    12360
tctggctgcc actccgacct tactgctcat tgtaataact gtgcccaact tgttactggt    12420
ggttaagccc tcccgcctgg cttctctata cagggatctt aacatctcca ttggtatcag    12480
```

```
agagctcagt tctgtaatgg catgtcctgt agttagccct caggatctat tcccacctcc    12540
cctcctggcc ttcaagccaa taacctaggg tagtcacaac ataagctggc tgtggaagtg    12600
ctgggcatgt taacaaagga aagggactat accccaaagg aggtgcactc acccatgcta    12660
cagaatttaa cattctagtt agttccttga gaggtggtac aaacatgctg ttagggtagt    12720
ttttggaagc ttggagaaag catggcctgc accatctgag ctagaaatgt cagagcgaat    12780
gtggcagatg gtgaaaaaag agatagagca cactagaata aaaatgctat gtaaggctag    12840
aaaacccact gggtgactat gctactccaa gggcccagag aacattctgt ttatgaaaat    12900
aataaggaat gtgctggtga gatgagaggg ttaccagcat cactgagaag cttgttagtg    12960 gcttttcac agtcaaagga gatttttctt taaatttaat tttcttgaat aaatacaaga    13020
ataggagttc ttttgggttt aaaaagtaaa caatacagaa aagcataaaa ttagggagaa    13080
aatactaaaa tttcaccatc ctggtgaaaa tatgaacatg tttgtgatca tcctttcata    13140
catttctcca catagttata cctccctggg tataattgta tactagttca atgttgtatc    13200
tcctattggt actatagaaa cctttctttt aaaagaatc tcatttgttc ttcccctgcc     13260
acttacccaa ggcttcaatt gccatttccc accctccaaa tcaaagctaa caatgtgttg    13320
tttatttatg tataattttc tcctgatttt aacacatata attttctttt atctttctaa    13380
ctttttccca aaaataggat catatttcat aaagttctcc atatcttgct tttctccctt    13440
aatatgccat ttaaagcccc caagttaact gttataaatc aaactcattt tttataatga    13500
ctgaaaagca ttctagaatg tggagacact accaacattc gacaattctg ttactgctga    13560
gcattcacat ggttttagg ttttgttact atgaataatg ccgtaataca catccttgaa     13620
catgtatctt taatcagtgg tttaatagtt tatgctaaac ttgtaccaga gattgacata    13680
aaatttctca gtctagctac ttttcccctc ttctaataag caagtctctc catagactta    13740
tttccagaat tcagaatatt ttactcagga tttccaaaat aaagccaccc tccacccttg    13800
ttaaagttat ccttggtggg cgcggtggct cacgcctgta atcccagcat tttgggaggc    13860
tgaggcgggt ggattgtctg aggtcaggag ttcaagacca gcctgaccaa catggtgaaa    13920
ccccatctct actaaaaata caaaaattag ccgggcatgg tggtgcacgc ctgtaatccc    13980
agctactcag gaggctaagg caggagaatc gcttgaaccc agaaggtgga ggttgcagtg    14040
agccaagatc acgccattgc actccagcct gggtgacaga gcgagactcc atctcaaaaa    14100
caaacaaaca aacaaaaaca aacaaaggaa acaaataaaa attatcccta taaatcacag    14160
ctcaaatgtt accttctaa cttctaattg cctacaagat aaagtccaaa tttctcagca     14220
tgcattcaag accttctcta gggaaggatg aacataactt cccacactca tttctgttta    14280
gctcccattc ttctcttgct ttaaacaccc gtatcctata cttggcaaca atgaacaaga    14340 gccattttc caaaaatgcc ctttatctct tgctattgtg cctttaccca ctcttagaca     14400
ttcttacaca cccagacatc ccttctatga agcctttgct aataatgaca aacagaagtt    14460
atcataacct cttttgtgct ttgagagctc ttggtacatg gttttcttaa ataagatgat    14520
ttatttggaa tatttttaga tttacagaaa agttgccaat tgtaatacaa ctgtataccc    14580
ctcacccaat ataccctaat gttaacattt tatattatca tgatgtatta gtaaaaactg    14640
agaaatcaac attgttatat tactattaac taaactccag actttttgg atttcaccag     14700 ttttcccact aaagctcttt ttctgttccg agatctaatc cagaacacca tgttgcattt    14760
agtcataatg ttgctgttgt ctaatgtctt gagtgctgtt gttccataca ttttgtccag    14820 gttttagtt atttcataaa ggagggtata actggaagca aagtctaaga ttagttttaa     14880
```

```
ataaagcaag aggaagcatt ttttctaatt taaaatatat ctatcgtcat atttcaaggg   14940
caatatttgt ttgaaaataa aagaaaaatc tcgttcagtt aaaaaaaagg ggggctcag    15000 agctggcaaa tgccaccaac atgcttaatt ttaatttaaa taaaatagtt cttgtgaggt   15060
tactcagtgg tatactggaa acctgagaat gccattgccg ttaacagagt ccacaatccc   15120
tcacctcact gcttcctttc tctccttatc acttacctat aaaactggat ggagagctgc   15180
agaaatgagg acatttgcta agaaattctt tcttttctaa gtggtatgtg aaaataaagt   15240
aaattcatgt tgagtcacat taatctattg ccttggctgt gtaagaatca ccaagaattc   15300
tcacaacctt agcaacagtt gcaaaataga aatacaacaa agcaaggtg agaaaaccaa    15360 ccaagtgtct gcttttaaa caatctattg atataattca ccacattaag atattaagcc    15420
agaaaaccca tatgctcatc ttatagaaag catttaaaat ccacacttat tcatcataaa   15480
aactcttaac aaagagcaag gagttttta aaactgataa aagacatcta ccaaaaatct    15540
acaacaagca ttctaatggt aaaatatttt aaggtttttc ttaaaaatca ggaatcatgc   15600
attttatctc cacttctatt caatgttgta ctgaagtccc aggcaacaca gcaagacaaa   15660
aaggaagggg aaaaggggct ctataagcat tgaaattaaa gaagcagaac gtattaaaag   15720
tacattaagt acattaaaag taacggcaaa accgcaatt acttttgcac caacctaata    15780
gtgtgtgcag atgtaatgat tacttgcaaa gagaaatatc cccccaaata tctataccaa   15840
aattatcaaa actaccaaga gagctaaata gaaaatcaac accaaaaatc atttttattt   15900
ctatatctta gcaaaaaga gcttagaggt ggcatgttaa aagttaccat ttactaacga    15960
aaaggcaaat ttgttagaag aaaacataat ttaaaaatgt gcagccgggc acggtggctc   16020
acgcctgtaa tcccagcact ttgggaggct gaggcaggag gatcacgagg tcaggagttc   16080
gagaccagcc tgaccaacat ggtgaaaccc agtctctact aaaaatacaa aaaattagcc   16140
aggtgtgttg gtgtgcacct gtaatcccag ctactcagga ggcttgaggc aggaaaatcg   16200
cttgaaccag ggacgtggag gttgcagtga gccgagatgg cgccactgca ctccagtctg   16260
ggcaaaagag cgagactccg tctcaaaaag aaaaaaaaa aagtgcaaca tctttatgga    16320
taaaattgta aaacttttgg aaaggcatta agaatagat aaatgggctg tgtgcagtgg    16380
ctcacacctg taatcccagc actttgggag gctgaggcgg gtggatcacg gggtcaggag   16440
ttcgagacca gcctgactaa catggtgaaa ccacgtctct actaaaaaat acaaaaatta   16500
gccagccatg tggtgtgca cctgtaatcc cagctactca ggaggccgag tcaggagaat    16560
tgcttgaacc tgggaggcgg aggttgccct gagccaagat cgctccattg cactcctgcc   16620
tgggtgacag agtgagactc catctccaaa aaaaaaaaa aaaagaata gacaaataga    16680 caaattcact gtatttatta ataatgacac tcagaatcgt gagtatatct gttctttcca   16740
aattattaat ctattgatcc aatataattc taatgaaaat ttcattttt tcatgaaaca    16800 taacaagctg atttttaaaa attatgtgaa aaagcaaagg atcaagacaa gaggcttgta   16860 aaaaaaaag aattgggcag ggcagagggg aagcaagagt ttgttctcta agatattagg    16920
atgtaatatg aagctaccat cactaagatg agtagtattg gctcaagggt agacaaatat   16980
atcaatagaa cataatagag aactaagaaa tagagcacat tatattagca agggtaatcc   17040
ttgattatgc tataatcact aataaaacct gaaacagctt tacttaatac aatataggt    17100 taattctgtc ttagtacgtt tgggcagtta taacaaaaaa taccttaagt ggtgtagctt   17160
ataaacaaca gaaattttatt ctcacggttc tggaggctgg gaagttcatg acaaagcacc   17220
```

```
agctaattct tgtgtttggg gagggactat cttccgcata gacagaacct tcccgctata   17280
tattcacatg gtggaagggg gagggatct cttttttaag gtcactaatc ccattcatga    17340
agcctctccc cttatgacct aatcacctcc caaaacctc atctcctaat accttggagg    17400
ttaggatttc aacataggaa ttttgggggg acacaaacat tcagatcaga gcaatttctc   17460
actcataata ctaattgatg aaggtcatag aactctccct ggtgctctcc ttcaacttgg   17520
agatcttggc tgcttccatt atgcaactcc acatttgagg ctctttgctt ctggccgcag   17580
gatgagaggg ggcacgtgca catgaagaca cacctactct taggcaccta taacactccc   17640
acgcattccc attggcaaag ctcaggcact ggctctcaac acaaccacac ggaaggctgg   17700
gtaatgaagt ttttctgtct atgcaggaag aggcagtggt gttgatgaac caacattttc   17760
tctgccaaac agtatggaaa cttgatatat gacaaaattg acatagtgga tccctgggaa   17820
aaatatagat gatgtaaaaa atcataataa taaacgatgc taagaagaaa aaaaagaag    17880
tctatttctt ctttacactg cacccaacca aataattttc aattgaattt aaaatttaaa   17940
taagaaggac agaagaagta tatgagaata tctttatatc ccagatatct agaaagacat   18000
cttaaaccac acaaacctgg aaggaaatga ttaaaaaaaa aaaagcacat catcaagaaa   18060
gagaaaagac aaattacaaa ctgctagaag atatttgcaa tacatataac tgacaagaaa   18120
ttagtattta gaatatataa agaaattata caaattaact actacaaaaa tacaagtaaa   18180
ttagaaaaaa atgggcagtt gatctgaata aacataacat ataagcaaaa atatgaatgg   18240
ccaataatca aatataaaca actgtacttc attaataagt cagaaaatga aaatcaaaat   18300
cacaagaaaa tttcatttca taaaaatttg attgcaaaag ttgaaaagtc agagagcatc   18360
aggtattggc aaggaggaag aacaacagga aatcttttcc actgctactg acaatataaa   18420
ttgatacaaa aaacttgagg actgatatga cactatccta tgaaattaaa actgtgcata   18480
tcccatgaaa tggcaattcc acttgtaaga aaatgctttc atgtgtgaac tgtggctagc   18540
tacttcaaca cagatgataa tcttgagaat acaatactga acaaagaaa  aacaagattc   18600
agaagaatac atatagtata ccatttttat aaagttgaat caggcaaatc taagggtatt   18660
gtttcagaat tcacacatac atgtgtttaa aaatccatgc tataaagaaa aacaagggaa   18720
tgagcaaaag tcaaaattta aggtagagga tacctctggt gatgtggcaa ggggtagga   18780
cagagaggag cacacaagga tcttcaggat gtcaaggaag ctggactttt taagtgggt    18840
gatgggttca caggcattca ttttattgta taattaacta ggatcagcat aaatattccc   18900
ttatgcatca aatatttaat ttttaaaatt aaaacacaca tgcacgcaca agaaaaagga   18960
aagaagtaaa tactctgtaa actgaccccc agtcaagaga gctgttgatt ttgcaattgc   19020
ttaggagcat aaagactgag agtatatgtt ctccttattac actgaatctg tagtaagatc   19080
ctctgtccta ataacatttt aaattttgtt tcccttttgc aattacctaa aagctcctca   19140
cagtataata tattccatct ttactcttta tttaatatca aaatcctctt ttattttttt   19200
ccccagtggc caagttctag ctgctcttcc tagaacctct aggcaagttc aagttctaca   19260
gaatcttact acaacatatg aggtaatttc tccctaattt atgtttatat tggtttcact   19320
ttgtataagc actgggtgtt gagtttcctc ctgtatgttg tctggcttac atgtatctgg   19380
tatgaactct tcttctcata gtcttctctc ccttctcata atcacatgat tttgttggtt   19440
ccccaaatca acacttcttc acttgtgcta ttggctttcc agccaatttc ataatagtac   19500
cttgggatat aaagtgtgca cttacaaaga ggctacagta acagaaatta aaatatttat   19560
aaataaaacc ttactcatga aacaatggtt cttaaccaag gatgcaccag aaagacagag   19620
```

-continued

```
tacatttatt aaaattctca cccaggcacc catctcgaca taatgtctaa gatgtagaaa    19680
attgacaaga attacagaat attaatggca gtggcggccc atctagagcg gctgctgcca    19740
tgcgggaggc acggctgggg ctgtgtgctc cacggagcca gcagaagcca ggaggaggta    19800
aaagtcccgc ccccttctgt gatggcaggg cggcagcctc atgctcccca ggcgcagctg    19860
cagctgcccg ctgcagctac agacctggac atccctgtgc tcttggggc caggagcagg     19920 caggagccct gccctcctgg gcgcagctgc agctgcccag ctggggttgc agacccaggc    19980
atttctgcac tctcagtgtt ctgagaagga ccctcattcc cctacaggct cggaagtgcc    20040
tgctcccact gtctggtctc tccgagttcc tggtgctcac tccaatcttg gagcaaaatt    20100
gaggctgagc ctaggtgttg tcacaacctg gctggctgtg gcatgatca gagcggtact     20160 gacatgctag cccctgctg cctcagcccc ctctggactt tgggtactga cgagcacagg     20220
agggaagcca aggggtggc tgagggcttc tcggcactgg cctgcaggcc ccctcagctg     20280
gaaaatcctg ggtgccataa atagccgtag gaggcagaca ggatcctagg cagaaagggg    20340
cgggtccctg gtgaagcccc accttcaagc ccaggaaggc tgccagtccc gtggaccgca    20400
gtgggaactg acggtgattt ttccgcaccc gcctatggcc acccatgaac caatcagcac    20460
tcacttcctc ccatctgaag cccatagaaa tcccccggat tcagccagac tcttctggag    20520
agacatgggg aggaccagct gtagagagga gccacccact ccagggtctc ctctctgctg    20580
agaactaaca ctcatcagga caccctggct gcagagagga gctacccacc gcgagtctcc    20640
tctgagctgt tctattactc agtaaagctc ctcttcacct tgctcaccct ccgcttgtcc    20700
acgtacgtca ttgttcccgg gcgctgaacc tgccaaatgg tggaggtgaa agagctctaa    20760
cacaaacagg gctgaaacac gccccttgct tgccacgttg tgggtgacaa gaaggagaga    20820
agagctgcag cctttggg agctcagacc taagaactcc ccgaggcagg actatgacac      20880
cctctttagg gctctgtggt tcctgacgtc tccaaacttc tgggtgccac caccttcccc    20940
ggtgccagcc attgaagctg cttgagggac acctggtcca gccacagcct gcagggagc     21000 cgaaagatgc ccaccctgcc gcagccagca tgcctcgctg tgtgtagtag ctggacccca    21060
cacctgctca ctcacacacc cctcaccgct cagctcgccc ttggcacgaa tgagacccaa    21120
gccagtagca cgagatgagt gcagcctgcc aggccgagtg ggctcagcgg gcctgagcaa    21180
agcttaggca aaggcgccac tgaccacaga ggtttctgct ggtgaagcga ccccagggat    21240
cctgtaacaa tatcatggta caaaattgat ggctccttgt ttgttagtgt tttccaagaa    21300
gcagaggtca agactagact ggaggagcaa gcgatgaggg gaatgctgtt ggaggataga    21360
ggcgggagct ggagaaggca gagagcatca tcagaccatg tcatagctct gacacctctg    21420
cagaaagggg aattttgttt ggagaatctc agactatagg gcaggtccaa agaaggctgg    21480
gctaggtcag tctcagtctg gcaagaatgg gcctgcatta acacttccac aggactcggt    21540
tactggctgg atgcagccct gagaccacat ggcctcagct tctagtgggt caccagggca    21600
gccactgaaa acaccagcca actgtatttc tctcaaccga agagctaaat ggtgcatatt    21660
cacgaccacc acatcatggt aaagaggaaa tactacaaga ggaagcatct gagatttaga    21720
attctagttc ttgttctgtc atttctaggt gtatgatttt agatgtcagg tatgaacctt    21780
aatttcttca cctgaacaat gcaaataata acacctgcct agtctatatc aaagcgttat    21840
aaatatcaaa ggaaatgagt gtgaaagtgc tttgaaaaag tacgtgtagt ggctcgtgcc    21900
tgtaatccca gcactttgga gggccgaggt gggcggatca cgaggtcagg agatcgagac    21960
```

```
catcctggct aacacggtga aacccctgtct ctactaaaaa tacaaaaaat tagccgggcg  22020
tggtggcggg cgcctgtagt cccagctacc cgggaggctg aggcaggaga atggcgagaa  22080
ctcgggaggc agagcttgca gtgagccaag atcgcgccac tgcactccag cctgggagac  22140
agccagactc cgtctcaaaa aaaaaataaa aaataaaaaa taaataaata aataaataaa  22200
aagcacatta agagagaaaa aatgtaaatc ttattggaag cctttttaaa aaaggaaca   22260
atgacatgat gataattaca agaacatgaa attttatta ataaaatca atgtttaatc    22320
aactttcttt ctagaaaaaa ttttgttttcc tttcaaatat ctgatgtaca catgcaattt 22380
tacagttaag ccatgaatat agtcattcat tcatcattgt ctcatcaaat atttatggat  22440
tatcttgtat attccaggcc ctttttatttt atttttttt agcaactaga gttatagaaa  22500
ggaattttaa aaaactcact gcaaaataaa tgtttatatt accatgtgtg tggatgggga  22560
ccagcaccag ggagtgtcct tttcatactc cttatagata aaactgtcat ggctctagct  22620
acagatgaga atgatgtgaa caactctttt ttaattttat caattttgcc ccttaaactg  22680
tagattgttc tctggcagcc ggtaacagct gaccttattg tgaagaaaaa acaagtccat  22740
ttttttgtaa atgcatctga tgtcgacaat gtgaaagccc atttaaatgt gagcggaatt  22800
ccatgcaggt aggcaccgtt caatacgtat tgagtagtta ttataaacac ttactatgca  22860
cttgactagg gtatggtata attgcttcct ggaaaaataa aatgtattaa ccatggcagc   22920
atagaagtct ctgactggac caaatggact ggtgataaag cctaaggtcc agctctgtga   22980
tcttggataa atggttcaac ccctcatgac ctccgtccct tatctaaaat gcaggttaga   23040
ctcagtgatt ggtaaaggct ctcatagttc ctttttctct gactctgtac ccagactcag   23100
ggagcaaaac tgtcatttgc cttggtaggc ttttttgatat ctcctgaaaa agcagcttcg   23160
ggagggatt tagcttctgc taattcttct tcacaaagac agtgaccatt tctgaatgtc    23220
tggctttaaa aagtgtaaca ggtggttgga ctctgcagag acctcgggtt agtctggcac   23280
tgccccttac cacctatatg accctggggg aattattcac ctctctgctc ccaagttttg   23340
tatattaagg gtaaaaacag cacctaccct gtggattaga aatgatttcc ttttcttaaa   23400
aagtgtatca ggtacaattt ctgctcacag tctagccttc ttcttatgga gtctcctaat   23460
atctcccctc catatccact gcccaactgc cagtaccttc ctggtggcct ggccccttga   23520
gaccatgctc tcttctgtgt atcaatgggt gcccctgga taatatgcta tgttaattat    23580
tagtaatata ttatagagta tattataggt gtgtactgtt ttccaggaac tgtgctgaac   23640
cttttctatta attgacattg tgtctattaa tctttattta accccgtgaa gtagatgcaa   23700
ccccattata tagatgaaaa aatatcctta cttataaagg aatttttcag ggtaaatcag   23760
aaagaacatg gcagagttag gagtcgaact tagacccttc tgatgtcaac actgcggctt   23820
ttatttattg gcctaaataa aagtaaagaa cccttttatta gtatgatagc taactttcaa   23880
cttgtccatc tcaggcgata gaatgcctga attcagctaa aatatttgcc tggttaacaa   23940
atgtggtgct ctgaagagaa cttgaatgag atgcctttcc tgtacttccc ttttcctgtt   24000
ctatttcttt ggctctgcag aacatctgat gcaggtcaat gggggaaaaa ataagaaaaa   24060
aaaaaaaga aagaaaaggc ttttctgctt cttcttcctc tttaactgaa aacagcataa    24120
tacagtgtta gtctggattg aacaaaggta cattaatcca tatattcata taaaagacac    24180
tgaagaatca ccattgagta atgttggtaa tggtgggaaa cggtggtttt tatggaggtc    24240
ctgaaaaatat acctaatagg agctactttt tctctagtgc ccatgtaggc tctactgaaa    24300
gggtttgtca accagtttac cacaatgcga gatgtcttac ttttaccttg atgaaatgct     24360
```

```
tatgaagttt cttagtgatt ttttttcttc atgctcacct gctgtgcctg caatgggcca    24420
tgtgggaaga tccaccctct gcttggaaac tagctcactc tctgtttcat cacctagtgt    24480
cttgctggca gacgtggaag atcttattca acagcagatt ccaacgaca cagtcagccc     24540
ccgagcctcc gcatcgtact atgaacagta tcactcacta aatgaagtaa gccatcacac    24600
agctcttcaa agctactatt tcatttaac cagtattgcc atttcaatca ggggaatatt     24660
caagaatcat aattggtgga agatggtaaa aaataaaaca caaacacact taggttaatt    24720
aaatggtggt cattcatttt ttggtagatc tcttccctga aagactgca tcatatttgg     24780
taaactgcag gatgtttgtc tacagctaag aatatctcta actgctggga ataacacttt    24840
atgctatgga acaacagaaa ttaaagaatt ggggctttta attaaaactg ccaccaaaaa    24900
attaccagtc caattaatca tgtctctttg gaccattacc ctaattttac taattaccag    24960
attagctcac tgaattaaag gaatatattc acttatattt aatacactat aactaattgc    25020
attttattcc ttagaaggaa gctatttaaa ctaataataa taataatgcc tttgttttaa    25080
tctgtaagaa attggatttt ttttctatca gtacttacag gttccactcc ttctagagag    25140
aacttgagta agatgttgat gtgcaggtga gacctcagca agctttcaca taatccacta    25200
aaagccattc cctgtatttg ttagttgaaa gaataaattc gcaggaggac tttcttttt     25260
atatgatatt ctccaagtag taaaaatacc ttgatgcctt tttatgagta tgcagctata    25320
ttgcctaata taactatttt tgtcatcttt gactaagtgc ccagaaaacta ttagggacca   25380
tatccatatt tttaagacat ctaagactta ggtaatgaga atcaatttta tgtatataat    25440
ctttaaaagc atctgttcct tcccagttaa ttaagccaga gtcagtatgc ttctagaatg    25500
tgtgcctggt tgattgaggg ggccttaaaa ttgcaccccc ccttttttaa tctctcctac    25560
atctatccaa cttagaccac ctctctccag catccatcag cacgactgca tgagcaaact    25620
tgatgcagag aggcttcata ggtgggattt caccttcata gaaggtgaaa ctgtcactgc    25680
tgtgataagt ttggtgggga gagggaatg ccgtaaacag aagtattttt aaatatttgt    25740
taaaacatat tttaattatt ttgttcaaaa aagttatgtt ttcttacgat atgttcagga    25800
aagagttgga atgacacagg aggaaaaaat aagcacatgg ctctattagt tttctagggc    25860
tgtggtaata aaataccaca gactgtgtag ctgaaatcac agaaatttgt tttctcatga    25920
ttctagaggc tagaagatca aggtgtcagt aggtttggtt tctactgagg cctctttcct    25980
cagcttgtag gtagttgcca tctcacagcg ttcttcctca tatgcctttt ctttcctttt    26040
tttttttttt tttttttgaga cagagttct ctctgtcacc caggctggag tgcgatagca    26100
tgattttggc tcactgcaac ctgcgcctct gggttcaag caattctcct gcctcagcct    26160
ccagagtagc tgggactaga ggcgcatacc accacgctca gctaattttt tgtattttta    26220
gtagagatgg gatttcacca tgttggacag gctggtcttg aattcctgag ctcaagtgat    26280
ctgctcgcct tggcctccca aaattctagg attacaggcg tgagccacca tgcccagcct    26340
catatgacct tttgtttgtg cacatgcatc cctggtctct ctctgtatat cttaatctcc    26400
tcttcatata aggacaccag tcagattgga ttcgtgccca ctctaagggc ctcatgttga    26460
cttgatcatc tctttaaagg ccctatctcc aaatacagtc actttctaac ctactgggag    26520
ttagggattg aacatatgaa ttggagaaag gggtacaaca tctactcctt aactatgaca    26580
ttatagaaaa tgtcttgtgc ttctcttgc acccccgccc ctattatttt ctaacaggtt     26640
cataggaacc ataagcattt tgctctcaga atattcctct aagtgcttct ttcccttga     26700
```

-continued

```
tcggtggtct cttgatcagc cctacctaca agatggactg gtgggcagca gaggttattt    26760
tgtcattgac tcacaccagg agatcttaaa tgatccggtg tagggagaaa gaaacaaatg    26820
gccaaaaatt acttcttaga agaaatggtg agagaaaaga gttcttcaaa ggatgttaca    26880
ttattacccc agcttagttt gagaaatgaa taaagtctgt cggttaaact gccttcatat    26940
tatacagcct ctcctgttag aggaaatcta ctgaagtatc aatgcataaa ttattttttt    27000
gtggtagctt tctcagatgt atttatgcct agaagagtaa cacaggaaat ggagattcaa    27060
ttaggaaatt gctgacagtt acatttctga cacccagac actgacaggg tcggtacttg     27120
gtggcaggtg ggcaggagcc cttaattctc agcatgggga caaccactca cacctaccac    27180
tcatgctggt tatgtgatct cagagaaccc aaggataaat ggtgctccag tttttaccag    27240
ctaggattgc tatttgaaat cacctctaga aaagttccca gagataaagc cagggtttga    27300
ttgcttctgt ttcagaaggc atcagagttt aagaatggac cctggaaagt tggtccaaat    27360
taaaacataa cccagttcaa tcccagcaat cccaaaccag acaataattc aatgtttgct    27420
ttgaagtggg tgctagccta aagtcagaat ttttttcttt tcttttcttt tcttttcttt    27480
tttttttttt tttttgcttt ttccttcccc tattatcttg acagaacctc aaatacaact    27540
ggacttccac ccaagagaga ggtccagaat cgaactactt cttgggggga taattgagtt    27600
tgtttgtttt tcctccagat ggtccccacc tttgcctctc atcattgtgc caatctcact    27660
gtgcttgcac aggtctttag tgggaaacaa tgatgcttcc atttatcctg catgaagaca    27720
gtgctaaggg ctcccttcat cttgaaaagt gcattttaa aaaagtctca tataaaagtg     27780
aacttttgaa tgaatgagaa caagaatttc atacacaggg gcagtgactc aatgtgatga    27840
ctttaaaagt aactttcagg ggccatagtt tatagattaa cttttcctac ctcattataa    27900
gtatcttagc acttttttcac tctttctcaa aaccttgaca cttatcaaaa ctttaattttt   27960
attaatttcc ctaaacagca gaagaaacac cctgccctaa gtgctttagg tcctcgtgca    28020
ttccacatac agaggttttc ctttctctga agaagttgtc tgcttgcttt ggtcagggaa    28080
atgctttgaa cttggcttcg tgactaacct ctggtttcca ttttgctaga tctattcttg    28140
gatagaattt ataactgaga ggcatcctga tatgcttaca aaaatccaca ttggatcctc    28200
atttgagaag tacccactct atgttttaaa ggtatgttgt ggggaaagtt gttgatcttt    28260
cactgtgagg ggagggatta attctccagt cgtgtttgtt aaaacttgag tttgtttcct    28320
ttgagttctg aaaatatttg cattacaagt gttcctcaac tttaatacct ggctatttag    28380
gggttggtta ttttttcccat taataatata gtcttgtcct ggtctgtatg tcctaatctc    28440
ctcccacaag gacaccagtc agtctggatt agtacacacc ctaagggcct catgttaact    28500
taatcacctc tttaaaggcc ctatctccaa atacagtctc taggggtta aggcttcaat     28560
tctagatgaa tcccagttct agaattaact ctgtttctgt ttatgtgaca ttagataagc    28620
catttaacat ttccataaaa tgaaggaagt ggtgtttatt tttttcaagt ccttgtttta    28680
ttttcgttag tggacaaaca ctatttctgt taggggacaa acactaacag aaaataaaac    28740
agggacttga aaaaataaaa ttaaaaatta aaaaagtgg tgcagctttt tgatgttaat     28800
ttttaaaaat tgatacataa taattgtaca tgtttctggg gtacatgtga ttttttttct    28860
ccctccctcc tcacatgtga tgttttgata catgcataca atgtgtaaat cagggtattt    28920
gggatatcca tcacttcaaa catttatcat ttctttgtgt tgggaacatt ttaagttcat    28980
cttctagcta ttttgaaata ttgttgattc tcgtcaccct actgtgctac tacacactag    29040
aacttattcc ttctatctat tttgtaccca ctaattaatc tctctttatc ctccttttccc   29100
```

```
agcctctggt aatcaccatt ctactctcta cctctatgag atcaacgttt tccactcccc    29160
atatcagtga gaacatgtag tatttgtctt tccctacata gcttatttca gggcatgttg    29220
ctgcaaatga taggatttta ttccttttaa tgcctgagta atattccatt tgttatccac    29280
attttccaca tgcatatcca cattttcttt atccacatcc acattttctt tatccattca    29340
tctgttgaag aacacttagg ttgattctat atcttgacta ttgtgaatgg tgctgtaata    29400
aacatgggag tgcaggtatc ttttgatat actgatttcc tttcttttgg atacataccc     29460
aataatagga ctgctggctt atatggtagt tccatttta gttttttgag gaacctccac     29520 atggttttc atagtggctg aactaattta cattcctacc aacagtgtac aagggttccc     29580
ctttctccac atcctctcta gcattcgtaa ttgcctgtct tttggataaa agccatttta    29640
actggaatga gatgacattg cattgtggtt ttaattcaca tttccctgat gattagtgat    29700
gttgaggatt ttttcatata cctgttgccc atttgtgtgt cttcttttga gaaatgtctg    29760
ttcagattcc tttctcattt ttaaaattgg attatttgtt ttttccttt tgaattgttt     29820 gcgttcctta tatattctgg ttattaagtc cctgttggct ggatagcttg cacatatttt    29880
ctcccatttt tttcttttca cgctgttatt cctttgctg tgcagaagca aattttcagt     29940
ttgatgtaat ccccctttatc tattttttgct tctgttgact gtgcttttga gatcttaccc   30000
aaaaaatctt tgctgagacc aaagtcctga attgttttcc caatgttttc ttctagtagt    30060
tttatagttt taggtattac atttaattct aatctgtttt tagttgattt tatatataag    30120
gcgagagata ggcatttagt ttgaatttta tgaataaaat ttttcccaat accatttatt    30180
gacaagactg tccttttccc aatgtatgtt cttggtgcct ttgttgaaaa tgagttaact    30240
gtagatctgt ggatttattt ctgggttctc tattctaatc cattggtcca tgtgtctgtt    30300
tttatgccag taccatgctg ttttagtact ccagctttgc tcattctgtt cagcattgct    30360
ttggattttc aagatctctt atggctccat atgaattta gaattttttt tctcttcta      30420 tgaagagtat attgatattg acagggattg cattgaatct gtagattcca ttcggtagta    30480
tggacatttt aacaatatta attcttaagc ccgtgagcat gaggtatctt ttcattttt     30540 tgtgtgttct cttcagtttc tttcatcagt gttctatggt cttaattgta ggtcttcac    30600 ttctttggtt agatttatta caggtttttt tttttggtc attgtaaatg gtatttcttt    30660
cttgattttt cttttaggtt gtctgctatt gttgtatata aatgctactg atttttgtgtg   30720 ctgattttat aacctgcaat ttactgaatt tatcagttct aacacagttt tttggtggag    30780
gctaggtttt tctaaatata agatcgtgtc atctaaaacc aaggataatt tgattttcc     30840 cttccaattt agatgccttt tatttctttc tcttacctgt ttgctctggt tagtacttcc    30900
tggtacagct tttgaaacta agtaagacc aggacaacaa atcccagcga gggacaaaca     30960
gccggacaag gctgaagtcc tttgcagtag ggttcttatg atggtttcta ctccaatttc    31020
cacccatttg gttatttatt ttcagtcgca aaatattatg caagagaaat tgattaacct    31080
aacttggatt ggatgtcttc tctcttgaat aaattgacct tagtaaaggt cagtgaacat    31140
agccacagcc aattgttttc agaactagga acaactcta tagttctgtt ttctacctct    31200
ctctcttaaa aaaattttt tttaaagctc tggaaaataa tgtagtcact aaaaatgtac    31260
atttaattta gtaacatata atttatgcac agtatcccaa tattatctaa attgtgatag    31320
gtgagcctct tcagtcattc aaagataaga ctttgggtta ggacttctca attttaatct    31380
gtcgtttaca agaacttaca gtgcagactc aaggcagaca tatgaaatgt tgggtcccct    31440
```

```
tggttattga gttggtcaat cagattggat ccatgtatca tggcatatcc acccatgaca   31500
tttgctttca gccatgttgt gtgtagtcct tggaacatac ttatctggaa cctgtacacg   31560
ttgaaaaatc atgcattctg gatggtttgg tcctactctt acttgatcaa ggatgtgcag   31620
ataatgtgag tctctgggat tttgccaact tttcggtgtc agaaccagtg ccaagaaaat   31680
tggcccagga cttagaaagg tcaagtaaag taatgaatcc agacaactta agattttctt   31740
tgcattgagt agattaagct aggtagttct ctttgactat acaatttgac gattagtggc   31800
caatgccatt gggctttctc acttactatc ctgttaaata ttgctagctc caagttagga   31860
aaaaacctcc tggagtggtt caaatgacaa tctaaatatc taactctttc ttttcttat    31920
tttggaattg caagtctaca tatttgtttg attttacaac agtcttctcc cttccctcta   31980
taccagtggt cctcaacccc tgggctgcag acaggtacca gtccatggcc tgttaggaac   32040
gaggccacgc aactggagat gaatagccag cgagcaagca ttactgcctg agcaatgctt   32100
cctgtcagat cagtggcagc gttagattct cataggagca caaacccac tgtgaaccgc    32160
gcatgcaaag gatttaggtt gcatgctcct tatgagaatc taatgcctga tgatctgagg   32220
tggaacagtt ttatccccaa accatcccca ccactgattc caccccaact ctgccccatc   32280
catggaaaaa ttgtcttcca tgaaactggt ccctggtgcc aaaaggttg gggaccactg     32340
ctctataccc taaactgtgt tgtagctgac ttttaaaggc aaatacatta tgattaattt   32400
tggaggtgtt cttgataatt cttctaaaga catcaaaggc tattattgag aaaaggttga   32460
tgattcttat tccagagtta gcagcttgtg ttagcccacc atactgggaa aaaagcctct   32520
gtccctggat ttgctggtaa gttcgtgaga ggttagatgt atgcttcttt ttgtgtgaaa   32580
taaagaaata atcccacataa aaaaatatgc actcaggaaa atcttgaggg agttttgct    32640
ccgggtgtgt ctccacacct cccggggaag attgccatcc aactcacacc catttacctc   32700
taaatgaagc atgaagatac agcccaaatc attagttctc tggtctcttc tttgaaactt   32760
ccacatgcag ctctgacatg actgcataat tgtggaggat aaaaacagtt ttaaatcaaa   32820
gagtcctggc ttcaaacttc agtttcaatt cacaccagct ttgctacctt aactaatgtc   32880
acttagtatc accagtgttt aaatttccct tgagaatttt caaagaaatg cagaacaatg   32940
catatctcag agatttgctg aaactattaa atataagcac tatataaatg aaagttatta   33000
tcctgaagct tattgttact gttttttgcta cttttgggt ttctttgagc aggtttctgg    33060
aaaagaacaa gcagccaaaa atgccatatg gattgactgt ggaatccatg ccagagaatg   33120
gatctctcct gctttctgct tgtggttcat aggccatgta agtattcaca ttctcttaac   33180
cctatttctc aaaatggtgc ccaagatcac ctgtgtcaga ctcaactggg ctatttatta   33240
aaatgcattt tcctaggtca catcatgaag cttgggaatc tacaattttc acaagtttcc   33300
caggtgactt ttatgcatta gtaagttgaa gaacatgact tcaagcattt aaatcaccca   33360
aaatatttt ggtctttct acattaaaaa aaaaaaaaa aaaaaaaaa aaaaaaaga       33420
aatagtacat tgattataat atgtttacta agtagaggaa aggactgaag gagttatcta   33480
agttggggcc caattaattt atttctcttt tggttttaat tatccagaca tcttttgcca   33540
cctttgccct tggaaattga acataaagca caacattaca gaggtgaaac agaatatgtt   33600
ttctcatatg tcataatagg gaattttctt cctgaagaag ggttttgcat caaaaaagcc   33660
atatataaga caaactgtat gttggaaaag taaagatat aacgactatt aacctccctg     33720
atgaatgaaa acagtaaaaa ttatgcttca aatcctataa aatgggcata tatgttctct   33780
acactgattt ctacaaagaa tcatagccac tggaaaaata actcaaaata tgtgtctttc   33840
```

```
tgataatgat ttttgcagtc tttgcattca cagatacata gtaacagaat aaatgagtta   33900
ggaaattaag atattggcac ttattaagta catcaagata aaactgtttc tgtctttgct   33960
tgaccttgac aaatgcaaca tccctatttg ccttcattca ctgtgaatct tctatcctcc   34020
attctccatg gatgggagct gcaacctccc tgagtctact ggaaattccc aaacaccatt   34080
ggtactacct tggccaaatg aggatgattc caactgatca gacccttaac atatcccagt   34140
cacatcatga tctgaacct tccccaagtt gagtagtttg gttattttag gtagtgaagg    34200
gagcagcagt taatagagaa aggtccaaag taggagagta agaacattta ttttccattc   34260
tatcactgaa catgagaagg gccaagaaga aacctccatt catattgact ctaatttata   34320
tcggtgaggt tgtccctaat gactgccctt ctcaccctga cacctctgcc ctcctattag   34380
acatcctacc ctctacccaa actgcttgct gaatctttgt aagattaaat tatttaatcc   34440
acaaatattt ataaattgcc tatgatgttt cagatcctgg aaatacaagg atgaacaaaa   34500
tatagcccaa ggatcttata gctgagtatt ttgctccaac aatgtgaacc tgatttgtgt   34560
agcccaaaga aacataatca ataagggctt tttaaatcga catttaaact ccattcttgc   34620
ctgcctaaaa ctaattcaga tcatctgact ctcttagtac ttcaaagcac tggaggaggg   34680
aaagtaaaat aaaatattta cctttcaaca attgtgaagg caggttttat attcaaaaac   34740
taaaccaccc aaaggcaaat taaaatctta gcttttaagt ctctcactct tttctacaac   34800
tcaataagga tttcaaaaat cttataatct agtctcagtg gaaatccact acactacact   34860
ttgagaagct tgaagccagt catttctttc taagcttctc attcatgtac tctcgggagg   34920
caaatttaga tccttctctt tccgcaaagg cagagctgag accaatttgt gcatgactgc   34980
atcaccaagc caaaatccgg cacagggctg gcacatcata ggacccagtg aatatatgtt   35040
aaccatcaca acttgccaag tactttttct gccaaatggc ttttctcact gctaacctcc   35100
tgccaaacct ctgccctaga aaactctcat ctaattgcac acaaagttag agctctacaa   35160
cctcagggcc ttcacagaat tatctctgcc cctcctcacc acagctgaca catgacctaa   35220
ggacactgct ccctggtggc tccttcaagt agaggggctg ctcttttttt cacatcacca   35280
tgtgctgaga ggcctggtgg agtggatcag cattctcttc tcctgatact accaatgatc   35340
cttctcttct cagaaactta cacaaactgg ttgcactctt attttattgc tatcgtgcac   35400
tgaccttcag ataatttcct ggtatccggt tcatgattct ttattcccct ccaactcttg   35460
ccatcattct gagtgaattc aaagtccatg tgtgagagtc acctaacaat gtatcttcac   35520
agttccttgt tctctgttct actaaacctc atctcaactc ctctttagca gatttctcct   35580
gtagccatcc tctggatctc agaagtaatg ttttgctgat ccttagaccc agaatgtggc   35640
catggacagc aacaaggaat gttagaagaa gccatctagc aatgtaactt cttaatttcc   35700
tgtcttctct catttctcac ccctactatg actgctttt tttcaacctt agcatatttc    35760
tagttcctac acagatctat atcatttaa tttatcagtc cctttccagg aacactttct    35820
tcactaattg gtcccatcac aaattcatcc gaaccctcaa tttcttgctc ccttgacctg   35880
ctcttctgga gttccaaccc caaacactcc acagaattaa ccatccttt tctgagccac    35940
cttgtacatc ttgccattgt ttattatcat acttatatta atagcattga actgctgctt   36000
ttcccttttcc aacttatcac ttctattagc tttctgaagg cagagaccaa gtctaaagta   36060
atttttttgt tccccataac ctggtatatt gtttggtcaa cataattggt gctcaatatc   36120
cccttgtgga atttgaaatt taaattaatg ttgcaggttt aggctgacat acaattttgg   36180
```

```
gttgcagaga gtatctaaac agtacctact gttgggataa atactttatt gtcattggct    36240
acagttcaaa ctatacatac atatatagag attggagtaa aaactgagac agatagctct    36300
ctgatatatt tgtaatggta atgaaaatga cattttgttt taaaattttc ccttcatgtg    36360
tcttatattt tttttttagca accccattaa ctgacctata tgtcgttatg tactaattta    36420
ttatctctca aatggtcatt ggttaattcc taggcaggaa ttgttgttgt tgttgttgtt    36480
gtttagggcc acattaaagg caaagcttga gtgcacccca ggcaaagtga gaggaagagc    36540
tgagtaatca ttgaccacag gccagctgat gggaatcaat cccacccctct catcactcag    36600
tcttacactc ttctccattc tcctctattc tcatcttctt tttctttttat acagaggctt    36660
ctcaatttat ggtggggtta tgtctcaata tacccaataa acaatcacaa ctgaaaatat    36720
tctaagtaaa aaatgcattt aatataccta atctaccgag tactgaatat catagcctaa    36780
ccttccttaa atgtgctcag aacacttacg ttagcctaca gtagggcaaa atcttctaac    36840
acagagccta atttataata aattgctgaa tatccatatc acttattaaa tactgcacta    36900
aaactgaaaa atggaatggt ggcatgggta tggtttctac tgaatatgca ttgcttttgc    36960
gctattgtaa agtcaaaaaa tcataagtga aatcattgta tattgcagac catctctagt    37020
aggacaggat ttcaattatg ttacttgcca tgttggtaaa tcgtaccttc aacaaatatt    37080
tatttgtcgt caggcaaaat ttcttcagcc actttgaaaa acaatgtgga agttcctcaa    37140
aagattaagt atagagttac catatgaccc agcagttcta ctcctaggtg tatacccaag    37200
acaagtgaac acatatgttg acaaatgatt atagcaatat tattcataat agtcaaaaag    37260
tggaaacaac tcaaatttcc atcaacttat gagcagaaaa acaaaatgca gcatattcat    37320
gcaatgaaac atcaatcagc aatcaaaagg aatgaagtac tgattcatgc tacaacatag    37380
atgaatcttg aaaatactat gctaagtaaa agaaaccaga tacaaaatgc cacatatatt    37440
attccatttta tatgaaatgt ccagaatggg caaatccaca gagacagaaa gttcattagt    37500
gattgtcaga ggcttgggga aatggcagga gggaagggg agtgagttat aatgggcaca    37560
ggcatgggga ttttttatga tgaaatgttc caaaaatcag atactagtga tggttgcaaa    37620
actctatgaa tacaccaaaa accgctgaat ttcacacttt aaaatggtga atttctggaa    37680
tgtaaattat atctcaataa gctgttaaag aaaaaatggg caccccttcc ttcgggattg    37740
tagctatagc cacacttgaa ggtgtggctt ggcacacagc acagactgta tttcagccct    37800
cactcactcc ttctgtctgg agtcctacct attagataaa gaataggta acattgttct    37860
gggcctaaca tcggtaatct ctcagagcat aacttttttgt agaaagattc ccatccaacc    37920
agaggtaaat gtaggaagga aatttaaaaa gtgaagcaga aaaagaaatt catatgctgc    37980
atctattaaa agtttggccc atgttgtaga aatgaaaatg agaaatgctt tattatttgc    38040
tttattattt taaaaggaac aggctctcct aatatttttc taataatgaa tgctacatta    38100
ttactgaaaa gtgatgctaa cataaattta taaattcgta gcataaaaat gtatttaact    38160
ggttgctcga ctgtttaaaa catggcttcc ctggaaacca tcattctcag caaactaaca    38220
caagagcaga aaaccaaaca ccacatgttc tcactcataa gtgggagctg aacaatgaga    38280
acacatggac acaggaggg gaacatcaca caccgggggcc tgtcggggggt gggggggctag    38340
gggagggaga gcattaggag aaatacctaa tgtagatgac gggttgatgg gtgcagctaa    38400
ccaccgtggc acgtgtataa ctatgtaaca aacctgcatg ttctgcacat gtatcccaga    38460
acttaaagta taataaaaaa caaacaaaca aaaaacaaa acatggcttc cttcattcta    38520
caaattttgc ttcctttttca ttaaccttttt atttctgacc tacagtagat tttaaaataa    38580
```

```
cttttttctt ttctttctct ccgatttcat aagtatttat tcatggcaaa gattttaat   38640 gtgactcttg tgattgttct agggaaatat gaatataata ttttaaacgt ttaaagggaa   38700
aatagtaaag tttataaaag cttgttttt attttgtcaa taatgaaaaa gacatttctt   38760
aacaatgtca tgagtatgct ttaaggcaac aaacaattat aaactaaatt aaatatttaa   38820
tgtaattaaa tgtgaattaa attaaaatat agcaatgttg ccacaaatta agattttgaa   38880
ccaaaagctt tgtcctagat gaaacgattt gaccagctaa aatttgtctt tatagttctc   38940
ctgcctgtac attttgtcat tttggggtaa acttctcagt caccaaattt ggatgccatt   39000
ggatcacact gcaatatgtg ccactaagct ggatgactct aaagtagaga ggaacaagtt   39060
tgagatgatg tccgttagga attcatagcc agttcctagg aaaagctacc ctaattctac   39120
agctagatga tcaaagcctt gggaaacaca ctcaattcta gcaaaacttg agctccacaa   39180
gttctaagga caatgtagcc aatatcatgt aatcacatct ggggataaaa catggtaggt   39240
agtttaagct ctgatgaaca tgaattacag aaaaaggagc taaactaaat ctaggttttt   39300
gtttccttaa atcttcttag tgggctctat ggctttaata aagaattaat tttattttt   39360 aaggaaaatt tagaaagttt atggttcgat tgtctgcctt cattaactag gaatactgga   39420
ccacgtgtaa ggcatttatc accacttcgt agcaccctaa gttcagttct tttgaggaat   39480
tagcactctt tctgaaagtt aaatctgcaa atctaaacat gccaaatgac aaattaaaaa   39540
aaagaaaaag aaacacacta agtttagaag aacttaaaac atctaattaa atatacttgg   39600
tttaatttgc agataactca attctatggg ataataggc aatataccaa tctcctgagg   39660
cttgtggatt tctatgttat gccggtggtt aatgtggatg ttatgacta ctcatggaaa   39720 aaggtaggag aaaaggcaaa gaagacaaat catgttctcc ttggggatat aggatataca   39780
ggttgaatta ttcatagaat tctggatcta ggcacaatgg ctttattatt aatttttttt   39840 taactttat tgtggaaaat gtcaaatata tatataagtg cacataattg tgtagtaaac   39900
ttctatctac ccatcataga gcttcaacaa taattaactc atgaccagtc ttgtttcatc   39960
tgtattctct ctacccactt ctaccttact cattttattt tgaagtaaat cctaggtacc   40020
atatcacttc atcaataaat atttcagtat gcatttctaa aaaaaaaaga actctgaaaa   40080
aaataattat agtataatta taccttaaaa actagctgtt tctgaatacc ataaaatatt   40140
gccagtattt tcaattgtat aataactttt tttttttttt tttttgaga tggtgtcttg   40200 ctctgtcacc caggctggag tgcagtggca cgatctcggc tcactgcaac ctccacctcc   40260
cgggttcaag agattttct gcctcagcct cctgagccac tgggactacg ggtgcctgcc   40320
accatgcccg gctaagcttt ttgtatttt agtagagaca gggtttcacc atattggcca   40380
ggctggtctc aaactcctgc ccttgtgatg cacctgcctc ggcctcccaa cgtgctgaga   40440
ttacaggcat gagccacctc gcccggcctc ctaacttttt aaaaagtatg tttcttttgat   40500 tctggatcca aataaggctc ttacattatg attggtttat atgtcttta attctatttt   40560 aatccatgaa ctcacattcc atcttttgct ctttctctct cttctttttt tccttgcaat   40620
ttatttgtca aagaaaagag tttcccatta tcaggatttg ctaattgcat taccatcttg   40680
tagtttaaca tgctcttctg tctgtatttt ctggttactc aacattgtga ttcatgtaaa   40740
attactcaag caatatgaaa tactctgctt tctaatttaa agagggcac atagaaacat   40800 aactaggtat atataaattt agaaaaacct acttgagtag cacatataaa tactaagagg   40860
aataagatta gttggtgtga ttggaaacat ggaattacac atgaattatt tcatgtagga   40920
```

-continued

```
ggtaatttat gcagaagata tggaaatggc acaggagatt gaggaaaaag tcatctctgg    40980
tgagaggaat actgtaactg aaaattttgt aggtggaggt gggcaaatgc caaactaagt    41040
aaatgagaat tacctagcat aatgcctaac acaaatttgg tgtccaatga atggtcatat    41100
ctgtaaactg gtaataaagt atatttacac cttaacctga atcacagtgg aattcagtca    41160
ccctttagat ttccagcttc ccaactgttc tttgtatcat taccctatta ttaattccca    41220
cagtttgaga acttgatatc cccagggcct attgttgcca cggaaccaca ggcctgggag    41280
tggtaacagg ctggaaggct tggcggaggg ttggtgagag taggagaaaa gggtgctaca    41340
tcatcccaaa ctcagaactt aaatgaagta tgtgcaactc tttttttttt tttttttttt    41400
tttgagacgg agtcttgctc tgtcgcccag gctggagtgc agtggcaaga tctcggctca    41460
ctgcaagctc cgcctcccag gttcatgcca ttctcttgcc tcagcctccc gagtagctgg    41520
gactacaggt gcccgccacc acgcctggct aattttttcg tattttttagt agagatgggg    41580
tttcaccgtg ttagccagaa tggtctcgat ctcctgacct cgtgatccgc ccgcctcggc    41640
ctcccaaagt gctgggatta caggcgtgag ccaccgcgcc cggcctgtgc aactctttac    41700
atgaccaaac tttcccagtt taccccaaga acccaatagg gaatttgctt tatatttaaa    41760
aaccagagtc aaatcagcac aatcgaagaa gtcatcagat taaaggtgtc ttcacatctc    41820
cacctttttct agctttgaaa ggggagtggt gaattctacc taaagagagc attttaactt    41880
atgactcagc gttcagttga gacacaaagt tattttgctt ttcttcgaag gagctcagaa    41940
tgaccctgtg cataaaatta atgtaaagga aacaagacta acaagaagg ctaataagca    42000
gcctagtgga atgaaaggaa atctttattt gtatcagtca aaattgatca atatattacca    42060
ttatgtttgg ttcaactaaa atagtctgag tggatgtgat tgaaacccgg atagcaatag    42120
ggaccgtgca aaggaatatt gcaacaacag tgatgtgatg aagccatgca aggtatggga    42180
ttgaaggaga gaaaggcaat tctggcttca tggactttca aatgcatgtc tttcctcagg    42240
ccttgaacgt ggctacccag gttgtctgtt tgtatttttgt ttatgtagaa tcgaatgtgg    42300
agaaagaacc gttctttcta tgcgaacaat cattgcatcg gaacagacct gaataggaac    42360
tttgcttcca aacactggtg tggtaggttg ttggctttat ttcttgcaat gtctcttcac    42420
tgaaagggtg atgttcacag ggaaaggccc atgaattcaa attaaataca gagctggcct    42480
gtctgaatca gggaataatt taaatgataa atgcttaggt aaatgtaatg ctgcgactgt    42540
tggccagagt cagcaaatca ctttggcctc tcctctctcc tgtttcccta tctttaaaat    42600
aagaaagttg aatcagtttt ttaagatccc ttctagcttc aaaattctaa aatctattat    42660
cttggaataa taagaagtg acagttaaag atcctatttt aataaacaaa acattcatc    42720
attagaatat caaagacctg agatgggggg gaggacctct cttttttttt tgagacagag    42780
tcttgctgtg ttgaccaggc tggagtgcag tggcacaatc ttggctcact gcagcctctg    42840
cctcctaggt tcaaggattc tcctgcctca gcctcccaag tagctgggac tacaggcata    42900
tgccaccgtg cctggctaat ttttgtattt tttttagtac agatgggatt tcaccatgtt    42960
ggccaggctg gtctcaaact cctggcctta agtgatccgc ccacctcggc ctcccaaagt    43020
ggctcacagg agtgagccac tgtgcctggc ctggaccct catttttaat tgcacaagta    43080
aatgtttact tctatagtgt ttgaagacat ttttttcact attcactttc ttaatttctt    43140
taataaataa tataaagaaa atataaaaat attaaaaata gtataaaaag cagcacagtg    43200
ggaatttatt atttcttaat tcgaatgagt taaggcattc gatgatgttg agttatgcat    43260
tcaagaacag tctgctttca ggagtttgaa gattttttaa agaactaaaa gtagaattac    43320
```

```
tatttgactc agcaatctca tcactgagta tatactcata ggaaaatgaa tcgatctacc   43380
caaaagacac atgcaatcat atgttcattg cagcactatt cacaagagca aagacatgga   43440
atcaatctag gtgtctgtca atggcggatt ggataaagaa aatgtggtaa atatacatca   43500
tggaatacta cacagccata aaaagaaca aaattatgtc ctttacagca acatggatgc    43560
agctggaagg cattgtccta agtaaattaa cacagaaaca gaaaatcaaa tactgtatgg   43620
tctcacttat aagtaaaagc taaacactga gtatacacag acataaagat gggaatagac   43680
actggggact caaaaaaggg gcagggaagg agagagaggg gaaagagttg aaaaagtacc   43740
taagtggtac tgtgttcacc atttgggtga tgggttcaat agaatcccaa acctcagcat   43800
cacacaatat atccatggaa aaaacctgca catgtacccc ctgaacccga agacaaagaa   43860
gtttgctttt agggggtag gtgttagttc actctttctt cccacccact caacattatt    43920
tttcatagta ctacatttca gaaacagcta cgaaaataaa ctaaccctga caaggagtat   43980
gcatcatcta tatttttggg ctccatgggg cccataaggg agagaagcta ttgtatccac   44040
agaaacatct tcttcctccc agacctggac cctatacaat cctatgcaca taattttgcc   44100
tatttccttt aaaaggtaa aatttcatga ttttaaacat tttatcaaaa tcccagaata    44160
cctattaaaa cctcacaaca ttcagcctgg gaaagctgat tgctaaaaca aaagaaaacc   44220
aaacctcaca acaaagcact taccttattt ccttattttt ttccctgtct aggttagaaa   44280
ctccatgcag acagaaacca atacccatta tctagtgcag tgcctggcac aaggagggtc   44340
ctcataaaat attaactaaa tgagtccatg aatgaattta gttgctctga gagctacaga   44400
tatggtagga actcagagga agaagcagtt catcccgact taggttccag ggaatcattt   44460
agtggtttct ccctaaaaaa ccactcgtgt tcccagaggc ccaaagtttg ctgcggcact   44520
aataacatgc caggggctca caggaacagc agccatgtaa aaagaatcta agtaaataga   44580
gctgacagtt actcagcgct gagccattga catagttcat cttccagatt tcattatcta   44640
tgaatcatag atggagaaac ccgggctgaa aacagttaag tcccttcctc aagggcacgt   44700
agcaagtatg tgcaagtacg tggcagagct gggctataaa cccaagttat cagttcccttt  44760
ttggaagttt ttattttatc ttcaagctct tttggtgctt gattttactt aatattttc   44820
ttggtgaagt cagtgttatt taatttggat agccaagtag tcaaaatata ttctgttatt   44880
gtcatcaaga aatgtctcag tcccctcttg ggcatggtgc tatattgtta cgtatcataa   44940
gagtgaaaaa cagaaacaga agcagcaagc atatgggttt ttaactaaaa aaaaaaaaaa   45000
aaaccaaat aaaaagtaat tgtaaggaac tgtccttatt accaactgtt ccagtatcta   45060
ttctgtacta tgtaagcaag acagtgagaa agaagaattt aatctttct catccctaca    45120
actagaatgt gccctatga ttctttatat aaaggatcca aaaacacctc acttattaac    45180
aggaagtgac atatcaaacc tacttactca ttttatgctc ctctgtatta aattttttg    45240
tgtgtgtgtg ttggagatga gagtggaggg taggttgtag gggtgtcttt gtcttctcag   45300
gctgctataa ccaaataccca taggttgggt ggcttaaaca acagaaattt attttctcac   45360
agttgaggat tgggagtcca aaatcaaggt accagcagag tgaggtcttc ctgaggattc   45420
tctcattggc ttgtagatgg ctgccttctc tctgtgccct cacatggcct tctcttctg    45480
cacaaacctc cctggtgtct ctctttattc ctataagggc accagtcaca ttggattaga   45540
gccccatgcc tatgacttca tttcactttg tctccttaaa ggccttatct ttaaatacag   45600
tcacattggg gcttagggct tcaacatagg aatttgggag gatgcaattc agttcataac   45660
```

```
aggagtacat tatgagaacc tttggtctca aacttcctaa gatagcacca cacattttct    45720
aaaacactga gttcaactac aaagtttttg caactggctt gaatgaaaaa ttctttattt    45780
cttttcctag gagactatag tgttttttaa aattattttt tattatgata aaatacatgc    45840
aatataaaat ttgccatttt aacaattttt aattgtacag ttcagtggca ttaagtacat    45900
tcacaattac tactatctat tactaaaatt ttttaattgt cccaaagaga gatttttact    45960
tattgtaacc agtaggcaat atctcctcat ccctaccttc tccccagccc ttggtaattt    46020
cttatctact ttctgtctct atgaatttgc ctattataga tatctcacag tgtgcttggt    46080
tccatgtcta tagatcaaag aatgcttgag cttggaggga tccagtggcc caagttcctt    46140
cctggtacag atgaggcccc tgaggctgag acgatgaagt agttgcccaa attaacatga    46200
ctgcttaatg gtaaagcaga gtctcgacct caagtttcct gcctcttcag ggctcttcc     46260 actaaaatgc ttgaaatctc tagaatgaca atcatagaat gagaatctga ggctcactgt    46320
ccagcatagt agccactaac cacatgtggc tatccagtgc ttaaaatgta gcttgtctga    46380
attgagacat acactgagtg ttaaatacac accagaattt gaaggcttag tatgaaaaaa    46440
gtaacataaa atatttcaag aataatttt atattggtta cacttgaaat gatactttgt      46500
acatatttgg ttaaataaat tacaatattg aattaatctc acatatttct ttttgtgtgt    46560
gtgtgtgtgg cagggtcttg ttctgtcatc caggctggag tgcagtgtca tgatctcagc    46620
tcactgcaac ctctgcctcc tgggttcaag caagtttcgt gcctcagcct cccaagtagc    46680
tgggattaca ggcgtgcacc actatgcctg gctatttttg tattttggt agagacgggg      46740 tttcaccatg ttggcctcgc tggtgtcaaa ctcctgatct caagtgatcc gcctgcctca    46800
gcctcccaaa gtgctgggat tataggtgtg agccaccgtg cctggccttc tttttatttt    46860
tcttaaagtg gtaacttgaa aatttaaagt aaatatgtga cttgcattat atttctatta    46920
aacaaccctg gtctgaggat tcatattagg gcaccacctc tctatttagt ggttatgtct    46980
tccccgacct ccatacccaa tatataatct ctattctcta agaattatat atcacataaa    47040
agggcaggaa tattcaaagg tgaccgaact atcaaaaatg gtttatccaa tcaccttatt    47100
ggttaaaaat gaaatacttg ggaagacctt agatgttcac atttcctctc agggaaacaa    47160 tttttaaca aacattaatg ttgtgtttgt ataataacag gaataaagca gaatgagctt      47220
aattaagaaa agcaggctct gtaaggatag tgagtagcct cagccatgga ctcctgaggc    47280
agagatgcag ctggactcag aaacagaaag gaactgggcc tggagcccta gagaggctca    47340
gtgaatcctt cctctcccct tctcatctct gtgatgcaca ctggcttctt tcaggtctca    47400
gtccacatga tgatgatgat gatgatgatg atgatgatga tgatgatgaa cagcaacagt    47460
tatgaaatgc atactacatg ccaggcactg tgcaaagcac tttgtatgaa ctagctcatt    47520
taattctcat tcaatcagca tttaatgtat aattttttcaa ttttgcagat aaggaaattg    47580
agatacagat agatttttaa aaatttaccc aaagccatat agctaataaa tggtagtcaa    47640
gatttagaat caagtaattg ggtgcttaac aatatgctgt atagcctctt attctgaaga    47700
atggttacca ccaagaatat ccagattgca tctcctaaaa tgcacagtatt tacttcatag    47760 ggctgctgta agaattacat gagatgtggc aaaaatctta gcagagttcc tgacgtacag    47820
catgtgctcc acaggtgtca gctggtagta ttactatttt tactgtctgt tcaagagagc    47880
agctagactg agactagact cttagtattg atttcaagtt atctttgaag ggattcagat    47940
tggcaagcac aagagtcaga ccctatcctg agccctcaac tgtttgcagg aaggaataat    48000
ctcttgtgtc acatgcagct tgctggggct tcaccttgtg aattagggac aggggagaa     48060
```

```
gtgttggaag gcagcctacc atctcaagtg atgcaaatta taatctacca aaggaatgaa   48120
tgaacgttgg tctggcaaca aatatcacca tcccatttta tttactaaac ttactaaacc   48180
actttagcaa gttaaaagta gcactgaagg cagatttaca tattctgagc tctgaagtga   48240
ggcttttctt ttatgggcta tattgatggt agctttaaaa ctacaaatat cagaaaaact   48300
aaatttacag tggattaagg aaaatggggt ttattttttc tcccataacc ataagtctgg   48360
agacagggct ggcatctctg aggatctctt agccactttc tcaaggttgc aagggagaca   48420
ggtgctggga atgactgtta gaaggtcagc tatgtgagca gataagtatt tgacttcaaa   48480
agaaacataa cacttagtgg aactatgttc tttgcagagc cctacctaat ccattcatct   48540
aaaagtgttg caacataggt aggagaatac gttgtctggg aaaccacaaa ttacagtact   48600
atgtgcatcc cctcataatt tcaccttaac aatttcgtta cagaggaagg tgcatccagt   48660
tcctcatgct cggaaaccta ctgtggactt tatcctgagt cagaaccaga agtgaaggca   48720
gtggctagtt tcttgagaag aaatatcaac cagattaaag catacatcag catgcattca   48780
tactcccagc atatagtgtt tccatattcc tatacgaa gtaaaagcaa agaccatgag   48840
gaactggtaa gtgctactta attattttc tcattagcat tttggaaata aataatact   48900
tagttgaaga atcaaaaact gggaaaaatt ttggcctcta gaaggcaaat gatagatgtt   48960
ttaaatcatg gtgtgatcct gttgagagtc accctgggtc agtgttctct aagggaatat   49020
aaagaacgtg ccttacccta caacacaca ctttattcta gcacgtgggc ttcctaagaa   49080
aatgtcagac aaattccttg aaggttagga aggaactact actacacttg acctgatctg   49140
catgtgaagc ggtataagca aggatgagta tggaatcatg cgacagcttt gtggtcacta   49200
gcttcctaca acagcacacc acagattaag tctcaacaca gcactcattg ttttggtatt   49260
agcagcagga attgttcctg ccctgacttc cttaaccctc agggttttgg tcctattaaa   49320
gtacctccaa ttttagcatt gaggagagag tctgtttttt ggaacataac agacaataca   49380
ggaaattcaa agaggactca cacaatttga tactcccta gcactttta gtccaagata   49440
ctgtatgttt gggttcatgg caaaagatgc aaggattctt gaaggattgt agctaggctt   49500
tgacaaatcc tcatcccaga tgctctccag acagtggaag tgttacatca acagccccat   49560
tcttgggaag ggactaattt ttaggtagta gcttgtttct tagtgactca ttttttttc   49620
tggctctctt aacagaataa aatatagtca cattacagga gctagcaatt gctgatgaca   49680
aatataagat tatttgcatt ctctgaaaat agcccattta gaacataaat gtacttgata   49740
cttgagcttt tttcttctca agggaaaact gttaaggaaa gcacctttca aaaatattat   49800
ctttgaagaa ataaaggaa atttatcatg atttgggaag tagaattagt ctaattatgc   49860
tttttttttt ttgcatcact gccagcacac atatatgttg agagccatta cgtgtaaaat   49920
accttgtcaa tggatgttta agaagcatt aggtaaaatc ctgccccttta agagaatgtg   49980
ttatggttag ggagctcaac cattagcaaa tgttacaaat agttgtactc taaggcgaca   50040
tagagtaact actaaatacg tggcacagac agtacaactc acttctaact agaatatcaa   50100
gggatggctt cactaatgca ttcagaggga aatgctgaga taagtgagga gataaagtag   50160
ttactgtcct tgaggaattt acaatctatt aaggggggga aaactacaa ataataaagt   50220
gctgttgatg tcaaagatca gctacatttt agacaggcat tgaaagagga tttctatagg   50280
cagacaggga aggaaggacc ttccaagcaa agaagttggt gttcaccata agaggatgca   50340
aaagtggagg gtgatagcat cagaaagtag attaggttgg cttctgaagg ggtgtgactg   50400
```

```
tcagataaat ttgtatttca ttatgtagac aatggggtta cattaaaact tatttttga   50460 acaatgagat ggcataaaat aatatccgct gataaatctc ttgagttttt caagaaggta   50520
acagtgtata ccatgatgct agttccaatt tccgaaaagt tccagataag tgagaacttc   50580
agaatagatt tgacaaaatg aatatcaaca gacaaaatga agtcaaatgg gggtcttagt   50640
tattatcctg ctccatacca gaggcataat cttttttgat ttgatgaatc tatggaagtc   50700
attagacatt ttacacaaga agaaaataga agttgtgaga aggataagaa gtgagtcatg   50760
catgcattag gtgtttgtat gtgtttagaa aggttggatt taaagtttgg tgataatttt   50820
gttcagaaat ggagtacctc taagcctttg agatgtagtt atacttcatt ttccataata   50880
aatgagttcc caaaaaggca tgtgataatt tttttctgca aattaatata tttatttata   50940
taaattattt caatatattg aaatagttta tgtttaaagc cacccaattg tgattgccat   51000
aaagtgcaca tattttaaat taatttgttt accttattta tttgccttt agatgaatct   51060 agattttcta cctgtatact ttgattcaat taatgtatga ttattttta gaaacttcta   51120 cttgtcatgt ttcaaagctg cacattaact gaaattctat atcttttgc ttccagtctc   51180 tagtagccag tgaagcagtt cgtgctattg agaaaactag taaaaatacc aggtatacac   51240
atggccatgg ctcagaaacc ttatgtaagt atttcttctt atgatcttag agaactttga   51300
gctactaaag aaatctgtgt gatctgtttt tctttgtgta tttaattttt ctgaattaaa   51360
tagggtcaca tgtaatacaa ctgaattgta ataattagga acagaagcat aatagctatg   51420
acaatgctga acaaagctat attaataaat gagttactaa aaagaagcca aaatcctatt   51480
taagaaatca tatttatcac aatcaagtag gaattacaga attggcatca tactagttga   51540
gtgaagcaga aaagttcata aaacttttgc atgattccca gggccaccat ggaaggttgt   51600
gcaggttgta cactacacta atctagggca tgccatttgc atcaagtgtt ttttagtgtt   51660
agcctgttcc caagagtata gctcataaca cattacagtt gattgtcttt aatatatatt   51720
acacacacaa aacttgtgac aaaactcttaa caaaaagttt tgattaattt ttgctgaaag   51780
atatttagtg agtaactcct atctacacac agtgggagga cagactgatt ttgcccttt   51840 gaagtttgaa gggagatggg aaaagaggag cataaaataa acctgtaacc aggcatcaga   51900
aaactacagc ctgaaggcca aatccaggtt ttttccatttt tttttttttt aatgattaga   51960
aaaaaacaaa aagaggccag gtgctgtggc tcatgcctgt aataccagca ctttgggagg   52020
ctgaggcagg aggatcactt gaggtcagga gttcgagacc agactggcca acatggtgaa   52080
accctgtctc tactaaaaat acaaaaatta gctgggcatg gggccttcca tgtaatgcca   52140
gctacttggt tggctaatgc ataagaatta cttgaacctg ggaggtgggg gtggcaatga   52200
gctgagattg tgcaactgca ctctagcctg ggtgacagag tgagactcca tctcaaaaaa   52260
ggtcgaaact gtatttatca tgaacactaa aatatgtaca catttttagtt aacatgcatt   52320 aaactgtaac aagtcttctg gcaattgtag cttttcatgag atgcttccca aactgtatta   52380
gatagatgct aaaattataa attaaaattt tgggtcagac tttgccataa acctggactc   52440
aatttagcac cccccaaaa aaagtcgat tattcaatta atgcggttgg aaaacctaac   52500
aagttaccta gaaaaaaatt aattggatta ttaacatgtc tttcaccaaa gtaaattcca   52560
ggtacagcat atattttcat atgaaaaccc tgcataaacc aagttgaaat ctcagtaagg   52620
agaaaaaatt cttgtgaaag gagaaatgaa tgaaggaga aaaaaaggtc tacatgccaa   52680
acaaagctaa taacactaat gtcgtttta taagcaattg ataaaatgaa ccaagtagac   52740
aaatgaggaa ggacaattga taggaaatat aaagatagcc aataaatatg ccaaacaaat   52800
```

```
gtgcaactca ctgataatca aaaaacataa attaagacag ttggatatta tttttcgccc   52860
ataaaattat cagaattcat aattcctatt gatggtatgg gaaggggaaa tgggcaaatt   52920
catacccigc ttgtggaagt ataaatgaat tcagttcttt tgacgtccat ttgggaacat   52980
gccgtaattg caaaaagtac agagccttag actagcaaat ctattctagg gaagaatatt   53040
ctaaagagac aaagaagcaa ttatgtataa acaagggtac tcattgtaaa gttgtttata   53100
ttagttaaaa actgaaaaaa atctaaaggt atacaaacaa ataaacattt aaatcaaaca   53160
attcccagtt tgtaaattaa tttgaaacgt ctgtatttca acaatttctt tcttcttctt   53220
ttagacctag ctcctggagg tggggacgat tggatctatg atttgggcat caaatattcg   53280
tttacaattg aacttcgaga tacgggcaca tacggattct tgctgccgga gcgttacatc   53340
aaacccacct gtagagaagc ttttgccgct gtctctaaaa tagcttggca tgtcattagg   53400
aatgtttaat gcccctgatt ttatcattct gcttccgtat tttaatttac tgattccagc   53460
aagaccaaat cattgtatca gattattttt aagttttatc cgtagttttg ataaaagatt   53520
ttcctattcc ttggttctgt cagagaacct aataagtgct actttgccat taaggcagac   53580
tagggttcat gtcttttac cctttaaaaa aaattgtaaa agtctagtta cctactttt   53640
ctttgatttt cgacgtttga ctagccatct caagcaactt tcgacgtttg actagccatc   53700
tcaagcaagt ttaatcaatg atcatctcac gctgatcatt ggatcctact caacaaaagg   53760
aagggtggtc agaagtacat taaagatttc tgctccaaat tttcaataaa tttctgcttg   53820
tgcctttaga aatacaacca tgcattccgt ttgctccacg gtaattaggc gatggcccag   53880
aaagggagg ggtgtcaaaa acgacaaaca tagcctctca ttccagctca gctgctcaat   53940
aaacactgtt gaacgaatga atgagtggct ctaggtactg tcaacaaatg ccgcattttg   54000
cgcatttaca acagctgttt atggtaagga attatgtaat aaaaagagaa aactcactta   54060
aattcacttt taattgggaa ttttagttct cccgggctcc cagtttcctt tcctaggatc   54120
tctcacagag cacagattcg atttccaagt cccgccgcac tcttaccgct cgcatggaac   54180
cttacgccta gagggcgtgt ccacgaaggg tggtgtctgc gcactgacga ctaatctgac   54240
ggccggaagc tgcctgggtc tacagaggaa cagggcaaac ctctgacttc cggcggcatt   54300
ttgaggcggt cctcctagcg gcctggtagt gttttttgttg ccttttctta atctacaatc   54360
tcttcgttat ttttcttcct gcgacccagt ttcgcttgac cctggagagg cggcgggcgg   54420
gttggttctg cttctcagcc atcccggggg ctcctcgcta gccaagagcc ggttcccggg   54480
agccgcgcgc gcatcgcttt ctcctcgtcg tcgtcctcct gggtccaggc gcgggacag   54540
agtcgcctcc cccgctcctc ggagcggcgg cggcggtggt gcctccggac tgcacttgcg   54600
aagggagctt ggggaggaag taagcgttct gtgaattggt gtgggtatct ggggaaggca   54660
ttgagcggac ccgtaatgcg gaggcccggg ttaccccccc ccgtctttgc ttgagtcact   54720
gggattttga gctttccttg agcatcccac ccttaactct gcaatagccc cctgtgctca   54780
ggcgtaattt ctcactctga ttatgattct ggcatttgtc taaggcgat aagtagactc   54840
agacaatagg ctgtacccct cgttaccatt tgatgtaagc acgggaaccc ttgtatggtg   54900
ttcgtatttg tgtgcgatgg aagggtgcag caatttgggc ttaaatttag aatcttcctc   54960
tatactcatt ccagatctgt tagagaaaaa catcttactt gtgattggtc ttgttttttt   55020
tttttttttt ttttcccctca gcagtgataa cgatttaggt cctgggaatt gagtgctact   55080
ttatcttcac aagccttagg taggtagttt tggcaactgt cagaaacggg ggaaagtgga   55140
```

-continued

```
atagaaagaa gagagtctgt ttggcggcat tatctctctg taataggcta acgcaattta    55200
tgtggtttga aaattattta gagttgataa tacttgaatt atgttggtaa gatgttgttt    55260
gtgaagggta gtcttaaggt atttggttat actatggggc tttcaggtaa ttcgaactac    55320
tttgaaaatt atgggagtat gaagtctctt aagattttg gattttaaa gtagttttaa     55380 aaatttggaa aacatcttta cacctcaagt tttcgaagtc cgcgataccg ttggagaata    55440
aatacttatg cagttcagtc tatgggtata tggtgccagt tagcgggtc tagttctgta    55500 acatttgaaa ttactggctt tagtacaata tattggagcg ttttgtgaat acaatctata    55560
gattttcaaa taatttttaa tttcttaatg aactatttac attataacag atgacagttt    55620
caactagaga ctagcaaagt tgatgcaagc ttgtaacaat tgcggcttta aaaatagttg    55680
cactctgaaa ctaaggcttt cactctgtgc atctggtagg attcagtttt atcaaatgta    55740
tgcctcttac tggcttcctg attactggtc attctaaatg aacattgcat attttgagat    55800
ttgcaagctt atgtgatttt catattt                                        55827
```

<210> SEQ ID NO 4
<211> LENGTH: 423
<212> TYPE: PRT
<213> ORGANISM: Human

<400> SEQUENCE: 4

```
Met Lys Leu Cys Ser Leu Ala Val Leu Val Pro Ile Val Leu Phe Cys
 1               5                  10                  15

Glu Gln His Val Phe Ala Phe Gln Ser Gly Gln Val Leu Ala Ala Leu
            20                  25                  30

Pro Arg Thr Ser Arg Gln Val Gln Val Leu Gln Asn Leu Thr Thr Thr
        35                  40                  45

Tyr Glu Ile Val Leu Trp Gln Pro Val Thr Ala Asp Leu Ile Val Lys
    50                  55                  60

Lys Lys Gln Val His Phe Val Asn Ala Ser Asp Val Asp Asn Val
65                  70                  75                  80

Lys Ala His Leu Asn Val Ser Gly Ile Pro Cys Ser Val Leu Leu Ala
                85                  90                  95

Asp Val Glu Asp Leu Ile Gln Gln Ile Ser Asn Asp Thr Val Ser
            100                 105                 110

Pro Arg Ala Ser Ala Ser Tyr Tyr Glu Gln Tyr His Ser Leu Asn Glu
        115                 120                 125

Ile Tyr Ser Trp Ile Glu Phe Ile Thr Glu Arg His Pro Asp Met Leu
    130                 135                 140

Thr Lys Ile His Ile Gly Ser Ser Phe Glu Lys Tyr Pro Leu Tyr Val
145                 150                 155                 160

Leu Lys Val Ser Gly Lys Glu Gln Ala Ala Lys Asn Ala Ile Trp Ile
                165                 170                 175

Asp Cys Gly Ile His Ala Arg Glu Trp Ile Ser Pro Ala Phe Cys Leu
            180                 185                 190

Trp Phe Ile Gly His Ile Thr Gln Phe Tyr Gly Ile Ile Gly Gln Tyr
        195                 200                 205

Thr Asn Leu Leu Arg Leu Val Asp Phe Tyr Val Met Pro Val Val Asn
    210                 215                 220

Val Asp Gly Tyr Asp Tyr Ser Trp Lys Lys Asn Arg Met Trp Arg Lys
225                 230                 235                 240

Asn Arg Ser Phe Tyr Ala Asn Asn His Cys Ile Gly Thr Asp Leu Asn
                245                 250                 255
```

```
                                -continued

Arg Asn Phe Ala Ser Lys His Trp Cys Glu Glu Gly Ala Ser Ser Ser
            260                 265                 270

Ser Cys Ser Glu Thr Tyr Cys Gly Leu Tyr Pro Glu Ser Glu Pro Glu
        275                 280                 285

Val Lys Ala Val Ala Ser Phe Leu Arg Arg Asn Ile Asn Gln Ile Lys
    290                 295                 300

Ala Tyr Ile Ser Met His Ser Tyr Ser Gln His Ile Val Phe Pro Tyr
305                 310                 315                 320

Ser Tyr Thr Arg Ser Lys Ser Lys Asp His Glu Glu Leu Ser Leu Val
                325                 330                 335

Ala Ser Glu Ala Val Arg Ala Ile Glu Lys Ile Ser Lys Asn Thr Arg
                340                 345                 350

Tyr Thr His Gly His Gly Ser Glu Thr Leu Tyr Leu Ala Pro Gly Gly
            355                 360                 365

Gly Asp Asp Trp Ile Tyr Asp Leu Gly Ile Lys Tyr Ser Phe Thr Ile
370                 375                 380

Glu Leu Arg Asp Thr Gly Thr Tyr Gly Phe Leu Leu Pro Glu Arg Tyr
385                 390                 395                 400

Ile Lys Pro Thr Cys Arg Glu Ala Phe Ala Ala Val Ser Lys Ile Ala
            405                 410                 415

Trp His Val Ile Arg Asn Val
            420
```